US009932619B2

(12) United States Patent
Liu et al.

(10) Patent No.: US 9,932,619 B2
(45) **Date of Patent: *Apr. 3, 2018**

(54) METHODS AND MATERIALS FOR BIOSYNTHESIS OF MOGROSIDE COMPOUNDS

(71) Applicant: Evolva SA, Reinach (CH)

(72) Inventors: Yaoquan Liu, Palo Alto, CA (US); Jorgen Hansen, Frederiksberg (DK); Jens Houghton-Larsen, Birkerod (DK); Muthuswamy Panchapagesa Murali, Chennai (IN); Sathish Kumar, Tamil Nadu (IN); Nina Nicoline Rasmussen, Hvidor (DK)

(73) Assignee: EVOLVA SA, Reinach (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/442,694

(22) PCT Filed: Dec. 4, 2013

(86) PCT No.: PCT/EP2013/075510

§ 371 (c)(1),
(2) Date: May 13, 2015

(87) PCT Pub. No.: WO2014/086842

PCT Pub. Date: Jun. 12, 2014

(65) Prior Publication Data

US 2015/0322473 A1 Nov. 12, 2015

Related U.S. Application Data

(60) Provisional application No. 61/733,220, filed on Dec. 4, 2012.

(51) Int. Cl.

| | |
|---|---|
| ***C12P 33/20*** | (2006.01) |
| ***C12P 19/18*** | (2006.01) |
| ***C12P 19/56*** | (2006.01) |
| ***C12N 1/00*** | (2006.01) |
| ***C12N 9/10*** | (2006.01) |
| ***C12P 33/08*** | (2006.01) |
| ***C12N 9/02*** | (2006.01) |
| ***C12N 9/14*** | (2006.01) |
| ***C12N 9/90*** | (2006.01) |
| ***C12P 33/00*** | (2006.01) |
| ***C12P 33/12*** | (2006.01) |
| *C12N 15/80* | (2006.01) |

(52) U.S. Cl.

CPC ............ *C12P 33/20* (2013.01); *C12N 9/0071* (2013.01); *C12N 9/0073* (2013.01); *C12N 9/1048* (2013.01); *C12N 9/14* (2013.01); *C12N 9/90* (2013.01); *C12P 19/18* (2013.01); *C12P 19/56* (2013.01); *C12P 33/00* (2013.01); *C12P 33/08* (2013.01); *C12P 33/12* (2013.01); *C12Y 114/00* (2013.01); *C12Y 303/00* (2013.01); *C12Y 504/99033* (2013.01); *C12N 15/80* (2013.01); *C12Y 114/13132* (2013.01)

(58) Field of Classification Search

CPC ....... C12P 19/18; C12P 19/56; C12P 19/0071; C12P 19/0073; C12P 19/1048; C12P 19/14; C12P 19/90; C12P 33/00; C12P 33/20; C12P 33/08; C12P 33/12; C12N 15/80; C12Y 114/00; C12Y 114/13132; C12Y 303/00; C12Y 504/99033; Y02P 20/52

See application file for complete search history.

(56) References Cited

U.S. PATENT DOCUMENTS

| | | | |
|---|---|---|---|
| 8,257,948 | B1 | 9/2012 | Markosyan |
| 2007/0118916 | A1 | 5/2007 | Puzio et al. |
| 2015/0322473 | A1 | 11/2015 | Liu et al. |

FOREIGN PATENT DOCUMENTS

| | | |
|---|---|---|
| EP | 1510573 | 3/2005 |
| EP | 1897951 | 12/2010 |
| WO | 2001/012845 | 2/2001 |
| WO | 2008/062165 | 5/2008 |
| WO | 2008/065370 | 5/2008 |
| WO | 2010/106318 | 9/2010 |
| WO | 2011/153378 | 12/2011 |
| WO | 2013/076577 | 5/2013 |

OTHER PUBLICATIONS

Bateman et al., "Pfam 3.1: 1313 multiple alignments and profile HMMs match the majority of proteins," Nucl Acids Res. 27(1):260-2 (1999).
Bowles et al., "Glycosyltransferases: manages of small molecules," Curr Opin Plant Biol. 8(3):254-63 (2005).
Brochado et al., "Improved vanillin production in baker's yeast through in silico design," Microb Cell Fact. 9:84 (2010).
Chatuvedula & Prakash, "Cucurbitane glycosides from Siraitia grosvenorii," J Carbohydrate Chem. 30(1):16-26 (2011).
Chiu et al., "Biotransformation of mogrosides from Siraitia grosvenorii Swingle by *Saccharomyces cerevisiae*," J Agric Food Chem. 61(29):7127-34 (2013).
Donald et al., "Effects of overproduction of the catalytic domain of 3-hydroxy-3-methylglutaryl coenzyme A reductase on squalene synthesis in *Saccharomyces cerevisiae*," Appl Environ Microbial. 63(9):3341-4 (1997).
Hamberger & Bak, "Plant P450s as versatile drivers for evolution of species-specific chemical diversity," Philos Trans R Soc Land B Biol Sci. 368(1612):20120426 (2013).
Jia & Yang, "A minor, sweet cucurbitane glycoside from Siraitia grosvenorii," Nat Prod Commun. 4(6):769-72 (2009).
Kasai et al., "Sweet cucurbitane glycosides from fruits of Siraitia siamensis (chi-zi luo-han-guo), a Chinese folk medicine," Agric Biol Chem. 53(12):3347-9 (1989).

(Continued)

*Primary Examiner* — Terry A McKelvey
*Assistant Examiner* — Aaron J Kosar
(74) *Attorney, Agent, or Firm* — McDonnell Boehnen Hulbert & Berghoff LLP

(57) ABSTRACT

The invention relates to methods for producing mogrosides with the aid of enzymes. In particular the invention proposes various biosynthetic pathways useful for mogroside production and enzymes useful for mogroside production are provided. Furthermore, the invention provides recombinant hosts useful in performing the methods of the invention.

26 Claims, 14 Drawing Sheets

(56) References Cited

OTHER PUBLICATIONS

Kirby et al., "Engineering triterpene production in *Saccharomyces cerevisiae*-beta-amyrin synthase from Artemisia annua," FEBS J. 275(8):1852-9 (2008).
Li et al. "Cucurbitane glycosides from unripe fruits of Lo Han Kuo (*Siraiitia grosvenori*)," Chem Pharm Bull (Tokyo) 54 (10):1425-8 (2006).
Matsumoto, "Minor cucurbitane-glycosides from fruits of Siraitia grosvenorii (Cucurbitaceae)," Chem Pharm Bull. 38 (7):2030-2 (1990).
Richman, Functional genomics uncovers three glucosyltransferases involved in the synthesis of the major sweet glucosides of Stevia rebaudiana, Plant J. 41(1):56-67 (2005).
Seki, Licorice beta-amyrin 11-oxidase, a cytochrome P450 with a key role in the biosynthesis of the triterpene sweetener glycyrrhizin, Proc Natl Acad Sci U S A. 105(37):14204-9 (2008).
Shibuya et al., "Cucurbitadienol synthase, the first committed enzyme for cucurbitacin biosynthesis, is a distinct enzyme from cycloartenol synthase for phytosterol biosynthesis," Tetrahedron 60(33):6995-7003 (2004).
Sonnhammer et al., "Pfam: a comprehensive database of protein domain families based on seed alignments," Proteins 28(3):405-20 (1997).
Sonnhammer et al., "Pfam: multiple sequence alignments and HMM-profiles of protein domains," Nucl Acids Res. 26(1):320-2 (1998).
Takemoto et al., "Studies on the constituents of Fructus Momordicae. I. On the sweet principle," Yakugaku Zasshi 103(11)1151-4 (1983).
Takemoto et al., "Studies on the constituents of Fructus Momordicae. II. Structure of sapogenin," Yakugaku Zasshi 103(11):1155-66 (1983).
Takemoto et al., "Studies on the constituents of Fructus Momordicae. III. Structures of mogrosides," Yakugaku Zasshi 103(11):1167-73 (1983).
Tang et al., "An efficient approach to finding Siraitia grosvenorii triterpene biosynthetic genes by RNA-seq and digital gene expression analysis," BMC Genomics 12:343 (2011).
Thompson et al., "CLUSTAL W: improving the sensitivity of progressive multiple sequence alignment through sequence weighting, position-specific gap penalties and weight matrix choice," Nucleic Acids Res. 22(22):4673-80 (1994).
Ukiya et al., "Inhibitory effects of cucurbitane glycosides and other triterpenoids from the fruit of Momordica grosvenori on epstein-barr virus early antigen induced by tumor promoter 12-O-tetradecanoylphorbol-13-acetate," J Agric Food Chem. 50(23):6710-5 (2002).
International Search Report issued by the International Searching Authority for International Application No. PCT/EP2013/075510, dated May 4, 2015 (pp. 1-7).
Written Opinion of the International Searching Authority for International Application No. PCT/EP2013/075510, dated Apr. 23, 2014 (pp. 1-14).
Written Opinion of the International Preliminary Examining Authority for International Application No. PCT/EP2013/075510, dated Feb. 4, 2015 (pp. 1-14).
International Search Report issued by the International Searching Authority for International Application No. PCT/IB2012/002857, dated May 14, 2013 (pp. 1-6).
Written Opinion of the International Searching Authority for International Application No. PCT/IB2012/002857, dated May 14, 2013 (pp. 1-7).
International Preliminary Report on Patentability issued by the International Preliminary Examining Authority for International Application No. PCT/IB2012/002857, dated Jan. 9, 2014 (pp. 1-13).
GenBank Accession No. AAS01524 (pp. 1-2).
GenBank Accession No. ADC84219 (pp. 1-2).
GenBank Accession No. BAA33460 (pp. 1-2).
GenBank Accession No. BAA76902 (pp. 1-2).
GenBank Accession No. BAB83085 (pp. 1-2).
GenBank Accession No. BAB83086 (pp. 1-2).
GenBank Accession No. BAD34645.1 (pp. 1-2).
GenBank Accession No. BAE53431 (pp. 1-2).
GenBank Accession No. XP_002264289 (pp. 1-2).
GenBank Accession No. XP_002310905 (pp. 1-2).
Guo et al., "Protein tolerance to random amino acid change," Proc Natl Acad Sci U 22;101(25):9205-10 (2004).
Nilsson et al., "Chemical synthesis of proteins," Annu Rev Biophys Biomol Struct. 34: 91-118 (2005).
Poppenberger et al., "Heterologous expression of Arabidopsis UDP-glucosyltransferases in *Saccharomyces cerevisiae* for production of zearalenone-4-O-glucoside," Appl Environ Microbial. 72(6):4404-10 (2006).
Shao et al., "Crysal structures of a multifunctional triterpene/flavonoid glycosyltransferase from Medicago truncatula," Plant Cell. 17(11):3141-54 (2005).
Xiong et al., "Biosynthesis of triterpene glycoside in Lo Han Kuo," Guangdong Pharmaceutical University 27(5):544-5 (2011). English abstract provided.
Wikipedia: "Mogroside," Internet Archive Wayback Machine Jan. 9, 2014 (Jan. 9, 2014), retrieved from the Internet: URL:https://web.archive.org/web/20140109130110/http://en.wikipedia.org/wiki/Mogroside [retrieved on Apr. 14, 2016] (pp. 1-2).
UniProt Database Accession No. AT223684, "Stevia rebaudiana protein Seq Id No. 10008," Feb. 3, 2011 (1 page).
GenBank Accession No. XP_008442743; last accessed Apr. 28, 2016 (pp. 1-2).
GenBank Accession No. XP_008450117; last accessed Apr. 28, 2016 (p. 1-2).
GenBank Accession No. XP_008454322; last accessed Apr. 21, 2016 (pp. 1-2).
UniProt Accession No. F6GXH0; last accessed Apr. 21, 2016 (pp. 1-2).
UniProt Accession No. F6HIX7; last accessed Apr. 28, 2016 (pp. 1-2).
UniProt Accession No. K7NBR2; last accessed Apr. 29, 2016 (p. 1).
UniProt Accession No. K7NBZ9; last accessed Apr. 21, 2016 (p. 1).
UniProt Accession No. W7PH03; last accessed Apr. 28, 2016 (p. 1).
UniProt Accession No. W9SCC7; last accessed Apr. 21, 2016 (p. 1).
UniProt Accession No. K7NBX0; last accessed Nov. 29, 2016 (pp. 1-4).
Non-Final Office Action for U.S. Appl. No. 14/356,782, dated Oct. 30, 2015 (pp. 1-12).
Final Office Action for U.S. Appl. No. 14/356,782, dated Jul. 18, 2016, pp. 1-16.
Response to Non-Final Office Action for U.S. Appl. No. 14/356,782, filed Mar. 22, 2016 (pp. 1-10).
Non-Final Office Action for U.S. Appl. No. 14/504,109, dated Jun. 29, 2016, pp. 1-13.
Final Office Action for U.S. Appl. No. 14/504,109, dated Sep. 8, 2016, pp. 1-18.
International Search Report and Written Opinion of the International Searching Authority for International Application No. PCT/EP2015/072645, dated May 20, 2016 (pp. 1-39).
Written Opinion of the International Preliminary Examining Authority for International Application No. PCT/EP2013/075510, dated May 5, 2015 (pp. 1-15).
UniProt Accession No. A7VJN1 (pp. 1-5).
UniProt Accession No. B5AID3 (pp. 1-4).
UniProt Accession No. B5AID4 (pp. 1-4).
UniProt Accession No. B5AID5 (pp. 1-4).
UniProt Accession No. B9R6V0 (pp. 1-5).
UniProt Accession No. B9RHC3 (pp. 1-6).
UniProt Accession No. B9S6Y2 (pp. 1-5).
UniProt Accession No. B9S7T0 (pp. 1-5).
UniProt Accession No. B9S7W5 (pp. 1-5).
UniProt Accession No. B9SX91 (pp. 1-6).
UniProt Accession No. B9T0Y3 (pp. 1-5).
UniProt Accession No. B9WZW7 (pp. 1-5).
UniProt Accession No. C4P9M2 (pp. 1-5).
UniProt Accession No. C4P9M3 (pp. 1-5).
UniProt Accession No. C6KE07 (pp. 1-5).

(56) References Cited

OTHER PUBLICATIONS

UniProt Accession No. C6KE08 (pp. 1-5).
UniProt Accession No. C7EDC9 (pp. 1-5).
UniProt Accession No. C7EDD0 (pp. 1-5).
UniProt Accession No. D6QX35 (pp. 1-5).
UniProt Accession No. D6QX37 (pp. 1-5).
UniProt Accession No. D6QX38 (pp. 1-5).
UniProt Accession No. D6QX39 (pp. 1-5).
UniProt Accession No. D6QX40 (pp. 1-5).
UniProt Accession No. D6QX41 (pp. 1-5).
UniProt Accession No. D6QX42 (pp. 1-5).
UniProt Accession No. D6QX43 (pp. 1-5).
UniProt Accession No. D6QX44 (pp. 1-5).
UniProt Accession No. D6QX45 (pp. 1-5).
UniProt Accession No. D6QX47 (pp. 1-5).
UniProt Accession No. D6QX53 (pp. 1-5).
UniProt Accession No. D6QX55 (pp. 1-5).
UniProt Accession No. O65402 (pp. 1-9).
UniProt Accession No. O65403 (pp. 1-10).
UniProt Accession No. O65404 (pp. 1-10).
UniProt Accession No. O65726 (pp. 1-7).
UniProt Accession No. O65727 (pp. 1-7).
UniProt Accession No. O81000 (pp. 1-9).
UniProt Accession No. Q42760 (pp. 1-5).
UniProt Accession No. Q42761 (pp. 1-5).
UniProt Accession No. Q84LE3 (pp. 1-5).
UniProt Accession No. Q8GSL6 (pp. 1-6).
UniProt Accession No. Q8GSM8 (pp. 1-5).
UniProt Accession No. Q8GSM9 (pp. 1-5).
UniProt Accession No. Q9SM02 (pp. 1-11).
UniProt Accession No. Q9T064 (Q8VYH2) (pp. 1-10).

0.57% Mogroside V 0.12% Mogroside IV 0.047% Siamenoside I 0.036% 11-Oxo-Mogroside V index (SEV)

425

Mogroside V

392

Mogroside IV

563

Siamenoside I

84

11-Oxo-Mogroside V

Cucurbitadienol

Mogrol

Mogrol

Mogroside IA1

Mogroside IE1

Mogroside II E

Mogroside IIIA2

Mogroside III

Mogroside IV A

Mogroside V

Mogrol

Mogroside IIA$_1$

Mogroside III

Mogroside V

Mogroside IIE

Mogroside IA$_1$

Mogroside IVA

Mogroside III

Mogroside IE$_1$ cucurbitadienol mogrol 11-oxo-mogrol dioxidosqualene 24,25 epoxy cucurbitadienol mogrol 11-oxo-mogrol A
Mogroside I A1
Mogroside II A
mogrol
B
Mogroside I A1 (proton plus Na adduct)
Mogroside II A (proton plus Na adduct)
Mogroside III A1 (proton plus Na adduct)
Relative Abundance
Time (min)

mogrol

Mogroside I A1

Mogroside II A

Mogroside III A1

METHODS AND MATERIALS FOR BIOSYNTHESIS OF MOGROSIDE COMPOUNDS

FIELD OF INVENTION

The present invention relates to methods and materials for biosynthesis of mogroside compounds, and more particularly to methods involving use of cytochrome P450 enzymes to produce mogrol and/or using uridine-5'-diphospho (UDP) dependent glucosyltransferases (UGTs) to glycosylate mogrol and produce various mogrol glycosides (mogrosides). The methods may also involve use of enzymes involved in biosynthesis of substrates for mogrol production.

BACKGROUND OF INVENTION

Mogrosides are a family of triterpene glycosides isolated from fruits of *Siraitia grosvenorii* (Swingle), also known as *Momordica grosvenori* (Swingle). Extracts of the fruits are commercially used as natural sweeteners. Four major compounds, Mogroside V, Mogroside IV, Siamenoside I, and 11-Oxomogroside V, have been identified from the fruits of *Siraitia grosvenorii* (Swingle) that are responsible for the sweetness of the fruits (see FIG. 1). Mogroside V is the most abundant of these four compounds at approximately 0.57% (w/w) of the dry fruit, followed by Mogroside IV and Siamenoside I, each of which contain four glucose moieties. 11-Oxomogroside V has a ketone group instead of a hydroxyl at C-11. See, e.g., Takemoto, et al., *Yakugaku Zasshi,* 103, 1151-1154; 1155-1166; 1167-1173, (1983); Kasai, et al., *Agric. Biol. Chem.* 53, 3347-3349 (1989); Matsumoto, *Chem. Pharm. Bull.* 38, 2030-2032 (1990); and Prakash, et al., *J. Carbohydrate Chem.* 30, 16-26 (2011). However, the enzymes responsible for producing mogrosides have not been identified.

Tang et al. BMC Genomics 2011, 12:343 describes seven CYP450s and five UDPGs as potential candidates involved in mogroside biosynthesis. However, the document does not specifically identify any CYPs or UDPGs involved in mogroside biosynthesis.

SUMMARY OF INVENTION

The present invention provides methods and materials for biosynthesis of mogroside compounds. Interestingly, the invention provides enzymes involved in mogroside biosynthesis.

Mogroside biosynthesis may involve several steps, and accordingly it is an aspect of the present invention to provide enzymes capable of catalysing each of these steps. It is however also foreseen that the methods may involve performing only some of the steps enzymatically, whereas others may be performed by other means.

In one aspect, this document features a method of producing a mogroside compound.

Thus, the invention provides a method of producing a mogroside, wherein the method comprises one or more of the following steps:

Step Ia. Enhancing levels of oxido-squalene

Step Ib. Enhancing levels of dioxido-squalene

Step IIa. Oxido-squalene→cucurbitadienol

Step IIb. Dioxido-squalene→24,25 epoxy cucurbitadienol

Step IIIa. Cucurbitadienol→11-hydroxy-cucurbitadienol

Step IIIb. 24,25 epoxy cucurbitadienol→11-hydroxy-24,25 epoxy cucurbitadienol

Step IVa. 11-hydroxy-cucurbitadienol→mogrol

Step IVb. 11-hydroxy-24,25 epoxy cucurbitadienol→mogrol

Step V mogrol→mogroside

Methods for performing each of the above-mentioned steps are described herein below. In particular, enzymes or mixture of enzymes useful for each of above-mentioned steps are described in details herein below.

The invention also features a recombinant host comprising one or more of the following heterologous nucleic acids:

IIa. Heterologous nucleic acid(s) encoding an enzyme or mixture of enzymes capable of catalysing Step IIa (Oxido-squalene→cucurbitadienol)

IIb. Heterologous nucleic acid(s) encoding an enzyme or mixture of enzymes capable of catalysing Step IIb (Dioxido-squalene→24,25 epoxy cucurbitadienol)

IIIa. Heterologous nucleic acid(s) encoding an enzyme or mixture of enzymes capable of catalysing Step IIIa (Cucurbitadienol→11-hydroxy-cucurbitadienol)

IIIb. Heterologous nucleic acid(s) encoding an enzyme or mixture of enzymes capable of catalysing Step IIIb (24,25 epoxy cucurbitadienol→11-hydroxy-24,25 epoxy cucurbitadienol)

IVa. Heterologous nucleic acid(s) encoding an enzyme or mixture of enzymes capable of catalysing Step IVa (11-hydroxy-cucurbitadienol→mogrol)

IVb. Heterologous nucleic acid(s) encoding an enzyme or mixture of enzymes capable of catalysing Step IVb (11-hydroxy-24,25 epoxy cucurbitadienol→mogrol)

V Heterologous nucleic acid(s) encoding an enzyme or mixture of enzymes capable of catalysing Step V (mogrol→mogroside)

In addition to the heterologous nucleic acids, said recombinant host may have been modified to achieve Step Ia and/or Step Ib.

Unless otherwise defined, all technical and scientific terms used herein have the same meaning as commonly understood by one of ordinary skill in the art to which the invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting. Other features and advantages of the invention will be apparent from the following detailed description. Applicants reserve the right to alternatively claim any disclosed invention using the transitional phrase "comprising," "consisting essentially of," or "consisting of," according to standard practice in patent law.

DESCRIPTION OF DRAWINGS

FIG. 11A shows the LC-MS chromatogram of reference mogroside I A1, while FIG. 11B shows the LC-MS chromatogram of a sample of yeast strain EFSC1563 expressing UGT1576 in a culture fed 50 uM mogrol.

DETAILED DESCRIPTION OF THE INVENTION

Method of Producing a Mogroside

Figure 2:
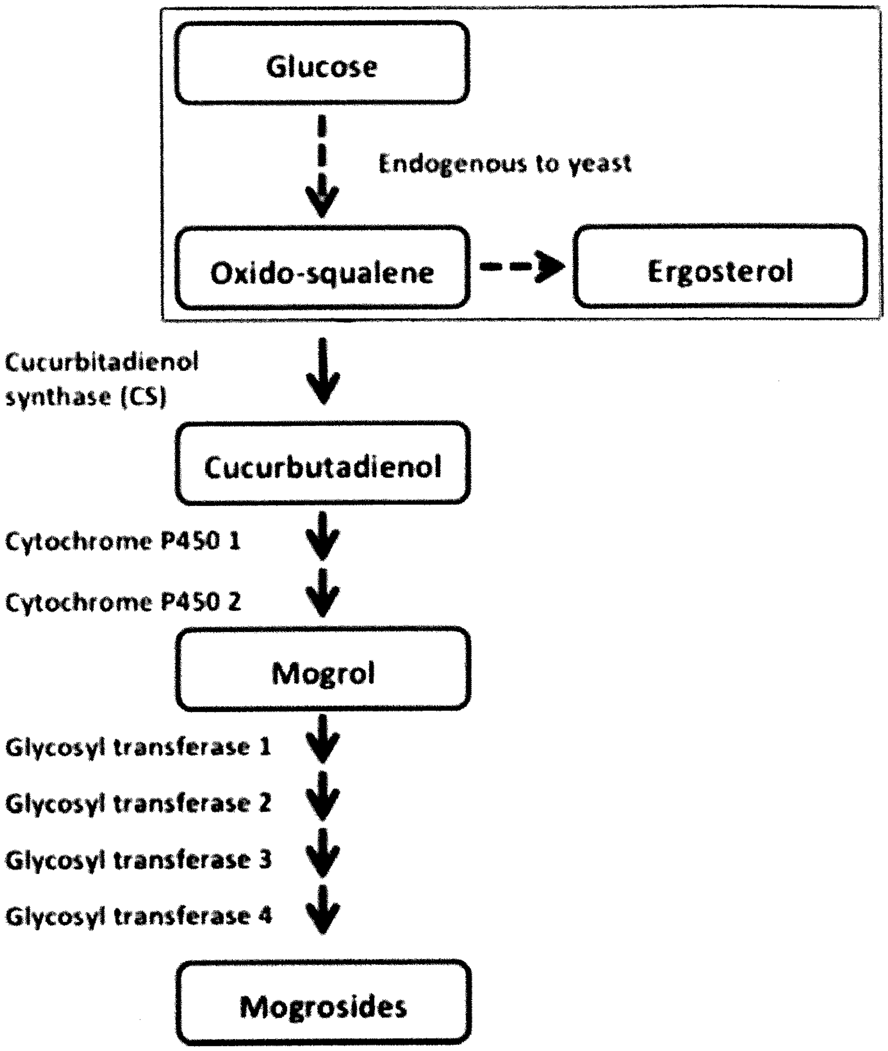
FIG. 2 is a schematic of the pathway for the production of mogrosides from glucose.

This document is based on the invention that recombinant hosts such as microorganisms, plant cells, or plants can be developed that express polypeptides useful for the biosynthesis of mogrol (the triterpene core) and various mogrol glycosides (mogrosides). The aglycone mogrol is glycosylated with different numbers of glucose moieties to form various mogroside compounds. Recombinant microorganisms are particularly useful hosts. The recombinant host may be any of the recombinant hosts described herein below in the section "Recombinant host". Expression of these biosynthetic polypeptides in various microbial chassis allows mogrol and its glycosides to be produced in a consistent, reproducible manner from energy and carbon sources such as sugars, glycerol, $CO_2$, $H_2$ and sunlight. FIG. 2 provides a schematic of the pathway for production of mogrol and various mogrosides from glucose.

It is one aspect of the invention to provide a method of producing a mogroside, wherein the method comprises one or more of the following steps:

Step Ia. Enhancing levels of oxido-squalene

Step Ib. Enhancing levels of dioxido-squalene

Step IIa. Oxido-squalene→cucurbitadienol

Step IIb. Dioxido-squalene→24,25 epoxy cucurbitadienol

Step IIIa. Cucurbitadienol→11-hydroxy-cucurbitadienol

Step IIIb. 24,25 epoxy cucurbitadienol→11-hydroxy-24,25 epoxy cucurbitadienol

Step IVa. 11-hydroxy-cucurbitadienol→mogrol

Step IVb. 11-hydroxy-24,25 epoxy cucurbitadienol→mogrol

Step V mogrol→mogroside

Methods and materials for performing each of the steps are described in more detail herein below. Each of the steps of the method results in generation of a product. Said products may also be referred to as "intermediate products" herein. Each step uses a substrate, which may also be referred to as "precursor molecules". It is clear from above that the intermediate products also may serve as precursor molecules for a subsequent step.

Thus, the invention provides methods of producing mogrosides, wherein the method may comprise the steps of Step Ia. Enhancing levels of oxido-squalene Step IIa. Oxido-squalene→cucurbitadienol Step IIIa. Cucurbitadienol→11-hydroxy-cucurbitadienol Step IVa. 11-hydroxy-cucurbitadienol→mogrol Step V mogrol→mogroside and optionally isolating said mogroside.

The invention also provides methods of producing mogrosides, wherein the method may comprise the steps of a) Providing oxido-squalene b) Performing Steps IIa, IIIa, IVa and V identified above c) optionally isolating said mogroside The invention also provides methods of producing mogrosides, wherein the method may comprise the steps of Step Ib. Enhancing levels of dioxido-squalene Step IIb. Dioxido-squalene→24,25 epoxy cucurbitadienol Step IIIb. 24,25 epoxy cucurbitadienol→11-hydroxy-24,25 epoxy cucurbitadienol Step IVb 11-hydroxy-24,25 epoxy cucurbitadienol→mogrol Step V mogrol→mogroside and optionally isolating said mogroside.

The invention also provides methods of producing mogrosides, wherein the method may comprise the steps of a) providing dioxido-squalene b) performing steps IIb, IIIb, IVb and V identified above c) optionally isolating said mogroside The invention also provides methods of producing mogrosides, wherein said mogroside may be a higher glycosylated mogroside, wherein the method may comprise the steps of a) providing cucurbitadienol b) performing steps IIIa, IVa and V identified above c) optionally isolating said mogroside The invention also provides methods of producing mogrosides, wherein said mogroside may be a higher glycosylated mogroside, wherein the method may comprise the steps of a) providing 24,25 epoxy cucurbitadienol b) performing steps IIIb, IVb and V identified above c) optionally isolating said mogroside The invention provides methods of producing mogrosides, wherein the method may comprise the steps of a) providing mogrol b) performing step V identified above c) optionally isolating said mogroside The invention provides methods of producing mogrol, wherein the method may comprise the steps of a) providing dioxido-squalene b) performing steps IIb, IIb and IVb identified above c) optionally isolating said mogrol In general, the method may be performed either in vitro or in vivo. It is also comprised within the invention that some steps are performed in vitro, whereas others may be performed in vivo. Thus, for example the first steps may be performed in vitro and where after an intermediate product may be fed to recombinant host cells, capable of performing the remaining steps of the method. Alternatively, the first steps may be performed in vivo and where after an intermediate product may be used as substrate for the subsequent step(s) performed in vitro. Other combinations can also be envisaged.

When said methods are performed in vitro each of the steps of the methods may be performed separately. Alternatively, one or more of the steps may be performed within the same mixture. In embodiments wherein some or all of the steps of the methods are performed separately, then the intermediate product of each of the steps may be purified or partly purified before performing the next step.

When said methods are performed in vivo, the methods employ use of a recombinant host expressing one or more of said enzymes or the methods may employ use of several recombinant hosts expressing one or more of said enzymes. The methods may also employ a mixture of recombinant and non-recombinant host. If more than one host is used then the hosts may be co-cultivated, or they may be cultured separately. If the hosts are cultivated separately the intermediate products may be recovered and optionally purified and partially purified and fed to recombinant hosts using the intermediate products as substrates. Useful recombinant hosts to be used with the invention are described herein below.

Said oxido-squalene, dioxido-squalene, cucurbitadienol, 24,25 epoxy cucurbitadienol or mogrol may be provided in any suitable manner. For example said oxido-squalene, dioxido-squalene, cucurbitadienol, 24,25 epoxy cucurbitadienol or mogrol may be provided in isolated form or as part of a composition or an extract. In embodiments of the invention, wherein the methods are performed in vivo, said oxido-squalene, dioxido-squalene, cucurbitadienol, 24,25 epoxy cucurbitadienol or mogrol may be added to the cultivation medium. It is also comprised within the invention that a recombinant host is used, which endogenously expresses oxido-squalene, dioxido-squalene, cucurbitadienol, 24,25 epoxy cucurbitadienol or mogrol.

Recombinant hosts described herein below can be used in methods to produce mogroside compounds. For example, if the recombinant host is a microorganism, the method can include growing the recombinant microorganism in a culture medium under conditions in which one or more of the enzymes catalyzing step(s) of the methods of the invention, e.g. synthases, hydrolases, CYP450s and/or UGTs are expressed. The recombinant microorganism may be grown in a fed batch or continuous process. Typically, the recombinant microorganism is grown in a fermenter at a defined temperature(s) for a desired period of time.

A cell lysate can be prepared from the recombinant host expressing one or more enzymes and be used to contact a substrate, such that mogroside compounds can be produced. For example, a cell lysate can be prepared from the recombinant host expressing one or more UGTs and used to contact mogrol, such that mogroside compounds can be produced.

In some embodiments, mogroside compounds can be produced using whole cells that are fed raw materials that contain precursor molecules, e.g., mogrol. The raw materials may be fed during cell growth or after cell growth. The whole cells may be in suspension or immobilized. The whole cells may be in fermentation broth or in a reaction buffer. In some embodiments a permeabilizing agent may be required for efficient transfer of substrate into the cells.

Levels of products, substrates and intermediates can be determined by extracting samples from culture media for analysis according to published methods. Mogroside compounds can be recovered from the culture or culture medium using various techniques known in the art.

Recombinant Host

This document also feature recombinant hosts. As used herein, the term recombinant host is intended to refer to a host, the genome of which has been augmented by at least one incorporated DNA sequence. Said incorporated DNA sequence may be a heterologous nucleic acid encoding one or more polypeptides. Such DNA sequences include but are not limited to genes that are not naturally present, DNA sequences that are not normally transcribed into RNA or translated into a protein ("expressed"), and other genes or DNA sequences which one desires to introduce into the non-recombinant host. It will be appreciated that typically the genome of a recombinant host described herein is augmented through the stable introduction of one or more recombinant genes. Said recombinant gene may also be a heterologous nucleic acid encoding one or more polypeptides. Generally, the introduced DNA or heterologous nucleic acid is not originally resident in the host that is the recipient of the DNA, but it is within the scope of the invention to isolate a DNA segment from a given host, and to subsequently introduce one or more additional copies of that DNA into the same host, e.g., to enhance production of the product of a gene or alter the expression pattern of a gene. In some instances, the introduced DNA or heterologous nucleic acid will modify or even replace an endogenous gene or DNA sequence by, e.g., homologous recombination or site-directed mutagenesis.

In particular, the recombinant host according to the present invention comprises one or more of the following heterologous nucleic acids:

IIa. Heterologous nucleic acid(s) encoding an enzyme or mixture of enzymes capable of catalysing Step IIa (Oxido-squalene→cucurbitadienol)

IIb. Heterologous nucleic acid(s) encoding an enzyme or mixture of enzymes capable of catalysing Step IIb (Dioxido-squalene→24,25 epoxy cucurbitadienol)

IIIa. Heterologous nucleic acid(s) encoding an enzyme or mixture of enzymes capable of catalysing Step IIIa (Cucurbitadienol→11-hydroxy-cucurbitadienol)

IIIb. Heterologous nucleic acid(s) encoding an enzyme or mixture of enzymes capable of catalysing Step IIIb (24,25 epoxy cucurbitadienol→11-hydroxy-24,25 epoxy cucurbitadienol)

IVa. Heterologous nucleic acid(s) encoding an enzyme or mixture of enzymes capable of catalysing Step IVa (11-hydroxy-cucurbitadienol→mogrol)

IVb. Heterologous nucleic acid(s) encoding an enzyme or mixture of enzymes capable of catalysing Step IVb (11-hydroxy-24,25 epoxy cucurbitadienol→mogrol)

V Heterologous nucleic acid(s) encoding an enzyme or mixture of enzymes capable of catalysing Step V (mogrol→mogroside)

In addition to the heterologous nucleic acids, said recombinant host may have been modified to achieve Step Ia and/or Step Ib.

Enzymes capable of catalysing each of these steps are described herein below in more detail.

In one embodiment of the invention, the recombinant host according to the present invention may comprise the following heterologous nucleic acids:

IIa. Heterologous nucleic acid(s) encoding an enzyme or mixture of enzymes capable of catalysing Step IIa (Oxido-squalene→cucurbitadienol)

IIIa. Heterologous nucleic acid(s) encoding an enzyme or mixture of enzymes capable of catalysing Step IIIa (Cucurbitadienol→11-hydroxy-cucurbitadienol)

IVa. Heterologous nucleic acid(s) encoding an enzyme or mixture of enzymes capable of catalysing Step IVa (11-hydroxy-cucurbitadienol→mogrol)

V Heterologous nucleic acid(s) encoding an enzyme or mixture of enzymes capable of catalysing Step V (mogrol→mogroside)

and optionally said recombinant host may further have been modified to achieve Step Ia.

Said recombinant host cell is in particular useful in methods for producing mogrosides.

In one embodiment of the invention, the recombinant host according to the present invention may comprise the following heterologous nucleic acids:

IIIa. Heterologous nucleic acid(s) encoding an enzyme or mixture of enzymes capable of catalysing Step IIIa (Cucurbitadienol→11-hydroxy-cucurbitadienol)

IVa. Heterologous nucleic acid(s) encoding an enzyme or mixture of enzymes capable of catalysing Step IVa (11-hydroxy-cucurbitadienol→mogrol)

V Heterologous nucleic acid(s) encoding an enzyme or mixture of enzymes capable of catalysing Step V (mogrol→mogroside)

Said recombinant host cell is in particular useful in methods for producing mogrosides comprising a step of providing curcubutadienol.

In one embodiment of the invention, the recombinant host according to the present invention may comprise the following heterologous nucleic acids:

V Heterologous nucleic acid(s) encoding an enzyme or mixture of enzymes capable of catalysing Step V (mogrol→mogroside)

Said recombinant host cell is in particular useful in methods for producing mogrosides comprising a step of providing mogrol.

In one embodiment of the invention, the recombinant host according to the present invention may comprise the following heterologous nucleic acids:

IIb. Heterologous nucleic acid(s) encoding an enzyme or mixture of enzymes capable of catalysing Step IIb (Dioxido-squalene→24,25 epoxy cucurbitadienol)

IIIb. Heterologous nucleic acid(s) encoding an enzyme or mixture of enzymes capable of catalysing Step IIIb (24,25 epoxy cucurbitadienol→11-hydroxy-24,25 epoxy cucurbitadienol)

IVb. Heterologous nucleic acid(s) encoding an enzyme or mixture of enzymes capable of catalysing Step IVb (11-hydroxy-24,25 epoxy cucurbitadienol→mogrol)

V Heterologous nucleic acid(s) encoding an enzyme or mixture of enzymes capable of catalysing Step V (mogrol→mogroside) And optionally said recombinant host may have been modified to achieve Step Ib.

Said recombinant host cell is in particular useful in methods for producing mogrosides.

In one embodiment of the invention, the recombinant host according to the present invention may comprise the following heterologous nucleic acids:

IIIb. Heterologous nucleic acid(s) encoding an enzyme or mixture of enzymes capable of catalysing Step IIIb (24,25 epoxy cucurbitadienol→11-hydroxy-24,25 epoxy cucurbitadienol)

IVb. Heterologous nucleic acid(s) encoding an enzyme or mixture of enzymes capable of catalysing Step IVb (11-hydroxy-24,25 epoxy cucurbitadienol→mogrol)

V Heterologous nucleic acid(s) encoding an enzyme or mixture of enzymes capable of catalysing Step V (mogrol→mogroside)

Said recombinant host cell is in particular useful in methods for producing mogrosides comprising a step of providing 24,25 epoxy cucurbitadienol.

In one embodiment of the invention, the recombinant host according to the present invention may comprise the following heterologous nucleic acids:

IIb. Heterologous nucleic acid(s) encoding an enzyme or mixture of enzymes capable of catalysing Step IIb (Dioxido-squalene→24,25 epoxy cucurbitadienol)

IIIb. Heterologous nucleic acid(s) encoding an enzyme or mixture of enzymes capable of catalysing Step IIIb (24,25 epoxy cucurbitadienol→11-hydroxy-24,25 epoxy cucurbitadienol)

IVb. Heterologous nucleic acid(s) encoding an enzyme or mixture of enzymes capable of catalysing Step IVb (11-hydroxy-24,25 epoxy cucurbitadienol→mogrol)

and optionally said recombinant host may have been modified to achieve Step Ib.

Said recombinant host cell is in particular useful in methods for producing mogrol.

Suitable recombinant hosts include microorganisms, plant cells, and plants.

Thus, in one embodiment, a recombinant host that produces a mogroside compound can include a recombinant gene encoding at least a first UGT selected from the group consisting of 73C3, 73C6, 85C2, 73C5, and 73E1, and a recombinant gene encoding at least a second UGT selected from the group consisting of UGT98, UGT1495, UGT1817, UGT5914, UGT8468 and UGT10391. For example, a recombinant host can include a recombinant gene encoding at least one UGT selected from 73C3, 73C6, 85C2, and 73E1; a recombinant gene encoding 73C5; and a recombinant gene encoding at least one UGT selected from the group consisting of UGT98, UGT1495, UGT1817, UGT5914, UGT8468 and UGT10391. One or more of the following also can be included in a recombinant host: a recombinant gene encoding a cucurbitadienol synthase (e.g., from *Cucurbita pepo* or monk fruit); a recombinant gene encoding a cytochrome P450 polypeptide selected from the group CYP533, CYP937, CYP1798, CYP1994, CYP2048, CYP2740, CYP3404, CYP3968, CYP4112, CYP4149, CYP4491, CYP5491, CYP6479, CYP7604, CYP8224, CYP8728, CYP10020, and CYP10285 (SEQ ID NOs:3-20, respectively); and a recombinant gene encoding a squalene synthase (e.g., from *Gynostemma pentaphyllum* or *Arabidopsis thaliana*). CYP5491 has previously also been referred to as CYP87.

At least one of the genes in the recombinant host is a recombinant gene, the particular recombinant gene(s) depending on the species or strain selected for use. Additional genes or biosynthetic modules can be included in order to increase yield of mogrol and mogrosides, improve efficiency with which energy and carbon sources are converted to mogrol and mogrosides, and/or to enhance productivity from the cell culture or plant.

The recombinant host further can include a recombinant gene encoding a cucurbitadienol synthase and/or a recombinant gene encoding a cytochrome P450 polypeptide (e.g., CYP533, CYP937, CYP1798, CYP1994, CYP2048, CYP2740, CYP3404, CYP3968, CYP4112, CYP4149, CYP4491, CYP5491, CYP6479, CYP7604, CYP8224, CYP8728, CYP10020, or CYP10285) and/or a recombinant gene encoding a squalene synthase.

It is also comprised within the invention that the recombinant host may be modified in order to reduce glucanase activity, in particular glucanase activity, which may result in deglucosylation of mogrosides. Thus, the recombinant host may for example be modified to reduce of even abolish exo-1,3-beta-Glucanase activity. In embodiments of the invention when the recombinant host is yeast, this may be accomplished by deletion of the EXG1 gene and/or of the EXG2 gene, both of which are encoding an exo-1,3-beta-Glucanase.

The term "recombinant gene" refers to a gene or DNA sequence that is introduced into a recipient host, regardless of whether the same or a similar gene or DNA sequence may already be present in such a host. The term "heterologous nucleic acid" refers to a nucleic acid that is introduced into a recipient host, wherein said host does not endogenously comprise said nucleic acid. "Introduced," or "augmented" in this context, is known in the art to mean introduced or augmented by the hand of man. Thus, a recombinant gene may be a DNA sequence from another species, or may be a DNA sequence that originated from or is present in the same species, but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA.

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene. In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. Such sequences may then also be considered heterologous nucleic acids. In addition, stably transformed exogenous nucleic acids typically are integrated at positions other than the position where the native sequence is found.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned at further distance, for example as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements. One or more genes can be combined in a recombinant nucleic acid construct in "modules" useful for a discrete aspect of mogroside production. Combining a plurality of genes in a module, particularly a polycistronic module, facilitates the use of the module in a variety of species. In addition to genes useful for mogroside production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). Nucleic acids may also be optimized to a GC-content preferable to a particular host, and/or to reduce the number of repeat sequences. As isolated nucleic acids, these modified sequences can exist as purified molecules and can be incorporated into a vector or a virus for use in constructing modules for recombinant nucleic acid constructs.

A number of prokaryotes and eukaryotes are suitable for use as recombinant hosts with the present invention. Thus, the recombinant host may e.g. be selected from the group consisting of gram-negative bacteria, yeast and fungi. A species and strain selected for use as a mogroside production strain is first analyzed to determine which production genes are endogenous to the strain and which genes are not present. Genes for which an endogenous counterpart is not present in the strain are assembled in one or more recombinant constructs, which are then transformed into the strain in order to supply the missing function(s). Thus, it may be analysed which of steps IIa, IIIa, IVa and V are already performed by the host, and then said host may be modified by introduction of heterologous nucleic acids encoding enzymes catalyzing the remaining steps. Similarly, it may be analysed which of steps IIb, IIIb, IVb and V are already performed by the host, and then said host may be modified by introduction of heterologous nucleic acids encoding enzymes catalyzing the remaining steps. As mentioned before the recombinant host may also be modified to increase levels of oxido-squalene and/or dioxido-squalene.

Exemplary prokaryotic and eukaryotic species useful as recombinant with the present invention are described in more detail below. However, it will be appreciated that other species may be suitable. For example, the recombinant host may be in a genus selected from the group consisting of *Agaricus, Aspergillus, Bacillus, Candida, Corynebacterium Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces* and *Yarrowia*. Exemplary species from such genera useful as recombinant hosts include *Lentinus tigrinus, Laetiporus sulphureus, Phanerochaete chrysosporium, Pichia pastoris, Physcomitrella patens, Rhodoturula glutinis, Rhodoturula mucilaginosa, Phaffia rhodozyma, Xanthophyllomyces dendrorhous, Fusarium fujikuroi/Gibberella fujikuroi, Candida utilis* and *Yarrowia lipolytica*. In some embodiments, a recombinant host may be a microorganism, for example an Ascomycete such as *Gibberella fujikuroi, Kluyveromyces lactis, Schizosaccharomyces pombe, Aspergillus niger*, or *Saccharomyces cerevisiae*. In some embodiments, a recombinant host may be a microorganism for example a prokaryote such as *Escherichia coli, Rhodobacter sphaeroides*, or *Rhodobacter capsulatus*. It will be appreciated that certain microorganisms can be used to screen and test genes of interest in a high throughput manner, while other microorganisms with desired productivity or growth characteristics can be used for large-scale production of mogroside compounds. In particular, food grade microorganisms may be useful for large-scale production purposes.

*Saccharomyces cerevisiae*

As described above the recombinant host may for example be *Saccharomyces cerevisiae. Saccharomyces cerevisiae* is a widely used chassis organism in synthetic biology, and can be used as the recombinant microorganism platform. There are libraries of mutants, plasmids, detailed computer models of metabolism and other information available for *S. cerevisiae*, allowing for rational design of various modules to enhance product yield. Methods are known for making recombinant microorganisms. The VG4 strain of *S. cerevisiae* from Brochado et al. 2010 (Microb Cell Fact. 9:84) may be particularly useful. VG4 has the genotype of pdc1Δgdh1Δ↑GDH2. Another very useful strain of *S. cerevisiae* is BY4742 described herein below in Example 9, or the yeast strain described in Kirby, J et al in FEBS Journal 275 (2008) 1852-1859.

*Aspergillus* Spp.

The recombinant host may also be a *Aspergillus* species such as *A. oryzae, A. niger* and *A. sojae. Aspergillus* spp, such as the aforementioned are widely used microorganisms in food production, and can also be used as the recombinant microorganism platform. Nucleotide sequences are available for genomes of *A. nidulans, A. fumigatus, A. oryzae, A. clavatus, A. flavus, A. niger*, and *A. terreus*, allowing rational design and modification of endogenous pathways to enhance flux and increase product yield. Any of these may be used recombinant hosts. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for the production of food ingredients.

*Escherichia coli*

The recombinant host may also be *Escherichia coli*, which is another widely used platform organism in synthetic biology. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Rhodobacter* Spp.

The recombinant host may also be *Rhodobacter*. Similar to *E. coli*, there are libraries of mutants available as well as suitable plasmid vectors, allowing for rational design of various modules to enhance product yield. Methods similar to those described above for *E. coli* can be used to make recombinant *Rhodobacter* microorganisms.

*Physcomitrella* Spp.

The recombinant host may also be *Physcomitrella* mosses. *Physcomitrella* mosses, when grown in suspension culture, have characteristics similar to yeast or other fungal cultures. This genera is becoming an important type of cell for production of plant secondary metabolites, which can be difficult to produce in other types of cells.

Step Ia—Enhancing Levels of Oxido-Squalene

As described herein above the methods of the invention may comprise a step of enhancing the levels of oxido-squalene. This is in particular relevant in methods comprising step IIa, wherein step IIa is performed in vivo. Step Ia may in particular be performed by modifying the recombinant host to be used with the methods in a manner enhancing the levels of oxido-squalene in said recombinant host. The invention also relates to recombinant hosts modified to enhance the levels of oxido-squalene.

Figure 3:
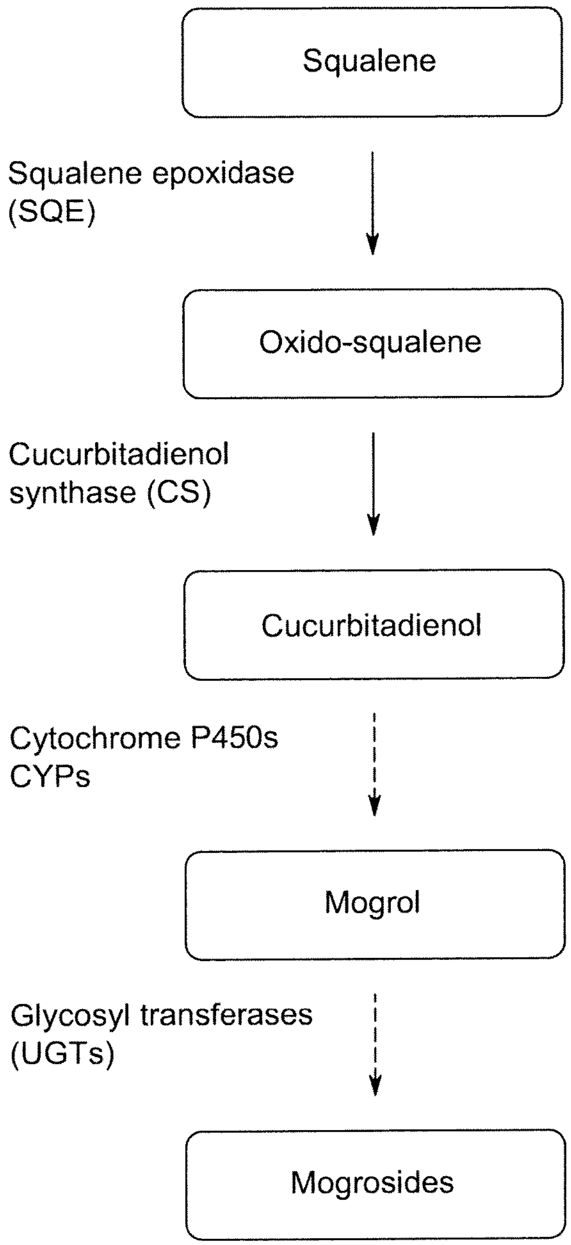
FIG. 3 is a schematic of the production of mogrol glycosides (mogrosides) from squalene.
Figure 3:
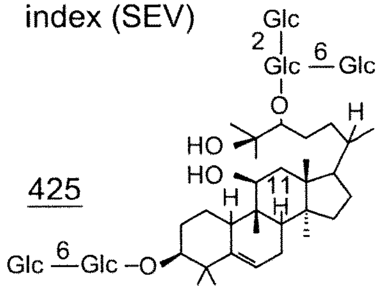
Figure 3:
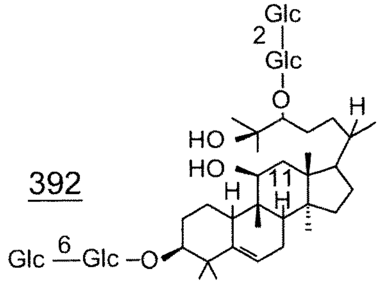
Figure 3:
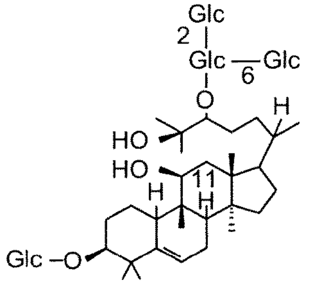
Figure 3:
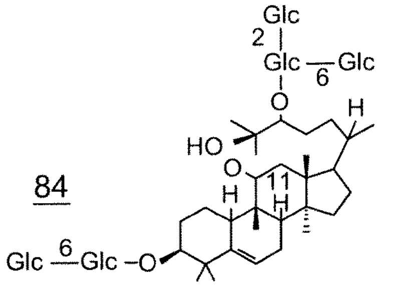

Thus, the methods may also comprise one or more steps leading to formation of oxido-squalene, in particular to the formation of 2,3-oxido-squalene. Said steps are preferably performed prior to step IIa described below, or simultaneously herewith. FIG. 3 provides a schematic of the pathway from squalene to mogrosides.

One step in the production of oxido-squalene may be production of squalene from farnesyl pyrophosphate. One enzyme that catalyzes the production of squalene from farnesyl pyrophosphate is squalene synthase (also referred to as squalene synthase). Said squalene synthase may be any enzyme classified under EC 2.5.1.21. The reaction is typically thought to proceed using NADPH as a cosubstrate. Accordingly, the method may comprise a step of production of squalene from farnesyl pyrophosphate catalyzed by a squalene synthase in the presence of NADPH. In embodiments of the invention wherein the methods are performed in vivo, the recombinant host may thus comprise a heterologous nucleic acid encoding a squalene synthase. Some recombinant hosts may comprise an endogenous squalene synthase in which case the endogenous enzyme may suffice. Endogenous squalene production pathways exist in yeast metabolism, and accordingly, if the recombinant host is yeast, then said step may be endogenous to the recombinant host.

The squalene synthase may be any useful squalene synthase. For example the squalene synthase may be squalene synthase from *Gynostemma pentaphyllum* (protein accession number C4P9M2), another cucurbitaceae family plant. The squalene synthase may also be selected from the the groups consisting of squalene synthase of *Arabidopsis thaliana* (protein accession number C4P9M3), *Brassica napus, Citrus macrophylla, Euphorbia tirucalli* (protein accession number B9WZW7), *Glycine max, Glycyrrhiza glabra* (protein accession number Q42760, Q42761), *Glycrrhiza uralensis* (protein accession number D6QX40, D6QX41, D6QX42, D6QX43, D6QX44, D6QX45, D6QX47, D6QX39, D6QX55, D6QX38, D6QX53, D6QX37, D6QX35, B5AID5, B5AID4, B5AID3, C7EDD0, C6KE07, C6KE08, C7EDC9), *Lotus japonicas* (protein accession number Q84LE3), *Medicago truncatula* (protein accession number Q8GSL6), *Pisum sativum, Ricinus communis* (protein accession number B9RHC3), and *Prunus mume* and functional homologues of any of the aforementioned sharing at least at least 70%, such as at least 80%, for example at least 90%, such as at least 95%, for example at least 98% sequence identity therewith. Increased copy numbers, heterologous nucleic acids encoding squalene synthase, or increased expression of the native squalene synthase may improve levels of mogrosides produced in a recombinant host.

Another step in the production of oxido-squalene may be production of oxido-squalene from squalene. One enzyme that catalyzes the production of oxido-squalene from squalene is squalene epoxidase (also referred to as squalene monoxygenase). Said squalene epoxidase may be any enzyme classified under EC 1.4.99.7. The reaction is typically thought to proceed using NADPH as a cosubstrate. Accordingly, the method may comprise a step of production of oxido-squalene from squalene catalyzed by a squalene epoxidase in the presence of NADPH. In embodiments of the invention wherein the methods are performed in vivo, the recombinant host may thus comprise a heterologous nucleic acid encoding a squalene epoxidase. Some recombinant hosts may comprise an endogenous squalene epoxidase, in which case the endogenous enzyme may suffice. Endogenous oxido-squalene production pathways exist in yeast metabolism, and accordingly, if the recombinant host is yeast, then said step may be endogenous to the recombinant host. However, in order to enhance the level of oxido-squalene it may never-the-less be advantageous to express addition squalene epoxidase.

The squalene epoxidase may be any useful squalene epoxidase. The squalene epoxidase may for example be squalene epoxidase from *Gynostemma pentaphyllum* (protein accession number C4P9M2), a cucurbitaceae family plant. The squalene epoxidase may also be selected from the group consisting of squalene epoxidase of *Arabidopsis thaliana* (protein accession number Q9SM02, O65403, O65402, O65404, O81000, or Q9T064), *Brassica napus* (protein accession number O65727, O65726), *Euphorbia tirucalli* (protein accession number A7VJN1), *Medicago truncatula* (protein accession number Q8GSM8, Q8GSM9), *Pisum sativum*, and *Ricinus communis* (protein accession number B9R6V0, B9S7W5, B9S6Y2, B9T0Y3, B9S7T0, B9SX91) and functional homologues of any of the aforementioned sharing at least 70%, such as at least 80%, for example at least 90%, such as at least 95%, for example at least 98% sequence identity therewith. Increased copy numbers, heterologous nucleic acids encoding squalene epoxidase, or increased expression of the native squalene epoxidase may improve levels of mogrosides produced in a recombinant host.

The squalene epoxidase may also be the product of the ERG1 gene of *S. cerevisiae*. Thus, the squalene epoxidase may be a polypeptide of SEQ ID NO:54 or a functional homologues thereof sharing at least 70%, such as at least 80%, for example at least 90%, such as at least 95%, for example at least 98% sequence identity therewith.

In one embodiment the recombinant host comprises a heterologous nucleic acid encoding a squalene epoxidase operably linked to sequence directing high expression of said squalene epoxidase in said host cell. Thus, the squalene epoxidase may be endogenous to the recombinant host, but the expression level may be increased by additional copies of nucleic acids encoding the squalene epoxidase and/or by use of stronger promoters.

Oxido-squalene serves as a substrate for production of lanosterol. Thus, in one embodiment the level of oxido-squalene may be increased by reducing the activity of lanosterol synthase. In recombinant hosts expressing an endogenous lanosterol synthase, this may be achieved by substituting the endogenous promoter directed expression of lanosterol synthase with a weaker promoter directing expression of a lower level of lanosterol synthase. In yeast the ERG7 gene encodes lanosterol synthase. Thus, when the recombinant host is yeast, then the promoter of the ERG7 gene may be substituted for another promoter, which directs a level of expression, which is lower than the endogenous expression level of ERG7. The lanosterol synthase may thus be the product of the ERG7 gene of *S. cerevisiae*, the sequence of which is provided herein as SEQ ID NO:55 or a functional homologues thereof sharing at least 70%, such as at least 80%, for example at least 90%, such as at least 95%, for example at least 98% sequence identity therewith.

Examples of useful weak promoters include the methionine-repressible promoter of the MET3 gene or the CUP1 cupper inducible promoter. Non-limiting examples of how to reduce the activity of lanosterol synthase are described in Example 9 herein below or in Kirby et al., 2008 (vide supra) both of which are incorporated by reference herein. The sequence of *S. cerevisiae* lanosterol synthase is provided as SEQ ID NO:55. Thus, when the recombinant host is *S. cerevisiae*, then it is preferred that the polypeptide of SEQ ID NO:55 is expressed at a lower level than the level of said polypeptide in wild type *S. cerevisiae*. Similarly, when the recombinant host expresses a polypeptide similar to the polypeptide of SEQ ID NO:55 (e.g. at least 70% identical to SEQ ID NO:55), then it is preferred that said polypeptide at least 70% identical to SEQ ID NO:55 is expressed at a lower level than the level of said polypeptide in the wild type host.

In addition, expression of a truncated form of the enzyme 3-hydroxy-3-methylglutaryl-CoA reductase (tHMG1) may also lead enhanced levels of oxido-squalene. A useful truncated form of yeast HMG reductase (tHMG1) is described in Donald et al., 1997, Appl. Environ. Microbiol. 63, 3341-3344.

Step Ib—Enhancing Levels of Dioxido-Squalene

As described herein above the methods of the invention may comprise a step of enhancing the levels of dioxido-squalene. This is in particular relevant in methods comprising step IIb, wherein step IIb is performed in vivo. Step Ib may in particular be performed by modifying the recombinant host to be used with the methods in a manner enhancing the levels of dioxido-squalene in said recombinant host. The invention also relates to recombinant hosts modified to enhance the levels of dioxido-squalene.

Thus, the methods may also comprise one or more steps leading to enhanced levels of dioxido-squalene. Said steps are preferably performed prior to step IIb described below, or simultaneously herewith.

The present invention describes that the levels of dioxido-squalene in particular may be enhanced by high expression of a squalene epoxidase. Said squalene epoxidase may be any of the squalene epoxidase described herein above in the section "Step Ia—Enhancing levels of oxido-squalene". In particular, the squalene epoxidase may be the product of the ERG1 gene of *S. cerevisiae*. Thus, the squalene epoxidase may be a polypeptide of SEQ ID NO:54 or a functional homologues thereof sharing at least 70%, such as at least 80%, for example at least 90%, such as at least 95%, for example at least 98% sequence identity therewith. High expression level may be achieved by introducing a heterologous nucleic acid encoding a squalene epoxidase into the host cell operably linked to sequence directing high expression of said squalene epoxidase in said host cell. Thus, the squalene epoxidase may be endogenous to the recombinant host, but the expression level may be increased by additional copies of nucleic acids encoding the squalene epoxidase and/or by use of stronger promoters.

The levels of dioxido-squalene may also be enhanced by reducing the activity of lanosterol synthase. The activity of lanosterol synthase may be reduced by any of the methods described herein above in the section "Step Ia—Enhancing levels of oxido-squalene".

The levels of dioxido-squalene may also be enhanced by expression of a truncated form of the enzyme 3-hydroxy-3-methylglutaryl-CoA reductase (tHMG1) may also lead enhanced levels of oxido-squalene. A useful truncated form of yeast HMG reductase (tHMG1) is described in Donald et al., 1997, Appl. Environ. Microbiol. 63, 3341-3344.

Step IIa—Oxido-squalene→cucurbitadienol

As described herein above the methods of the invention may comprise a step of producing cucurbitadienol from oxido-squalene, and in particular from 2,3-oxido-squalene using an enzyme or mixture of enzymes capable of catalysing conversion of oxido-squalene to form cucurbitadienol. The invention also relates to recombinant hosts comprising a heterologous nucleic acid encoding an enzyme capable of catalysing conversion of oxido-squalene to cucurbitadienol.

The step may be performed in vitro by incubating a composition comprising oxido-squalene with said enzyme or a mixture of enzymes capable of catalyzing conversion of oxido-squalene to form cucurbitadienol.

The step may also be performed in vivo in a recombinant host comprising heterologous nucleic acid(s) encoding an enzyme or a mixture of enzymes capable of catalyzing conversion of oxido-squalene to form cucurbitadienol. Said recombinant host may be capable of producing oxido-squalene, for example because the recombinant host expresses one or more enzymes of the oxido-squalene biosynthesis pathway. Alternatively, oxido-squalene may be provided to said recombinant host for example in the cultivation medium.

Said enzyme or mixture of enzyme capable of catalyzing conversion of oxido-squalene to form cucurbitadienol preferably comprises or consists of a cucurbitadienol synthase.

Said cucurbitadienol synthase may be any useful cucurbitadienol synthase, for example a cucurbitadienol synthase, which has been classified as an oxidosqualene cyclase, such as the oxidosqualene cyclase described by Shibuya, *Tetrahedron*, Vol 60: pp. 6995-7003 (2004).

The amino acid sequence of a cucurbitadienol synthase from *Cucurbita pepo* is provided herein as SEQ ID NO:1 and also is provided in GenBank under Protein Accession No. BAD34645.1. In one embodiment of the invention the cucurbitadienol synthase is a polypeptide of SEQ ID NO:1 or a functional homologue thereof sharing at least 70%, such as at least 80%, for example at least 90%, such as at least 95%, for example at least 98% sequence identity therewith.

As described in Example 5, the cucurbitadienol synthase from monk fruit was identified and the sequence of the C-terminal portion of the polypeptide determined. The amino acid sequence of the C-terminal portion of the monk fruit polypeptide is provided herein as SEQ ID NO:2. SEQ ID NO:2 is 97.5% identical to residues 515 to 764 of the *C. pepo* polypeptide set forth in SEQ ID NO:1. Thus, in one embodiment of the invention the cucurbitadienol synthase is a polypeptide comprising the amino acid sequence set forth in SEQ ID NO:2.

In a preferred embodiment the cucurbitadienol synthase is the polypeptide of SEQ ID NO:43 or a functional homologue thereof sharing at least 70%, such as at least 80%, for example at least 90%, such as at least 95%, for example at least 98% sequence identity therewith.

Other homologous proteins can be found of similar length and having approximately 70% homology or higher to SEQ ID NO:1. Such homologs include the polypeptides from *Lotus japonicas* (BAE53431), *Populus trichocarpa* (XP_002310905), *Actaea racemosa* (ADC84219), *Betula platyphylla* (BAB83085), *Glycyrrhiza glabra* (BAA76902), *Vitis vinifera* (XP_002264289), *Centella asiatica* (AAS01524), *Panax ginseng* (BAA33460), and *Betula platyphylla* (BAB83086). The cucurbitadienol synthase may be any of the aforementioned or a functional homologue thereof sharing at least 70%, such as at least 80%, for example at least 90%, such as at least 95%, for example at least 98% sequence identity therewith.

Step IIb—Dioxido-squalene→24,25 epoxy cucurbitadienol

As described herein above the methods of the invention may comprise a step of producing 24,25 epoxy cucurbitadienol from dioxido-squalene using an enzyme or mixture of enzymes capable of catalysing conversion of oxido-squalene to form cucurbitadienol. The invention also relates to recombinant hosts comprising a heterologous nucleic acid encoding an enzyme capable of catalysing conversion of dioxido-squalene to 24,25 epoxy cucurbitadienol.

The step may be performed in vitro by incubating a composition comprising dioxido-squalene with said enzyme or a mixture of enzymes capable of catalyzing conversion of dioxido-squalene to form 24,25 epoxy cucurbitadienol.

The step may also be performed in vivo in a recombinant host comprising heterologous nucleic acid(s) encoding an enzyme or a mixture of enzymes capable of catalyzing conversion of dioxido-squalene to 24,25 epoxy cucurbitadienol. Said recombinant host may be capable of producing dioxido-squalene, for example because the recombinant host expresses one or more enzymes of the dioxido-squalene biosynthesis pathway. However, it is preferred that said recombinant host has been modified to enhance levels of dioxido-squalene in any of the manners described herein above in the section "Step Ib Enhancing levels of dioxidosqualene". Alternatively, dioxido-squalene may be provided to said recombinant host for example in the cultivation medium.

Said enzyme or mixture of enzyme capable of catalyzing conversion of dioxido-squalene to 24,25 epoxy cucurbitadienol preferably comprises or consists of a cucurbitadienol synthase.

Said cucurbitadienol synthase may be any useful cucurbitadienol synthase, for example a cucurbitadienol synthase, which has been classified as an oxidosqualene cyclase, such as the oxidosqualene cyclase described by Shibuya, *Tetrahedron*, Vol 60: pp. 6995-7003 (2004). In one embodiment of the invention the cucurbitadienol synthase is a polypeptide of SEQ ID NO:1 or a functional homologue thereof sharing at least 70%, such as at least 80%, for example at least 90%, such as at least 95%, for example at least 98% sequence identity therewith.

In a preferred embodiment the cucurbitadienol synthase is the polypeptide of SEQ ID NO:43 or a functional homologue thereof sharing at least 70%, such as at least 80%, for example at least 90%, such as at least 95%, for example at least 98% sequence identity therewith.

Other homologous proteins can be found of similar length and having approximately 70% homology or higher to SEQ ID NO:1. Such homologs include the polypeptides from *Lotus japonicas* (BAE53431), *Populus trichocarpa* (XP_002310905), *Actaea racemosa* (ADC84219), *Betula platyphylla* (BAB83085), *Glycyrrhiza glabra* (BAA76902), *Vitis vinifera* (XP_002264289), *Centella asiatica* (AAS01524), *Panax ginseng* (BAA33460), and *Betula platyphylla* (BAB83086). The cucurbitadienol synthase may be any of the aforementioned or a functional homologue thereof sharing at least 70%, such as at least 80%, for example at least 90%, such as at least 95%, for example at least 98% sequence identity therewith.

Step IIIa—Cucurbitadienol→11-hydroxy-cucurbitadienol

As described herein above the methods of the invention may comprise a step of producing 11-hydroxy-cucurbitadienol from cucurbitadienol using an enzyme or a mixture of enzymes capable of catalysing hydroxylation of cucurbitadienol to form 11-hydroxy-cucurbitadienol.

The step may be performed in vitro by incubating a composition comprising cucurbitadienol with said enzyme capable of catalyzing hydroxylation of cucurbitadienol to form 11-hydroxy-cucurbitadienol.

The step may also be performed in vivo in a recombinant host comprising heterologous nucleic acid(s) encoding an enzyme capable of catalyzing hydroxylation of cucurbitadienol to form 11-hydroxy-cucurbitadienol. Said recombinant host may be capable of producing cucurbitadienol, for example because the recombinant host expresses one or more enzymes of the cucurbitadienol biosynthesis pathway. Alternatively, cucurbitadienol may be provided to said recombinant host for example in the cultivation medium.

Said enzyme capable of catalyzing hydroxylation of cucurbitadienol to form 11-hydroxy-cucurbitadienol preferably is selected from the group of cytochrome P450 enzymes.

As indicated in Example 7, one or more of CYP533, CYP937, CYP1798, CYP1994, CYP2048, CYP2740, CYP3404, CYP3968, CYP4112, CYP4149, CYP4491, CYP5491, CYP6479, CYP7604, CYP8224, CYP8728, CYP10020, and CYP10285 (encoded by SEQ ID NOs: 3-20, respectively) can be used to produce mogrol. eYAC technology can be used to assess activity of the cytochrome P450 enzymes as set forth in Example 8. Alternatively, an in vitro reaction can be used to assess the activity. Thus, in one embodiment of the invention at least one cytochrome P450 enzyme is selected from the group consisting of polypeptides encoding by the nucleic acid sequence SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or a or a functional homologue thereof sharing at least 70%, such as at least 80%, for example at least 90%, such as at least 95%, for example at least 98% sequence identity therewith at the amino acid level.

In a preferred embodiment of the invention the enzyme capable of catalyzing hydroxylation of cucurbitadienol to form 11-hydroxy-cucurbitadienol is CYP5491. Thus, the enzyme catalyzing hydroxylation of cucurbitadienol to form 11-hydroxy-cucurbitadienol may be a polypeptide of SEQ ID NO:44 or a functional homologue thereof sharing at least 70%, such as at least 80%, for example at least 90%, such as at least 95%, for example at least 98% sequence identity therewith.

In one embodiment of the invention this step may be aided by at least one CYP activator. This step of the methods of the invention may thus comprise use of a cytochrome P450 enzyme as described above in combination with at least one CYP activator. Thus, the recombinant host may in addition to containing heterologous nucleic acids encoding the cytochrome P450 enzymes described herein above also contain a heterologous nucleic acid encoding a CYP activator. Said CYP activator may be any useful CYP activator, for example it may be a polypeptide be a polypeptide of SEQ ID NO:46 or a functional homologue thereof sharing at least 70%, such as at least 80%, for example at least 90%, such as at least 95%, for example at least 98% sequence identity therewith.

Step IIIb 24,25 epoxy cucurbitadienol→11-hydroxy-24,25 epoxy cucurbitadienol As described herein above the methods of the invention may comprise a step of producing 11-hydroxy-24,25 epoxy cucurbitadienol from 24,25 epoxy cucurbitadienol using an enzyme capable of catalysing hydroxylation of 24,25 epoxy cucurbitadienol to form 11-hydroxy-24,25 epoxy cucurbitadienol.

The step may be performed in vitro by incubating a composition comprising 24,25 epoxy cucurbitadienol with said enzyme capable of catalyzing hydroxylation of 24,25 epoxy cucurbitadienol to form 11-hydroxy-24,25 epoxy cucurbitadienol.

The step may also be performed in vivo in a recombinant host comprising heterologous nucleic acid(s) encoding an enzyme capable of catalyzing hydroxylation of 24,25 epoxy cucurbitadienol to form 11-hydroxy-24,25 epoxy cucurbitadienol. Said recombinant host may be capable of producing 24,25 epoxy cucurbitadienol, for example because the recombinant host expresses one or more enzymes of the 24,25 epoxy cucurbitadienol biosynthesis pathway, e.g. cucurbitadienol synthase. Alternatively, 24,25 epoxy cucurbitadienol may be provided to said recombinant host for example in the cultivation medium.

Said enzyme capable of catalyzing hydroxylation of cucurbitadienol to form 11-hydroxy-cucurbitadienol preferably is selected from the group of cytochrome P450 enzymes.

In a preferred embodiment of the invention the enzyme capable of catalyzing hydroxylation of 24,25 epoxy cucurbitadienol to form 11-hydroxy-24,25 epoxy cucurbitadienol is CYP5491. Thus, the enzyme catalyzing hydroxylation of 24,25 epoxy cucurbitadienol to form 11-hydroxy-24,25 epoxy cucurbitadienol may be a polypeptide of SEQ ID NO:44 or a functional homologue thereof sharing at least 70%, such as at least 80%, for example at least 90%, such as at least 95%, for example at least 98% sequence identity therewith.

In one embodiment of the invention this step may be aided by at least one CYP activator. This step of the methods of the invention may thus comprise use of a cytochrome P450 enzyme as described above in combination with at least one CYP activator. Thus, the recombinant host may in addition to containing heterologous nucleic acids encoding the cytochrome P450 enzymes described herein above also contain a heterologous nucleic acid encoding a CYP activator. Said CYP activator may be any useful CYP activator, for example it may be a polypeptide be a polypeptide of SEQ ID NO:46 or a functional homologue thereof sharing at least 70%, such as at least 80%, for example at least 90%, such as at least 95%, for example at least 98% sequence identity therewith.

Step IVa—11-hydroxy-cucurbitadienol→mogrol

As described herein above the methods of the invention may comprise a step of producing mogrol from 11-hydroxy-cucurbitadienol using an enzyme or a mixture of enzymes capable of catalysing conversion of 11-hydroxy-cucurbitadienol to form mogrol.

The step may be performed in vitro by incubating a composition comprising 11-hydroxy-cucurbitadienol with said enzyme or mixture of enzymes capable of catalyzing conversion of 11-hydroxy-cucurbitadienol to form mogrol.

The step may also be performed in vivo in a recombinant host comprising heterologous nucleic acid(s) encoding an enzyme or mixture of enzymes capable of catalyzing conversion of 11-hydroxy-cucurbitadienol to form mogrol. Said recombinant host may be capable of producing 11-hydroxy-cucurbitadienol, for example because the recombinant host expresses one or more enzymes of the 11-hydroxy-cucurbitadienol biosynthesis pathway. Alternatively, 11-hydroxy-cucurbitadienol may be provided to said recombinant host for example in the cultivation medium.

Said enzyme or mixture of enzymes capable of catalyzing conversion of 11-hydroxy-cucurbitadienol to form mogrol preferably comprises one or more enzymes with together has CYP450 activity and epoxide hydrolase activity.

Enzymes with CYP450 include for example the polypeptides encoding by the nucleic acid sequence SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or a or a functional homologue thereof sharing at least 70%, such as at least 80%, for example at least 90%, such as at least 95%, for example at least 98% sequence identity therewith at the amino acid level.

Another enzyme with CYP450 activity is CYP5491. Thus, the enzyme with CYP450 activity may be a polypeptide of SEQ ID NO:44 or a functional homologue thereof sharing at least 70%, such as at least 80%, for example at least 90%, such as at least 95%, for example at least 98% sequence identity therewith.

In one embodiment of the invention this step may be aided by at least one CYP activator. This step of the methods of the invention may thus comprise use of a cytochrome P450 enzyme as described above in combination with at least one CYP activator. Thus, the recombinant host may in addition to containing heterologous nucleic acids encoding the cytochrome P450 enzymes described herein above also contain a heterologous nucleic acid encoding a CYP activator. Said CYP activator may be any useful CYP activator, for example it may be a polypeptide be a polypeptide of SEQ ID NO:46 or a functional homologue thereof sharing at least 70%, such as at least 80%, for example at least 90%, such as at least 95%, for example at least 98% sequence identity therewith.

The enzyme having epoxide hydrolase activity may for example be an enzyme classified under EC 3.3._._. Said epoxide hydrolase preferably catalyses the following reaction:

epoxide+$H_2O$→glycol

Examples of enzymes with epoxide hydrolase activity includes *S. grosvenorii* Epoxide hydrolase 1 and *S. grosvenorii* Epoxide hydrolase 2. Thus, the enzyme with epoxide hydrolase activity may be selected from the group consisting of polypeptides of SEQ ID NO:38, SEQ ID NO:40 and functional homologue thereof sharing at least 70%, such as at least 80%, for example at least 90%, such as at least 95%, for example at least 98% sequence identity therewith.

Step IVa—11-hydroxy-24,25 epoxy cucurbitadienol→mogrol

As described herein above the methods of the invention may comprise a step of producing mogrol from 11-hydroxy-24,25 epoxy cucurbitadienol using an enzyme or a mixture of enzymes capable of catalysing conversion of 11-hydroxy-24,25 epoxy cucurbitadienol to form mogrol.

The step may be performed in vitro by incubating a composition comprising 11-hydroxy-24,25 epoxy cucurbitadienol with said enzyme or mixture of enzymes capable of catalyzing conversion of 11-hydroxy-24,25 epoxy cucurbitadienol to form mogrol.

The step may also be performed in vivo in a recombinant host comprising heterologous nucleic acid(s) encoding an enzyme or mixture of enzymes capable of catalyzing conversion of 11-hydroxy-24,25 epoxy cucurbitadienol to form mogrol. Said recombinant host may be capable of producing 11-hydroxy-24,25 epoxy cucurbitadienol, for example because the recombinant host expresses one or more enzymes of the 11-hydroxy-24,25 epoxy cucurbitadienol biosynthesis pathway.

Alternatively, 11-hydroxy-24,25 epoxy cucurbitadienol may be provided to said recombinant host for example in the cultivation medium.

Said enzyme or mixture of enzymes capable of catalyzing conversion of 11-hydroxy-24,25 epoxy cucurbitadienol to form mogrol preferably comprises an enzyme with epoxide hydrolase activity.

The enzyme having epoxide hydrolase activity may for example be an enzyme classified under EC 3.3._._. Said epoxide hydrolase preferably catalyses the following reaction:

epoxide+$H_2O$→glycol

Examples of enzymes with epoxide hydrolase activity includes *S. grosvenorii* Epoxide hydrolase 1 and *S. grosvenorii* Epoxide hydrolase 2. Thus, the enzyme with epoxide hydrolase activity may be selected from the group consisting of polypeptides of SEQ ID NO:38, SEQ ID NO:40 and functional homologue thereof sharing at least 70%, such as at least 80%, for example at least 90%, such as at least 95%, for example at least 98% sequence identity therewith.

Step V—Mogrol→Mogroside

The methods of invention may involve a step of glycosylating mogrol to form mogroside. This step is in general accomplished with the aid of an enzyme or a mixture of enzymes capable of catalyzing glycosylation of mogrol and/or of glycosylated mogrol.

The mogroside may be any of the mogrosides described herein below in the section "Mogrosides".

Step V may be performed in vitro by incubating a composition comprising mogrol with said enzyme or a mixture of enzymes capable of catalyzing glycosylation of mogrol. The step may also be divided into separate steps, wherein each step involves glycosylation of mogrol or glycosylated mogrol.

The step may also be performed in vivo in a recombinant host comprising heterologous nucleic acid(s) encoding an enzyme or a mixture of enzymes capable of catalyzing glycosylation of mogrol and optionally also of glycosylated mogrol. Said recombinant host may be capable of producing mogrol, for example because the recombinant host expresses one or more enzymes of the mogrol biosynthesis pathway. Alternatively, mogrol may be provided to said recombinant host for example in the cultivation medium.

Said enzyme or mixture of enzyme capable of catalyzing glycosylation of mogrol preferably comprises a Uridine-5'-diphospho (UDP) dependent glucosyltransferase (UGT). In particular, it is preferred that step V comprises use of a UGT.

Thus, step V may include incubating mogrol with at least one Uridine-5'-diphospho (UDP) dependent glucosyltransferase (UGT) to produce a mogroside compound (e.g., mogroside I E1, mogroside I A1, mogroside II E, mogroside III A2, mogroside III, mogroside IV, mogroside V, or a mogroside compound glycosylated at C24-OH).

The UGT may for example be selected from the group consisting of 73C3, 73C6, 85C2, 73C5, and 73E1. The UGT may also be UGT73C3 of SEQ ID NO:21, UGT73C6 of SEQ ID NO:23, UGT85C2 of SEQ ID NO:25, UGT73C5 of SEQ ID NO: 22, UGT73E1 of SEQ ID NO:24 or a functional homologue of any of the aforementioned sharing at least 70%, such as at least 80%, for example at least 90%, such as at least 95%, for example at least 98% sequence identity therewith.

The UGT may also be selected from the group consisting of UGT98, UGT1495, UGT1817, UGT5914, UGT8468 and UGT10391. The UGT may also be UGT98 of SEQ ID NO:53, UGT1495 encoded by SEQ ID NO:27, UGT1817 encoded by SEQ ID NO:28, UGT5914 encoded by SEQ ID NO:30, UGT8468 encoded by SEQ ID NO:31 and UGT10391 encoded by SEQ ID NO:32 or a functional homologue of any of the aforementioned sharing at least 70%, such as at least 80%, for example at least 90%, such as at least 95%, for example at least 98% sequence identity therewith at the amino acid level.

When the methods are performed in vitro the UGTs can for example be recombinantly produced or can be in a cell lysate of a recombinant host. This document also features a method of producing a mogroside compound, wherein the method includes contacting mogrol with a cell lysate prepared from a recombinant host expressing a UGT to produce a mogroside compound (e.g., mogroside I E1, mogroside I A1, mogroside II E, mogroside III A2, mogroside III, mogroside IV, mogroside V, or a mogroside compound glycosylated at C24-OH). The UGT can be any of the above mentioned UGTs.

This document provides methods and materials for glycosylating mogrol using one or more Uridine-5'-diphospho (UDP) dependent glucosyltransferases (UGTs). As indicated below, at least five UGTs have been identified that glycosylate the aglycone mogrol. Each of the UGTs identified herein are in glycosyltransferase family I. Thus, in one preferred embodiment the UGT is a UGT in glycosyltransferase family I.

Figure 4:
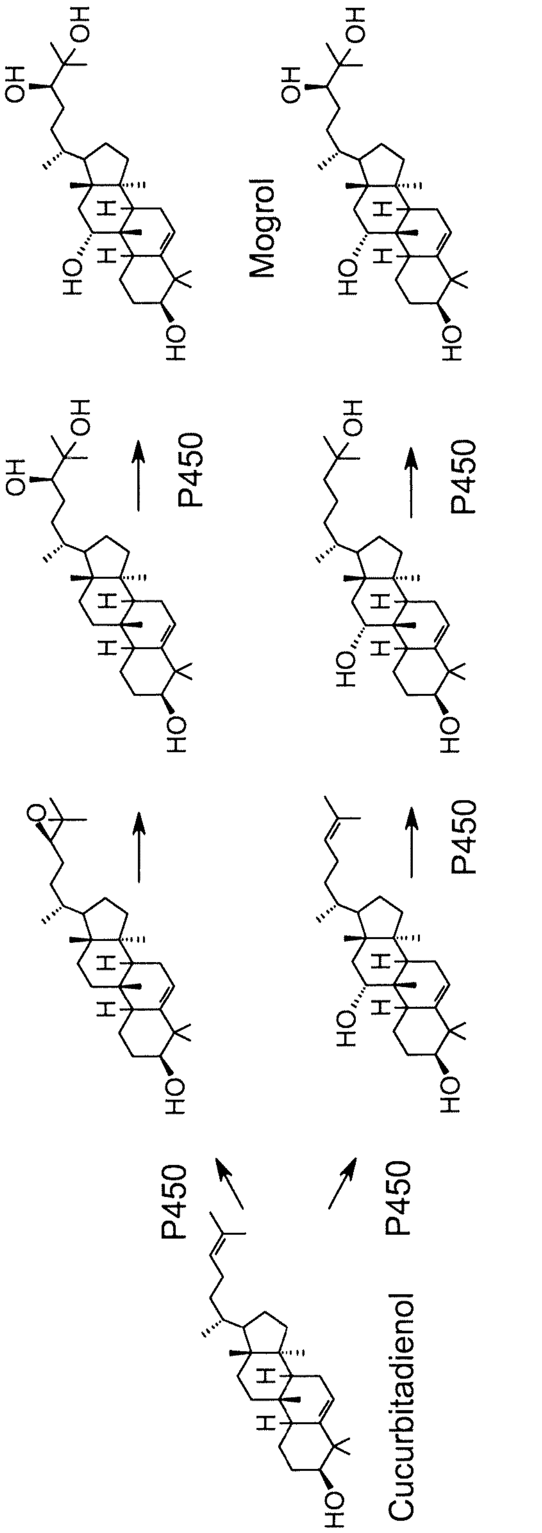
FIG. 4 is a schematic of the pathway proposed herein by the inventors (top) and published (bottom) of a P450 pathway for formation of mogrol from cucurbitadienol.
Figure 5:
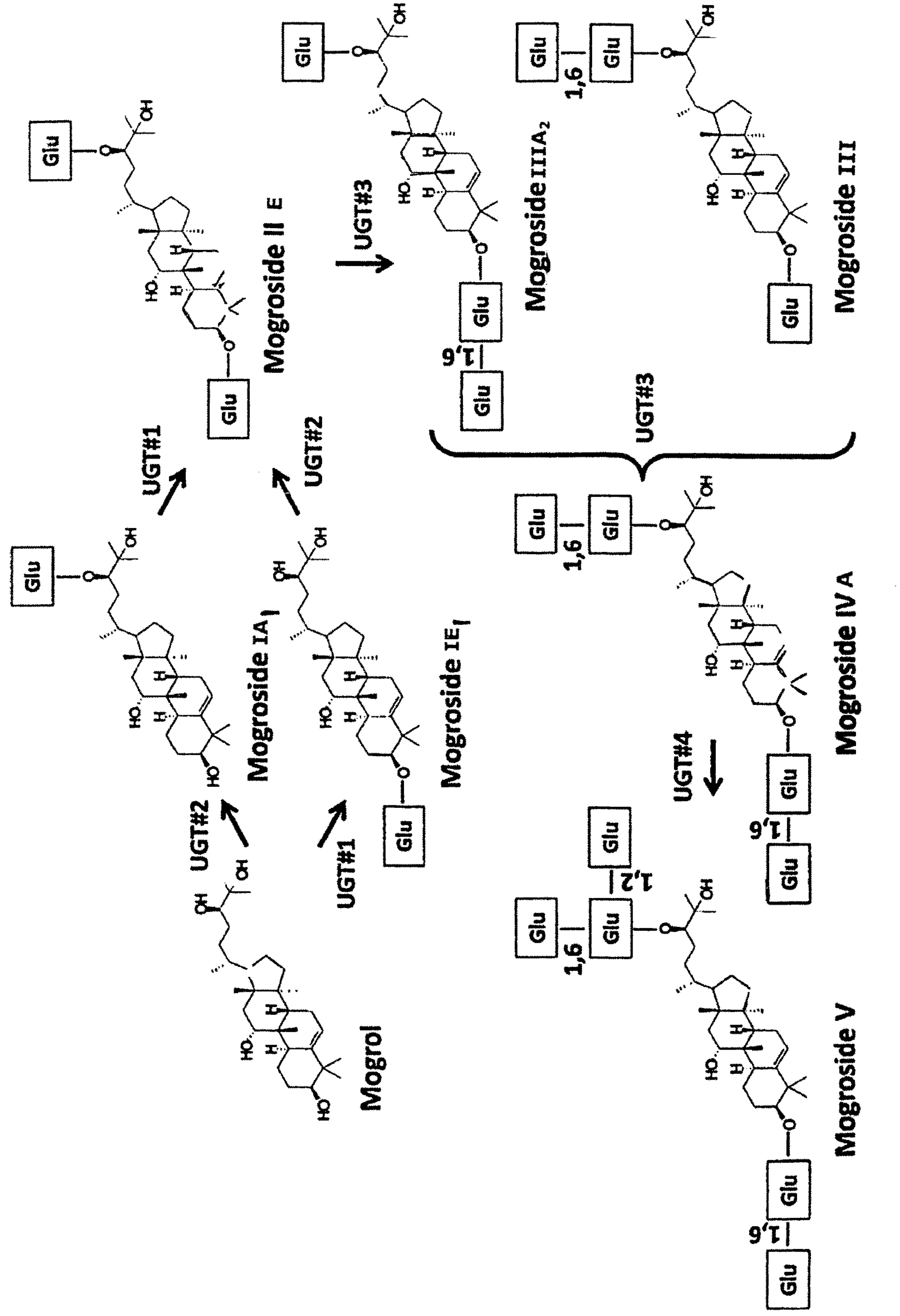
FIG. 5 is a depiction of the biosynthesis of mogroside I E1, mogroside I A1, mogroside II E, mogroside III A2, mogroside III, mogroside IV, and mogroside V from mogrol using UGTs.

UGTs 73C3, 73C6, 85C2 and 73E1 are capable of catalyzing glycosylation at the C24-OH position of mogrol or mogroside (UGT#2 in FIG. 4). Accordingly, in methods of the invention wherein the mogroside to be produced comprises a glycosylation at the C24-OH position then at least one UGT may be UGT73C3 of SEQ ID NO:21, UGT73C6 of SEQ ID NO:23, UGT85C2 of SEQ ID NO:25 or UGT73E1 of SEQ ID NO:24 or a or a functional homologue of any of the aforementioned sharing at least 70%, such as at least 80%, for example at least 90%, such as at least 95%, for example at least 98% sequence identity therewith.

UGT73C5 is capable of catalyzing glycosylation at both the C3-OH of mogrol and mogroside (UGT#1 in FIG. 4) and C24-OH position (UGT#2). Accordingly, in methods of the invention wherein the mogroside to be produced comprises a glycosylation at the C24-OH position and/or a glycosylation at the C3-OH position, then at least one UGT may be UGT73C5 of SEQ ID NO:22 or a functional homologue of any of the aforementioned sharing at least 70%, such as at least 80%, for example at least 90%, such as at least 95%, for example at least 98% sequence identity therewith.

UGTs 73C3, 73C5, and 73C6 are from *Arabidopsis thaliana*. UGT 73E1 and 85C2 are from *Stevia rebaudiana*. The amino acid sequences of UGTs 73C3, 73C5, 73C6, 73E1, and 85C2 are provided herein as SEQ ID NOs: 21-25, respectively). Thus, UGTs 73C3, 73C6, 85C2, or 73E1 can be used to produce mogroside I E1 from mogrol, and UGT73C5 can be used to produce mogroside I A1 from mogrol. Mogroside I E1 can be converted to mogroside II E using UGT73C5. Mogroside I A1 can be converted to mogroside II E using UGTs 73C3, 73C6, 85C2, or 73E1.

In one preferred embodiment of the invention at least one UGT is UGT1576 of SEQ ID NO:48 or a functional homologue of any of the aforementioned sharing at least 70%, such as at least 80%, for example at least 90%, such as at least 95%, for example at least 98% sequence identity therewith. This is in particular the case in embodiments of the invention, wherein the mogroside to be produced comprises a glycosylation at the C24-OH position, because UGT1576 is a glycosyltransferase with mogrol 24-OH UDP-glycosyltransferase activity.

In one preferred embodiment of the invention at least one UGT is UGT98 of SEQ ID NO:53 or a functional homologue thereof sharing at least 70%, such as at least 80%, for example at least 90%, such as at least 95%, for example at least 98% sequence identity therewith. This is in particular the case in embodiments of the invention, wherein the mogroside to be produced comprises a 1,2 glucosylation and a 1,6 glycosylation of the glucose at position C-24 to form mogroside III A1.

In one preferred embodiment of the invention at least one UGT is UGT SK98 of SEQ ID NO:50 or a functional homologue of any of the aforementioned sharing at least 70%, such as at least 80%, for example at least 90%, such as at least 95%, for example at least 98% sequence identity therewith. This is in particular the case in embodiments of the invention, wherein the mogroside to be produced comprise a 1,2 glycosylation of the glucose at position C-24 to form mogroside II A.

As shown in FIG. 4, three enzymatic glycosylations convert mogroside II E into mogroside V or 11-Oxo-mogroside V. First, two glucoses are attached with 1,6-bonds to the two glucose molecules already present in mogroside II E. Second, another glucose is added to the C24-bound glucose, with a 1,2 bond. Mogroside IV is an intermediate in which the 1,2-bound glucose is missing at the C24-bound glucose. In siamenoside this glucose is present, but the 1,6-bound glucose at the C3-bound glucose is missing. 11-Oxo-mogroside V is identical to mogroside V, only the 11-OH is oxidized. One or more of the following UGTs can be used to convert mogroside II E to mogroside IV, mogroside V, 11-oxo-mogroside V, and siamenoside I: UGT98, UGT1495, UGT1817, UGT3494, UGT5914, UGT8468, UGT10391, UGT11789, UGT11999, UGT13679 and UGT15423 (SEQ ID NOs: 26-36, respectively) or functional. For example, one or more of UGT98, UGT1495, UGT1817, UGT5914, UGT8468 and UGT10391 can be used to produce mogroside IV, mogroside V, 11-oxo-mogroside V, or siamenoside I.

In one embodiment of the invention step V comprises one or more of the following steps:

a) Glucosylation of mogrol at C24 to form mogroside I A1
b) 1,6 glucosylation of the C24 bound glucose of mogroside I A1 to form mogroside II A
c) 1,2 glucosylation of the C24 bound glucose of mogroside IIa to form mogroside III A1
d) Glucosylation of mogroside III A1 at the C3 to form siamenoside 1
e) 1,6 glucosylation of the C3 bound glucose of siamenoside 1 to form mogroside V These steps may each be catalyzed by a UGT capable of catalyzing said step. Thus, for example step a) may for example be catalyzed by UGT1576 of SEQ ID NO:48 or a functional homologue of any of the aforementioned sharing at least 70%, such as at least 80%, for example at least 90%, such as at least 95%, for example at least 98% sequence identity therewith. Step b) may for example be catalyzed by UGT98 of SEQ ID NO:53 or a functional homologue thereof sharing at least 70%, such as at least 80%, for example at least 90%, such as at least 95%, for example at least 98% sequence identity therewith. Step c) may for example be catalyzed by UGT98 of SEQ ID NO:53, UGT SK98 of SEQ ID NO:50 or a functional homologue of any of the aforementioned sharing at least 70%, such as at least 80%, for example at least 90%, such as at least 95%, for example at least 98% sequence identity therewith. Step d) may for example be catalyzed by UGT73C5 of SEQ ID NO:22 or a functional homologue thereof sharing at least 70%, such as at least 80%, for example at least 90%, such as at least 95%, for example at least 98% sequence identity therewith. Step e) may for example be catalyzed by UGT of the UGT91 family. For example step e9 may be catalyzed by UGT98 of SEQ ID NO:53 or a functional homologue thereof sharing at least 70%, such as at least 80%, for example at least 90%, such as at least 95%, for example at least 98% sequence identity therewith.

Activity of the UGTs can be assessed in vitro. For example, an in vitro UGT reaction mixture can include UGT enzyme, 4× Tris buffer, substrate (250 μM), UDP glucose (750 μM) and 1% alkaline phosphatase, in a total reaction volume of about 50 μl. The reactions can be performed in sterilized 96 well plates, and incubated overnight at 30° C. After the incubation, 25 μL of DMSO can be added to each reaction and the reaction plates centrifuged for 5 min. Samples can be taken from each well, filtered, and then analyzed via LC-MS.

Production of Polypeptides

As described herein above, the methods of the invention may be performed in in vitro or in vivo. In embodiments of the invention where the methods are performed in vitro one or more of the enzymes to be used in the methods may be prepared using any conventional method for producing polypeptides.

Thus, enzymes, such as synthases, hydrolyases, UGTs and CYP450 polypeptides described herein can be produced using any method. For example, enzymes, such as synthases, hydrolyases, UGT or CYP450 polypeptides can be produced by chemical synthesis. Alternatively, enzymes, such as synthases, hydrolyases, UGT or CYP450 polypeptides described herein can be produced by standard recombinant technology using heterologous expression vectors encoding enzymes, such as synthases, hydrolyases, UGT or CYP450 polypeptides. Expression vectors can be introduced into host cells (e.g., by transformation or transfection) for expression of the encoded polypeptide, which then optionally can be purified or partly purified. Crude extracts comprising the enzymes may also be used with the methods of the invention. Expression systems that can be used for small or large scale production of enzymes, such as synthases, hydrolyases, UGT and CYP450 polypeptides include, without limitation, microorganisms such as bacteria (e.g., *E. coli* and *B. subtilis*) transformed with recombinant DNA, such as bacteriophage DNA, plasmid DNA, or cosmid DNA expression vectors containing the nucleic acid molecules described herein, or yeast (e.g., *S. cerevisiae* or *S. pombe*) transformed with recombinant yeast expression vectors containing the nucleic acid molecules described herein. Useful expression systems also include insect cell systems infected with recombinant virus expression vectors (e.g., baculovirus) containing the nucleic acid molecules described herein, or plant cell systems infected with recombinant virus expression vectors (e.g., tobacco mosaic virus) or transformed with recombinant plasmid expression vectors (e.g., Ti plasmid) containing the nucleic acid molecules described herein. Enzymes, such as synthases, hydrolyases, UGT or CYP450 polypeptides also can be produced using mammalian expression system harboring recombinant expression constructs containing promoters derived from the genome of mammalian cells (e.g., the metallothionein promoter) or from mammalian viruses (e.g., the adenovirus late promoter and the cytomegalovirus promoter), along with the nucleic acids described herein. Enzymes, such as synthases, hydrolyases, UGT or CYP450 polypeptides to be used with the methods of the invention may have an N-terminal or C-terminal tag as discussed below.

This document also provides isolated nucleic acids encoding the enzymes to be used in each of steps Ia, Ib, IIa, IIb, IIIa, IIIb, Iva, IVb and V described herein above, such as synthases, hydrolyases, UGT or CYP450 polypeptides. An "isolated nucleic acid" refers to a nucleic acid that is separated from other nucleic acid molecules that are present in a genome, including nucleic acids that normally flank one or both sides of the nucleic acid in a genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome. Thus, the isolated nucleic acid may be cDNA encoding any of the enzymes to be used with the methods of the invention.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., any paramyxovirus, retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

In some embodiments, a nucleic acid sequence encoding an enzyme to be used with the methods of the invention, such as synthases, hydrolyases, UGT or CYP450 polypeptides can include a tag sequence that encodes a "tag" designed to facilitate subsequent manipulation (e.g., to facilitate purification or detection), secretion, or localization of the encoded polypeptide. Tag sequences can be inserted in the nucleic acid sequence encoding the enzyme, such that the encoded tag is located at either the carboxyl or amino terminus of the enzyme. Non-limiting examples of encoded tags include green fluorescent protein (GFP), glutathione S transferase (GST), HIS tag, and Flag™ tag (Kodak, New Haven, Conn.). Other examples of tags include a chloroplast transit peptide, a mitochondrial transit peptide, an amyloplast peptide, signal peptide, or a secretion tag.

Functional Homologs

Functional homologs of the polypeptides described above are also suitable for use in the methods and recombinant hosts described herein. A functional homolog is a polypeptide that has sequence similarity to a reference polypeptide, and that carries out one or more of the biochemical or physiological function(s) of the reference polypeptide. Thus, functional homologues of the enzymes described herein are polypeptides that have sequence similarity to the reference enzyme, and which are capable of catalyzing the same step or part of a step of the methods of the invention as the reference enzyme.

In general it is preferred that functional homologues share at least some degree of sequence identity with the reference polypeptide. Thus, it is preferred that a functional homologues of any of the polypeptides described herein shares at least 70%, such as at least 75%, such as at least 80%, for example at least 85%, for example at least 90%, such as at least 95%, for example at least 98% sequence identity therewith.

Amino acid sequence identity requires identical amino acid sequences between two aligned sequences. Thus, a candidate sequence sharing 80% amino acid identity with a reference sequence, requires that, following alignment, 80% of the amino acids in the candidate sequence are identical to the corresponding amino acids in the reference sequence. Identity according to the present invention is determined by aid of computer analysis, such as, without limitations, the ClustalW computer alignment program (Higgins D., Thompson J., Gibson T., Thompson J. D., Higgins D. G., Gibson T. J., 1994. CLUSTAL W: improving the sensitivity of progressive multiple sequence alignment through sequence weighting, position-specific gap penalties and weight matrix choice. Nucleic Acids Res. 22:4673-4680), and the default parameters suggested therein. The ClustalW software is available from as a ClustalW WWW Service at the European Bioinformatics Institute http://www.ebi.ac.uk/clustalw. Using this program with its default settings, the mature (bioactive) part of a query and a reference polypeptide are aligned. The number of fully conserved residues are counted and divided by the length of the reference polypeptide. The sequence identity is determined over the entire length of the reference polypeptide A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional homologues of an enzyme to be used with the methods of the invention, such as synthases, hydrolyases, UGT or CYP450 polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide:polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of enzymes to be used with the methods of the invention, such as synthases, hydrolyases, UGT or CYP450 polypeptides. Sequence analysis can involve BLAST, Reciprocal BLAST, or PSI-BLAST analysis of nonredundant databases using one of the sequences identified herein encoding an enzyme to be used with the methods of the invention, such as synthases, hydrolyases, UGT amino acid sequence as the reference sequence. Amino acid sequence is, in some instances, deduced from the nucleotide sequence. Those polypeptides in the database that have greater than 40% sequence identity are candidates for further evaluation for suitability as synthases, hydrolyases, UGT or CYP450 polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in enzymes to be used with the methods of the invention, such as synthases, hydrolyases, UGT or CYP450 polypeptides, e.g., conserved functional domains. Conserved regions can be identified by locating a region within the primary amino acid sequence of a polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., Nucl. Acids Res., 26:320-322 (1998); Sonnhammer et al., Proteins, 28:405-420 (1997); and Bateman et al., Nucl. Acids Res., 27:260-262 (1999). Conserved regions also can be determined by aligning sequences of the same or related polypeptides from closely related species. Closely related species preferably are from the same family. In some embodiments, alignment of sequences from two different species is adequate. Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity. Sequence identity can be determined as set forth above.

Mogrosides

The present invention relates to methods for producing mogrosides and materials for use in such methods. The term "mogroside" as used herein refers to mogrol glycosylated at one or more positions. In particular, mogrosides according to the present invention may be mogrol glycosylated with one or more glucose residues at the positions 3 and/or 24. It is less preferred that mogrosides are glycosylated at the 11 and 25 positions. Mogrol is a compound of formula I provided below, wherein both $R_1$ and $R_2$ are —H.

It is preferred that the mogroside is a compound of the following formula I:

(I)

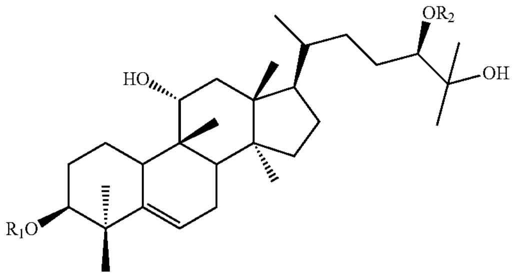

wherein $R_1$ and $R_2$ independently are —H, mono-glucoside, di-glucoside, tri-glucoside, and at least one of $R_1$ and $R_2$ is not —H.

In particular the mogroside may be one the mogrosides described in Table 1 herein below.

TABLE 1

Mogrosides of formula I

| Name | $R_1$ | $R_2$ |
|---|---|---|
| mogroside V | Glc6-Glc- | Glc6-Glc2-Glc |
| siamenoside I | Glc- | Glc6-Glc2-Glc- |
| mogroside IV | Glc6-Glc- | Glc2-Glc- |
| mogroside IV A | Glc6-Glc- | Glc6-Glc- |
| mogroside III | Glc- | Glc6-Glc- |
| mogroside III A1 | H | Glc6-Glc2-Glc- |
| mogroside III A2 | Glc6-Glc- | Glc- |
| mogroside III E | Glc- | Glc2-Glc- |
| mogroside II A | H | Glc2-Glc- |
| mogroside II A1 | H | Glc6-Glc- |
| mogroside II A2 | Glc6-Glc- | H |
| mogroside II E | Glc- | Glc- |
| mogroside I A1 | H | Glc- |
| mogroside I E1 | Glc- | H |

Glc = glucose

Mogroside I A1 may sometimes be referred to as mogroside Ib. Mogroside I E1 may sometimes be referred to as mogroside Ia. Mogroside II E may sometimes be referred to as mogroside II. Mogroside III A2 may sometimes be referred to as mogroside IIIa. Mogroside III may sometimes be referred to as mogroside IIIb. This alternative nomenclature is for example used in U.S. Ser. No. 61/733,220.

The invention will be further described in the following examples, which do not limit the scope of the invention described in the claims.

SEQUENCE LISTING

| | |
|---|---|
| SEQ ID NO: 1 | Amino acid sequence of *C. pepo* cucurbitadienol synthase |
| SEQ ID NO: 2 | Amino acid sequence of C-terminal portion of *Siraitia grosvenorii* cucurbitadienol synthase |
| SEQ ID NO: 3 | DNA sequence encoding CYP533 (nucleotide sequence of CYP533 gene) |
| SEQ ID NO: 4 | DNA sequence encoding CYP937 (nucleotide sequence of CYP937 gene) |
| SEQ ID NO: 5 | DNA sequence encoding CYP1798 (nucleotide sequence of CYP1798 gene) |
| SEQ ID NO: 6 | DNA sequence encoding CYP1994 (nucleotide sequence of CYP1994 gene) |
| SEQ ID NO: 7 | DNA sequence encoding CYP2048 (nucleotide sequence of CYP2048 gene) |
| SEQ ID NO: 8 | DNA sequence encoding CYP2740 (nucleotide sequence of CYP2740 gene) |
| SEQ ID NO: 9 | DNA sequence encoding CYP3404 (nucleotide sequence of CYP3404 gene) |
| SEQ ID NO: 10 | DNA sequence encoding CYP3968 (nucleotide sequence of CYP3968 gene) |
| SEQ ID NO: 11 | DNA sequence encoding CYP4112 (nucleotide sequence of CYP4112 gene) |
| SEQ ID NO: 12 | DNA sequence encoding CYP4149 (nucleotide sequence of CYP4149 gene) |
| SEQ ID NO: 13 | DNA sequence encoding CYP4491 (nucleotide sequence of CYP4491 gene) |
| SEQ ID NO: 14 | DNA sequence encoding CYP5491 (nucleotide sequence of CYP5491 gene) |
| SEQ ID NO: 15 | DNA sequence encoding CYP6479 (nucleotide sequence of CYP6479 gene) |
| SEQ ID NO: 16 | DNA sequence encoding CYP7604 (nucleotide sequence of CYP7604 gene) |
| SEQ ID NO: 17 | DNA sequence encoding CYP8224 (nucleotide sequence of CYP8224 gene) |
| SEQ ID NO: 18 | DNA sequence encoding CYP8728 (nucleotide sequence of CYP8728 gene) |
| SEQ ID NO: 19 | DNA sequence encoding CYP10020 (nucleotide sequence of CYP10020 gene) |
| SEQ ID NO: 20 | DNA sequence encoding CYP10285 (nucleotide sequence of CYP10285 gene) |
| SEQ ID NO: 21 | Amino acid sequence of UGT73C3 |
| SEQ ID NO: 22 | Amino acid sequence of UGT73C5 |
| SEQ ID NO: 23 | Amino acid sequence of UGT73C6 |
| SEQ ID NO: 24 | Amino acid sequence of UGT73E1 |

-continued

| | |
|---|---|
| SEQ ID NO: 25 | Amino acid sequence of UGT85C2 |
| SEQ ID NO: 26 | Nucleotide sequence encoding *Siraitia grosvenorii* UGT98 |
| SEQ ID NO: 27 | Nucleotide sequence encoding *Siraitia grosvenorii* UGT1495 |
| SEQ ID NO: 28 | Nucleotide sequence encoding *Siraitia grosvenorii* UGT1817 |
| SEQ ID NO: 29 | Partial gene sequence - nucleotide sequence encoding fragment of *Siraitia grosvenorii* UGT3494 |
| SEQ ID NO: 30 | Nucleotide sequence encoding *Siraitia grosvenorii* UGT5914 |
| SEQ ID NO: 31 | Nucleotide sequence encoding *Siraitia grosvenorii* UGT8468 |
| SEQ ID NO: 32 | Nucleotide sequence encoding *Siraitia grosvenorii* UGT10391 |
| SEQ ID NO: 33 | Partial gene sequence - nucleotide sequence encoding fragment of *Siraitia grosvenorii* UGT11789 |
| SEQ ID NO: 34 | Partial gene sequence - nucleotide sequence encoding fragment of *Siraitia grosvenorii* UGT11999 |
| SEQ ID NO: 35 | Partial gene sequence - Nucleotide sequence encoding fragment of *Siraitia grosvenorii* UGT13679 |
| SEQ ID NO: 36 | Partial gene sequence - Nucleotide sequence encoding fragment of *Siraitia grosvenorii* UGT15423 |
| SEQ ID NO: 37 | DNA sequence encoding *S. grosvenorii* Epoxide hydrolase 1 codon optimised for expression in *S. cerevisiae* |
| SEQ ID NO: 38 | Amino acid sequence of *S. grosvenorii* Epoxide hydrolase 1 |
| SEQ ID NO: 39 | DNA sequence encoding *S. grosvenorii* Epoxide hydrolase 2 codon optimised for expression in *S. cerevisiae* |
| SEQ ID NO: 40 | Amino acid sequence of *S. grosvenorii* Epoxide hydrolase 2 |
| SEQ ID NO: 41 | DNA sequence encoding CYP10969 (nucleotide sequence of CYP10969 gene) |
| SEQ ID NO: 42 | DNA sequence encoding *Siraitia grosvenorii* cucurbitadienol synthase codon optimized for expression in *S. cerevisiae* |
| SEQ ID NO: 43 | Amino acid sequence of *Siraitia grosvenorii* cucurbitadienol synthase |
| SEQ ID NO: 44 | Amino acid sequence of *S. grosvenorii* CYP5491 |
| SEQ ID NO: 45 | DNA sequence encoding *S. grosvenorii* CPR4497 |
| SEQ ID NO: 46 | Amino acid sequence of *S. grosvenorii* CPR4497 |
| SEQ ID NO: 47 | DNA sequence encoding *S. grosvenorii* UGT1576 |
| SEQ ID NO: 48 | Amino acid sequence of *S. grosvenorii* UGT1576 |
| SEQ ID NO: 49 | DNA sequence encoding *S. grosvenorii* UGT SK98 |
| SEQ ID NO: 50 | Amino acid sequence of *S. grosvenorii* UGT SK98 |
| SEQ ID NO: 51 | DNA sequence encoding *S. grosvenorii* UGT98 |
| SEQ ID NO: 52 | DNA sequence encoding *S. grosvenorii* UGT98 codon optimised for expression in *S. cerevisiae* |
| SEQ ID NO: 53 | Amino acid sequence of *S. grosvenorii* UGT98 |
| SEQ ID NO: 54 | Amino acid sequence of *S. cerevisiae* squalene epoxidase encoded by the ERG1 gene |
| SEQ ID NO: 55 | Amino acid sequence of *S. cerevisiae* lanosterol synthase encoded by the ERG7 gene |

EXAMPLES

Example 1—Purification of Mogroside V

Mogroside V was purified from commercially available monk fruit extracts (PureLo®, Swanson) as follows. Three bottles of PureLo® (240 grams) were dissolved in water (900 mL), then loaded on a column of HP-20 resin (400 gram resin). The column was washed with water (2.5 liters); then further washed with 20% methanol-water. The product was eluted with methanol. After evaporation of solvents and drying under high vacuum, mogroside V (2.5 grams, ~80% purity, 11-oxomogroside V was the major impurity) was obtained.

Example 2—Enzymatic Synthesis of Mogrol from Mogroside V

Figure 6:
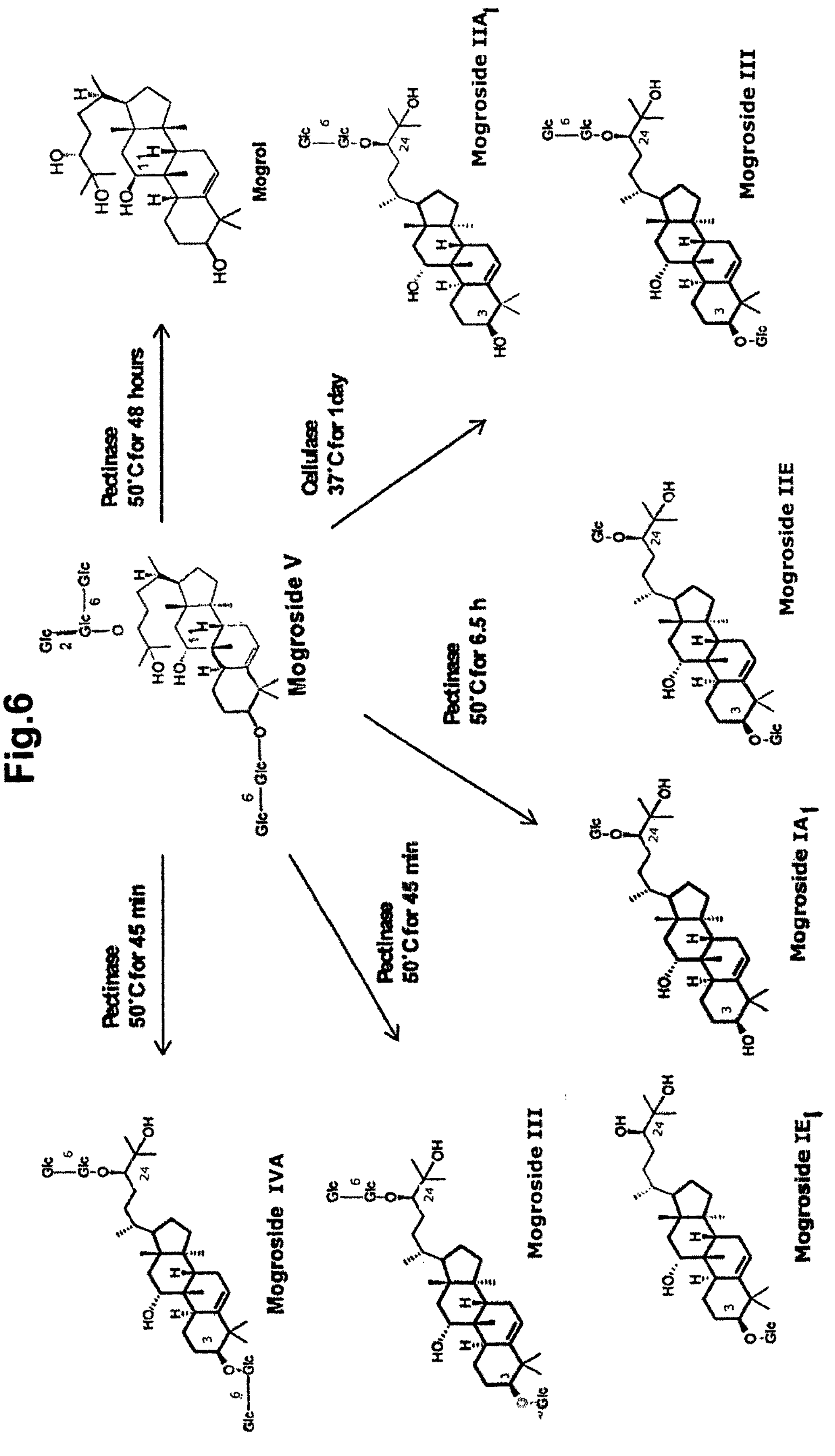
FIG. 6 is a schematic of the products obtained from mogroside V after incubation with a pectinase and/or a cellulase.

Mogroside V (300 mg) was dissolved in 0.1M sodium acetate buffer (pH 4.5, 100 mL), and crude pectinase from *Aspergillus niger* (25 mL, Sigma P2736) was added. The mixture was stirred at 50° C. for 48 hours. The reaction mixture was extracted with ethyl acetate (2×100 ml). The organic extract was dried under vacuum then purified with preparative HPLC. Pure mogrol (40 mg) was obtained and its structure confirmed by NMR and mass spectroscopy. See FIG. 6.

Example 3—Enzymatic Synthesis of Mogrol 3-O-Glucoside (Mogroside I E1) and Mogrol 24-O-Glucoside (Mogroside I A1) from Mogroside V Mogroside V (300 mg) was dissolved in 0.1M sodium acetate buffer (pH 4.5, 100 ml), and crude pectinase from *Aspergillus niger* (25 ml, Sigma P2736) was added. The mixture was stirred at 50° C. for 6.5 hours. The reaction mixture was extracted with ethyl acetate (2×100 ml). The organic extract was dried under vacuum then purified with preparative HPLC. Pure mogroside I E1 (11.0 mg) and mogroside I A1 (8.0 mg) were obtained. Their structures were confirmed by NMR and mass spectroscopy. See FIG. 6.

Example 4—In Vitro UGT Screening and Reactions

In vitro reactions of mogrol with a panel of 230 UGT enzymes were performed and the products were analyzed with LC-MS. The in vitro UGT reaction mixtures included 4× Tris buffer, mogrol (250 μM), UDP-glucose (750 μM) and 1% alkaline phosphatase. Five μl of each partially purified UGT enzyme or crude enzyme extract was added to the reaction, and the reaction volume brought to 50 μl with water. The reactions were incubated overnight at 30° C. and performed in sterilized 96 well plates. After the incubation, 25 μL of DMSO were added into each reaction and the reaction plates were centrifuged for 5 min. Forty μL samples were taken from each well and filtered, and were used for LC-MS analysis. UGTs 73C3, 73C6 and 85C2 were found to convert all the mogrol substrate to mogroside I A1. UGT 73C5 makes both mogroside I E1 and I A1. In the reaction with UGT 20 73E1, although the reaction was not complete, mogroside I A1 was found as the major product, together with a new glycosylated mogrol (neither mogroside I E1 nor I A1; exact mass shown as a mogroside I, presumably caused by a glycosylation event on C11-OH).

Example 5—Identifying the Monk Fruit Cucurbitadienol Synthase

The gene in monk fruit that codes for cucurbitadienol synthase is CirCS, and the partial gene sequence covering 338 of the supposedly 764 amino acids was identified by doing a tBLASTn analysis of the assembled data with a query cucurbitadienol synthase from *Cucurbita pepo* (accession number BAD34645.1, SEQ ID NO:1). The partial CirCS is 97.5% identical to the *C. pepo* gene at the protein level (SEQ ID NO:2; from residues 515 to 764 of SEQ ID NO:1).

Example 6—Identifying Monk Fruit Candidate Genes for P450 Enzymes Catalyzing Formation of Mogrol from Cucurbitadienol A pathway from cucurbitadienol to mogrol has been proposed by Tang et al., BMC Genomics, 12, 343 (2011).

Figure 10A:
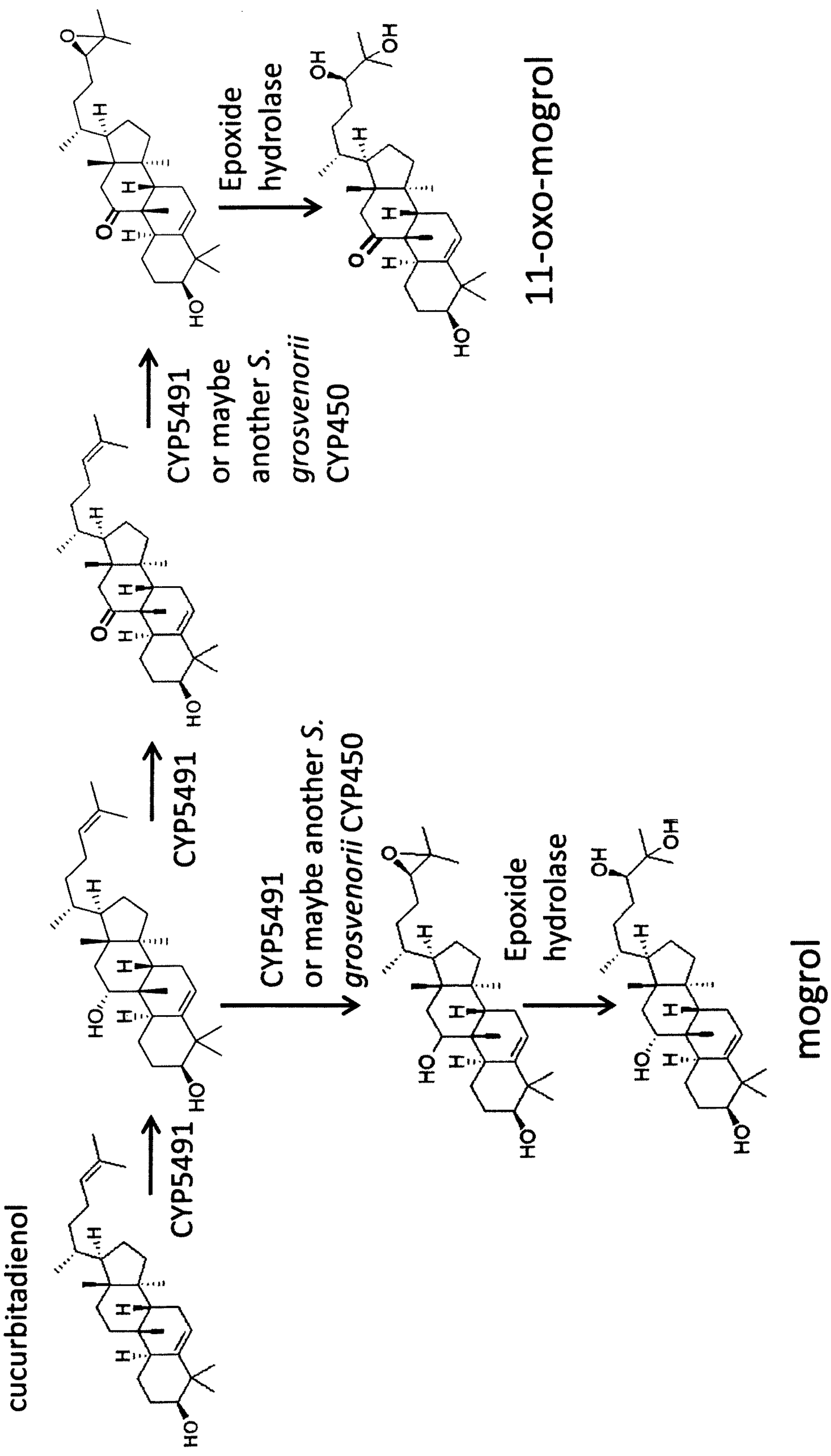
FIG. 10A shows a route from oxido-squalene to mogrol and 11-oxo-mogrol proposed by the present invention.
Figure 10B:
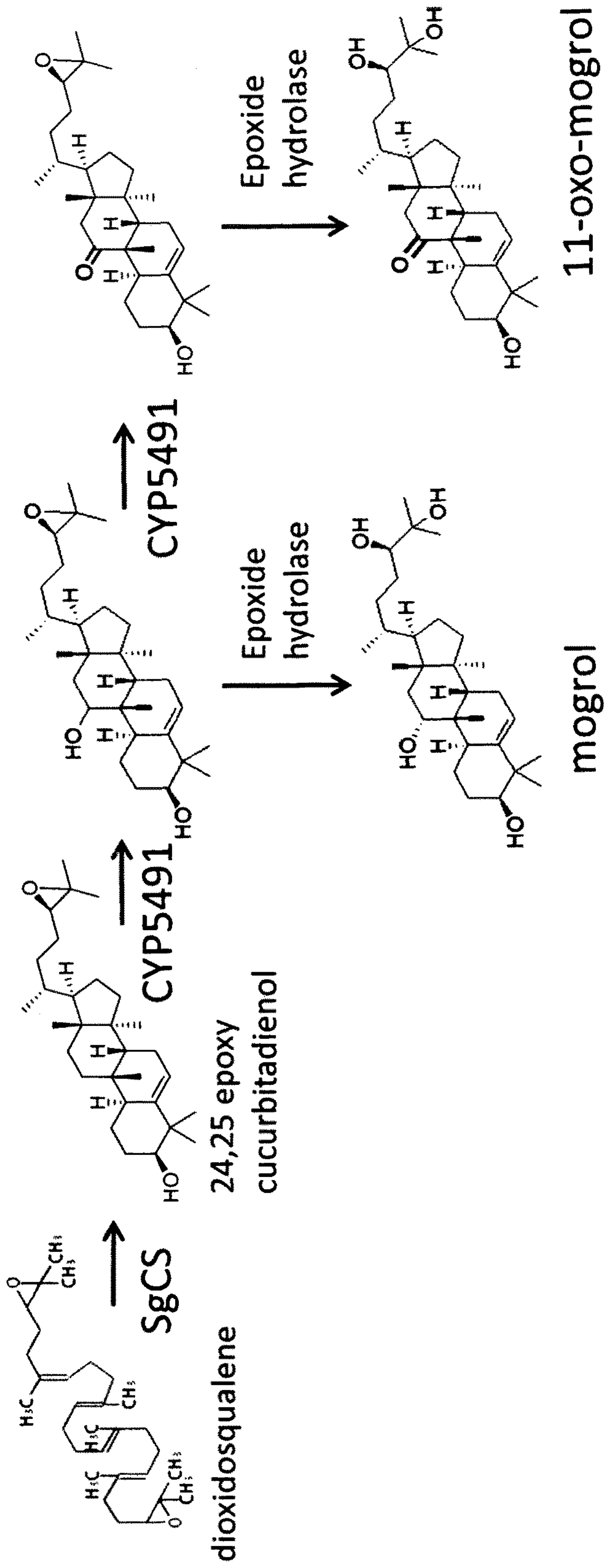
FIG. 10B shows a route from dioxido-squalene to mogrol and 11-oxo-mogrol proposed by the present invention.

The intermediates cucurbitadienol and mogrol exist in the fruit as they have been isolated as minor products. See Ukiya, et al., *J. Agric. Food Chem.* 50, 6710-6715 (2002). Glycoside intermediates exist in both 11-hydroxy and 11-oxo series, and gradually change from mogroside I to mogroside V as fruits ripen, which indicates that the triterpene core is fully oxidized by P450 enzymes before the subsequent glycosylations. According to the scheme proposed by Tang et al., three independent cytochrome P450 enzyme-catalyzed oxidations results in mogrol formation from cucurbitadienol (lower route in FIG. 4). The present inventors have found that the proposed primary reaction is highly unlikely. It is therefore submitted that the route may involve epoxidation by one cytochrome P450 enzyme, followed by a spontaneous or enzyme catalyzed hydration, and another P450 enzyme-catalyzed oxidation (visualized in the upper route in FIG. 4), or the route may comprise similar steps in another order as shown in FIG. 10A. The present inventors also propose another route starting from dioxidosqualene, which is shown in FIG. 10B.

To identify the most likely candidate P450 genes from monk fruit, a BLAST database was made consisting of the polypeptide sequences of the 239 public domain *Arabidopsis thaliana* cytochrome P450 enzymes, representing most known enzyme subfamilies and variations. The sequences were used in a tBLASTn (translated nucleotide database) analysis of the assembled monk fruit transcriptome data to identify all sequences with a homology to any of the database query sequences with an E value of 10E-10 or lower. Seventy-two sequences were identified. Typically, the ability to assemble full or long gene lengths of expressed sequence tags in a transcriptome study means that many sequence tags of the gene in question were present. In the current experiment, this indicates that the gene was highly expressed in the monk fruit tissue and thus has a high probability of being a candidate for one of the two P450 enzymes of interest. Of the 72 sequences, 18 were full length or almost full length. The assembled genes were designated CYP533, CYP937, CYP1798, CYP1994, CYP2048, CYP2740, CYP3404, CYP3968, CYP4112, CYP4149, CYP4491, CYP5491, CYP6479, CYP7604, CYP8224, CYP8728, CYP10020, and CYP10285.

These are candidate genes for two P450 enzymes involved in catalyzing conversion of cucurbitadienol into mogrol. Full length gene sequences were amplified by PCR for the gene contigs CYP533, CYP937, CYP1798, CYP1994, CYP2740, CYP4112, CYP4149, CYP4491, CYP5491, CYP7604, CYP8224, and CYP10285, using monk fruit leaf genomic DNA or root cDNA and sequence overlap extension technology to remove resident intron sequences. The nucleotide sequences of CYP533, CYP937, CYP1798, CYP1994, CYP2048, CYP2740, CYP3404, CYP3968, CYP4112, CYP4149, CYP4491, CYP5491, CYP6479, CYP7604, CYP8224, CYP8728, CYP10020, and CYP10285 are provided as SEQ ID NOs: 3-20, respectively.

Figure 1:
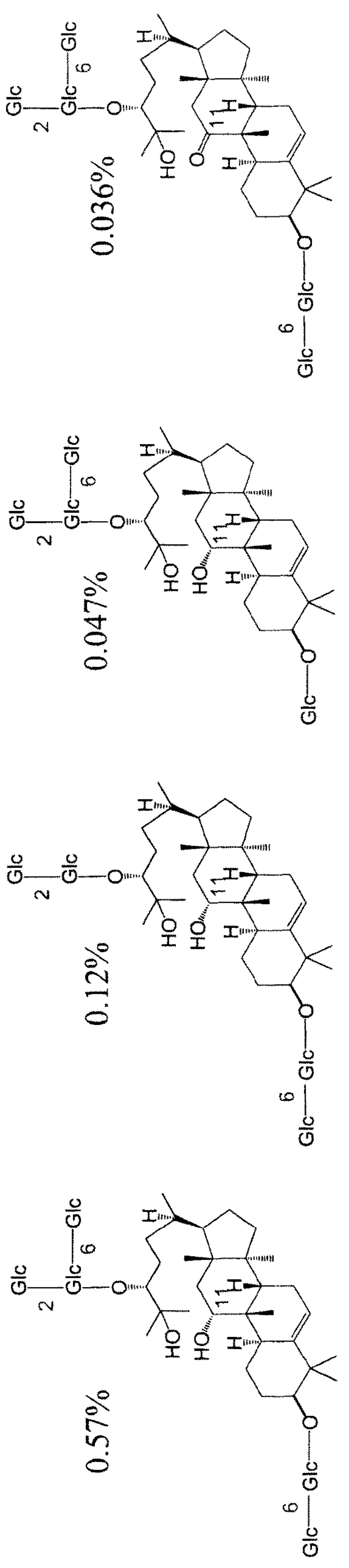
FIG. 1 contains the chemical structure of Mogroside V, Mogroside IV, Siamenoside I, and 11-Oxomogroside V.

Example 7—Identifying Monk Fruit Candidate Genes for Glycosyltransferase Enzymes Catalyzing Formation of Mogroside V, 11-Oxo-Mogroside V, Mogroside IV, Mogrosides III A2 and b and Siamenoside from Mogroside II E Three enzymatic glycosylations are needed to convert mogroside II E into mogroside V or 11-Oxo-mogroside V. Two glucoses are attached with 1,6-bonds to the two glucose molecules already present in mogroside II E. This may be done by one UGT enzyme. Another glucose is added to the C24-bound glucose, with a 1,2 bond. Mogroside IV is an intermediate in which the 1,6-bound glucose is missing at the C24-bound glucose. In siamenoside this glucose is present, but the 1,6-bound glucose at the C3-bound glucose is missing. 11-Oxo-mogroside V is identical to mogroside V, only the 11-OH is oxidized. See, FIG. 1 for the structures of mogroside IV, mogroside V, 11-Oxo-mogroside V, and siamenoside.

To identify all possible UGT genes in the assembled monk fruit transcriptome data, a database was assembled consisting of the polypeptide sequences of glycosyltransferases (UGTs) of all known sub-families, a total of 160 sequences. A tBLASTn analysis was performed between this database and the assembled monk fruit data. UGTs performing di-glycosylation (i.e., attaching a sugar to another sugar which in turn resides on an aglycon) invariably come from Family 1 UGT sub-families 76, 79, 91 or 94 (with the latter three forming the "orthology group 8"). While sub-family 76 enzymes usually make 1,3 bonds, orthology group 8 UGTs always make 1,2 or 1,6 bonds.

Sequences were identified that showed more homology to orthology group 8 enzymes than to any other UGT enzymes or any non-UGT genes. Thus 11 contigs were identified as likely candidates to encode the two glycosyltransferase genes needed to turn mogroside II E into mogroside V: UGT98, UGT1495, UGT1817, UGT3494, UGT5914, UGT8468, UGT10391, UGT11789, UGT11999, UGT13679 and UGT15423 (SEQ ID NOs: 26-36, respectively). Of these we were able to amplify by PCR UGT98, UGT1495, UGT1817, UGT5914, UGT8468 and UGT10391, using monk fruit leaf genomic DNA or root cDNA. The amplified genes were inserted into *E. coli* expression plasmid vectors.

The enzymes are expressed and purified on nickel columns. In vitro reactions of mogroside I A1, I E1 and II E with the panel of 6 purified UGT enzymes are performed and the products analyzed with LC-MS. The in vitro UGT reaction mixtures include 4× Tris buffer, substrate (250 μM), UDP-glucose (750 μM) and 1% alkaline phosphatase. Five μl of each partially purified UGT enzyme are added to the reaction, and the reaction volume brought to 50 μl with water. The reactions are incubated overnight at 30° C. and performed in sterilized 96 well plates. After the incubation, 25 μL of DMSO are added into each reaction and the reaction plates are centrifuged for 5 min. Forty μL samples are taken from each well and filtered, and then analyzed via LC-MS. The UGT catalyzing the 1,6-bond formation as well as the enzyme catalyzing the 1,2-bond formation are identified based on the LC-MS analysis.

Example 8—Using eYAC Technology to Identify the Cytochrome P450 Enzymes Responsible for Turning Cucurbitadienol into Mogrol eYAC gene expression technology was used to identify the active cytochrome P450 enzymes within a collection of candidate genes. The following genes were inserted into "Entry vectors" (a collection of plasmid vectors containing gene promoter and terminator sequences which have different nucleotide sequence but which are all 30 repressible by the addition of the amino acid methionine): the *Cucurbita pepo* cucurbitadienol synthase gene, CYP533 (SEQ ID NO:3), CYP937 (SEQ ID NO:4), CYP1798 (SEQ ID NO:5), CYP1994 (SEQ ID NO:6), CYP2740 (SEQ ID NO:8), CYP4112 (SEQ ID NO:11), CYP4149 (SEQ ID NO:12), CYP4491 (SEQ ID NO:13), CYP5491 (SEQ ID NO:14), CYP7604 (SEQ ID NO:16), CYP8224 (SEQ ID NO:17), and CYP10285 (SEQ ID NO:20), the two cytochrome P450 oxidoreductase (CPR) genes from *Arabidopsis thaliana* (ATR1 and ATR2), a CPR from *Stevia rebaudiana* (CPRS), a CPR isolated from monk fruit, and the glycosyltransferases UGT73C5 (SEQ ID NO: 22) and UGT73C6 (SEQ ID NO:23) from *A. thaliana* and UGT85C2 (SEQ ID NO:25) from *S. rebaudiana*.

The expression cassettes from these 17 plasmids are excised after an AscI+SrfI digestion, purified and then randomly concatenated in ligation reactions to create artificial yeast chromosomes ("eYACs"). From 30 to 200 ug of DNA are prepared from 10 each of the cassette-containing entry vectors and the cassettes are randomly concatenated into eYACs by ligation with T4 ligase in a 3 hour reaction. The success of the concatenation reaction is assessed by the viscosity of the reaction mixture, since concatenated DNA is highly viscous. DNA fragments ("arms") containing a centromere, two telomeres and the LEU2 and TRP1 selection markers are added to the end of the 15 concatenated expression cassettes, thereby creating functional eYACs. The eYACs are transformed into transformation-competent spheroplasts of yeast strain erg7 by zymolyase digestion of the yeast cell wall, followed by treatment with a CaCl2/PEG buffer, making the spheroplasts permeable to large molecules such as eYACs. After transformation, the yeast spheroplasts are embedded in a "noble agar" based solid growth medium, in which regeneration of the cell wall can take place. Colonies appear from 4-8 days after inoculation. The regeneration medium lacks the amino acids leucine and tryptophan, thus selecting for the presence of double-armed eYACs in the yeast cells. One hundred transformants are selected and analyzed for production of mogrosides I E1, I A1 and II E, LC-MS (Liquid Chromatography-coupled Mass Spectrometry (Triple Quadropole)).

Each transformant is re-streaked and tested for yeast strain markers and the genetic presence of both arms of the eYAC, i.e., the LEU2 and TRP1 markers. More than 95% of the transformants has the correct genotype. Each transformant is given a CEY designation number. Initially, 48 CEYs are grown in 50 ml of Synthetic Complete medium (SC) in 100 ml Ehrlenmeyer flasks, without methionine, so as to induce gene expression from the eYACs, and without tryptophan, leucine and histidine, so as to counter-select for loss of eYACs. The cultures have a start density corresponding to an OD600 of 0.25, and they are inoculated for 48 h at 30 C, with slow shaking (150 rpm). After 24 hours, 1 ml supernatant from each culture is collected and subjected to LC-MS analysis. Positive CEYs (i.e., those producing any of the mogrosides assayed for) are subjected to PCR analysis in order to assess which CYP genes are present on the harbored eYAC and thus identifying the mogrol pathway P450 enzymes.

Example 9—Boosting Mogrol Pathway Precursor Availability

The background strain used in this study is the BY4742 strain deleted for the TRP1 gene. This strain is called EFSC301. To increase the availability of oxidosqualene and dioxidosqualene in this laboratory yeast strain, the promoter of the endogenous ERG7 gene was displaced by a PCR fragment consisting of the Nurseothricin marker (NatMX) and the CUP1 cupper inducible promoter. This displacement gives low transcription and thereby low expression of ERG7 when the yeast strain is grown in normal growth medium like Synthetic Complete medium (SC medium). ERG7 encode the lanosterol synthase and lowered expression is known to result in accumulation of oxidosqualene and dioxidosqualene in baker's yeast. Oxidosqualene is generally the precursor of triterpenoids and possibly a precursor of the mogrol pathway. To further increase oxidosqualene and dioxidosqualene availability the squalene epoxidase encoded by ERG1 was overexpressed by a GPD1 promoter from a gene copy integrated into the genome. The sequence of the squalene epoxidase encoded by ERG1 is provided herein as SEQ ID NO:54. Furthermore a truncated copy of the yeast HMG reductase (tHMG1) was expressed from a genomically integrated gene copy, with expression from a GPD1 promoter. The resulting strain is called EFSC3027.

Figure 7:
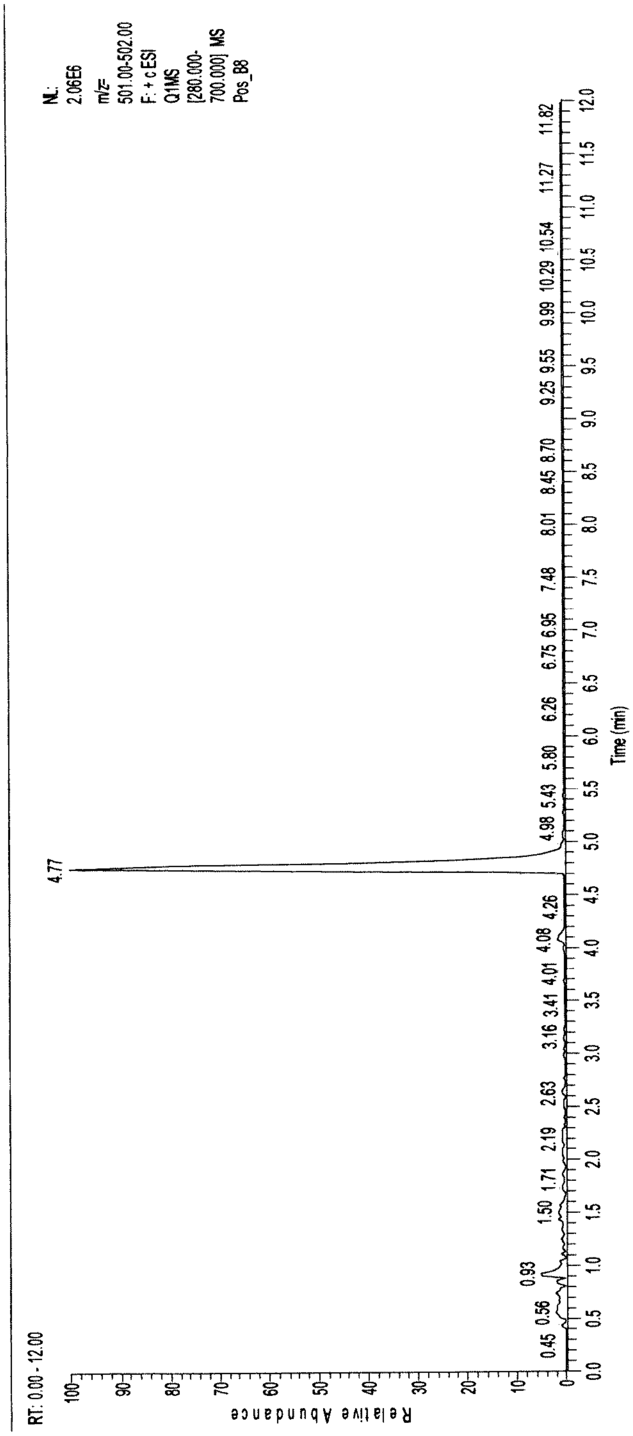
FIG. 7 shows the LC-MS mass peak 501 corresponding to the proton plus Na+ adduct of tetrahydroxysqualene in a sample from yeast strain EFSC3027 transformed with a plasmid expressing *S. grosvenorii* Epoxide hydrolase 2.

The successful boosting of oxidosqualene and dioxidosquale production in the strain EFSC3027 was demonstrated by production of tetrahydroxysqualene when either one of two soluble *S. grosvenorii* epoxide hydrolases was expressed in this strain. One epoxide hydrolase was *S. grosvenorii* Epoxide hydrolase 1 of SEQ ID NO:38. In order to prepare yeast expressing this a *S. cerevisiae* codon optimized *S. grosvenorii* Epoxide hydrolase 1 gene sequence of SEQ ID NO:37 was introduced in the yeast strain EFSC3027. The other epoxide hydrolase was *S. grosvenorii* Epoxide hydrolase 2 of SEQ ID NO:40. In order to prepare yeast expressing this a *S. cerevisiae* codon optimized *S. grosvenorii* Epoxide hydrolase 1 gene sequence of SEQ ID NO:39 was introduced in the yeast strain EFSC3027. FIG. 7 shows the LC-MS mass peak 501 corresponding to the proton plus Na+ adduct of tetrahydroxysqualene in a sample from yeast strain EFSC3027 transformed with a plasmid expressing *S. grosvenorii* Epoxide hydrolase 2. Tetrahydroxysqualene is made by the hydrolysis of 2,3 and 22,23 epoxide bonds of dioxidosqualene. No accumulation of tetrahydroxy squalene was detected in the EFSC301 background strain. Samples were made by boiling culture aliquots in 50% DMSO and then pelleting of cell material by centrifugation. Supernatants were then measured by ESI LC-MS.

A similar system for boosting oxidosqualene availability for β-amyrin production was described by Kirby, J et al in FEBS Journal 275 (2008) 1852-1859

Example 10—Production of Cucurbitadienol in Yeast Strain EFSC3027

Figure 8:
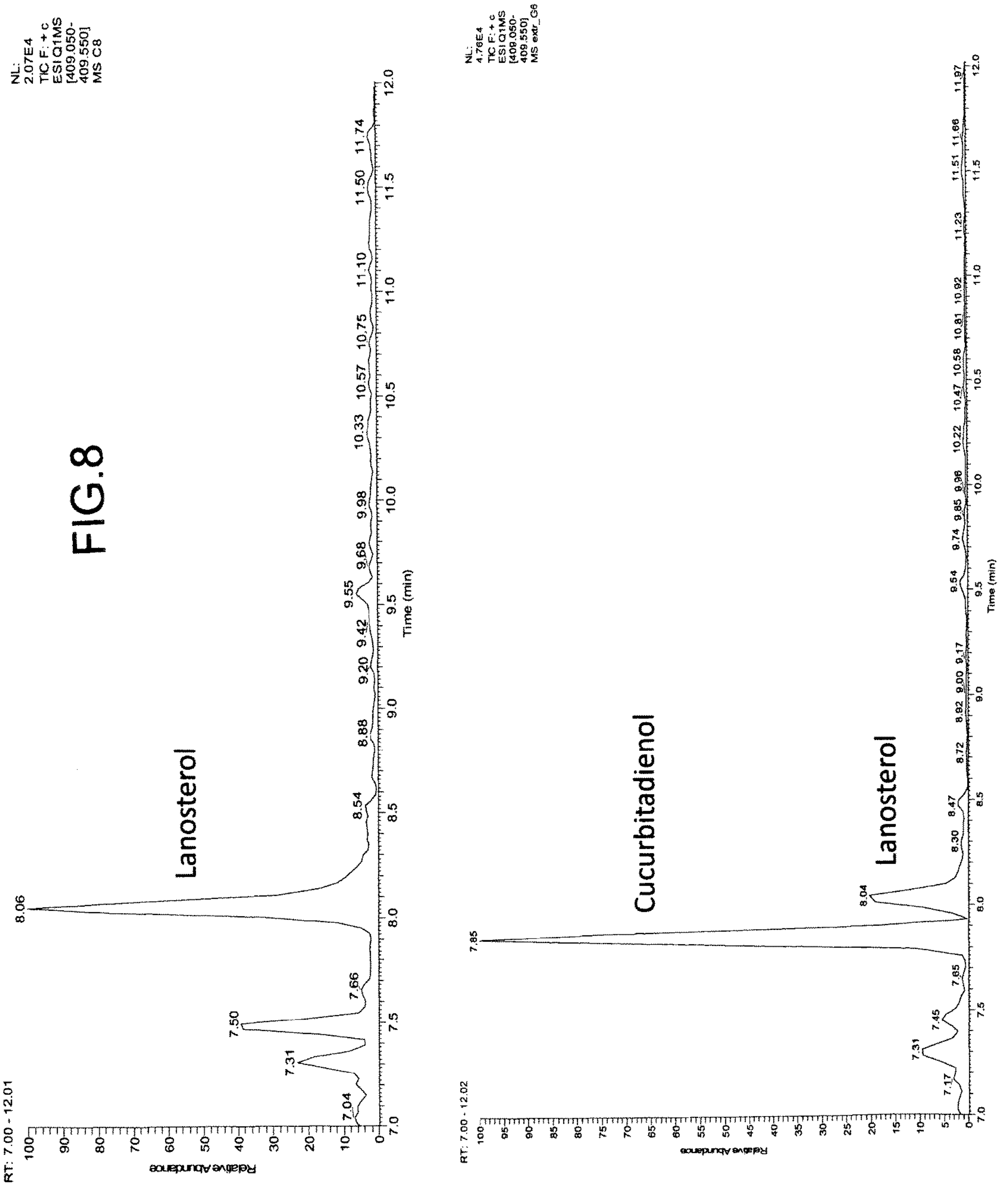
FIG. 8 shows the LC-MS chromatogram peak of lanosterol in yeast strain (upper panel) and LC-MS chromatogram peaks of cucurbitadienol and lanosterol in yeast strain EFSC3498, which expresses cucurbitadienol synthase (lower panel).

When a *S. cerevisiae* codon optimized gene copy of the *Siraitia grosvenorii* cucurbitadienol synthase of Accession No HQ128567 (sequence provided herein as SEQ ID NO:42) is integrated into the genome of yeast strain EFSC3027 and transcription of this gene is driven by the GPD1 promoter, the expression of the cucurbitadienol synthase results in production of cucurbitadienol in the yeast strain in amounts that are easily detectable by ESI LC-MS (see FIG. 8). The amino acid sequence of *Siraitia grosvenorii* cucurbitadienol synthase is provided herein as SEQ ID NO:43. The strain comprising SEQ ID NO:42 producing cucurbitadienol is called EFSC3498. Yeast strains were grown at 30° C. for 5 days in synthetic complete medium containing 2% glucose, and cucurbitadienol was extracted by boiling a culture sample in 50% ethanol/20% KOH for 5 minutes followed by extraction with an equal volume of hexane and then evaporation of hexane and resuspension of dried extract in methanol. FIG. 8 shows the LC-MS chromatogram peak of lanosterol in EFSC3027 (upper frame) and the LC-MS chromatogram peaks of cucurbitadienol and lanosterol in EFSC3498 (lower frame). The peak corresponding to lanosterol shows a retention time of ~8.05 whereas the peak corresponding to cucurbitadienol has a retention time of 7.85. Both lanosterol and cucurbitadienol shows a mass in the LC-MS chromatogram of 409.4 (proton adduct minus one $H_2O$)

Example 11—Production of Oxo and Hydroxy Cucurbitadienol in *S. cerevisiae*

Figure 9:
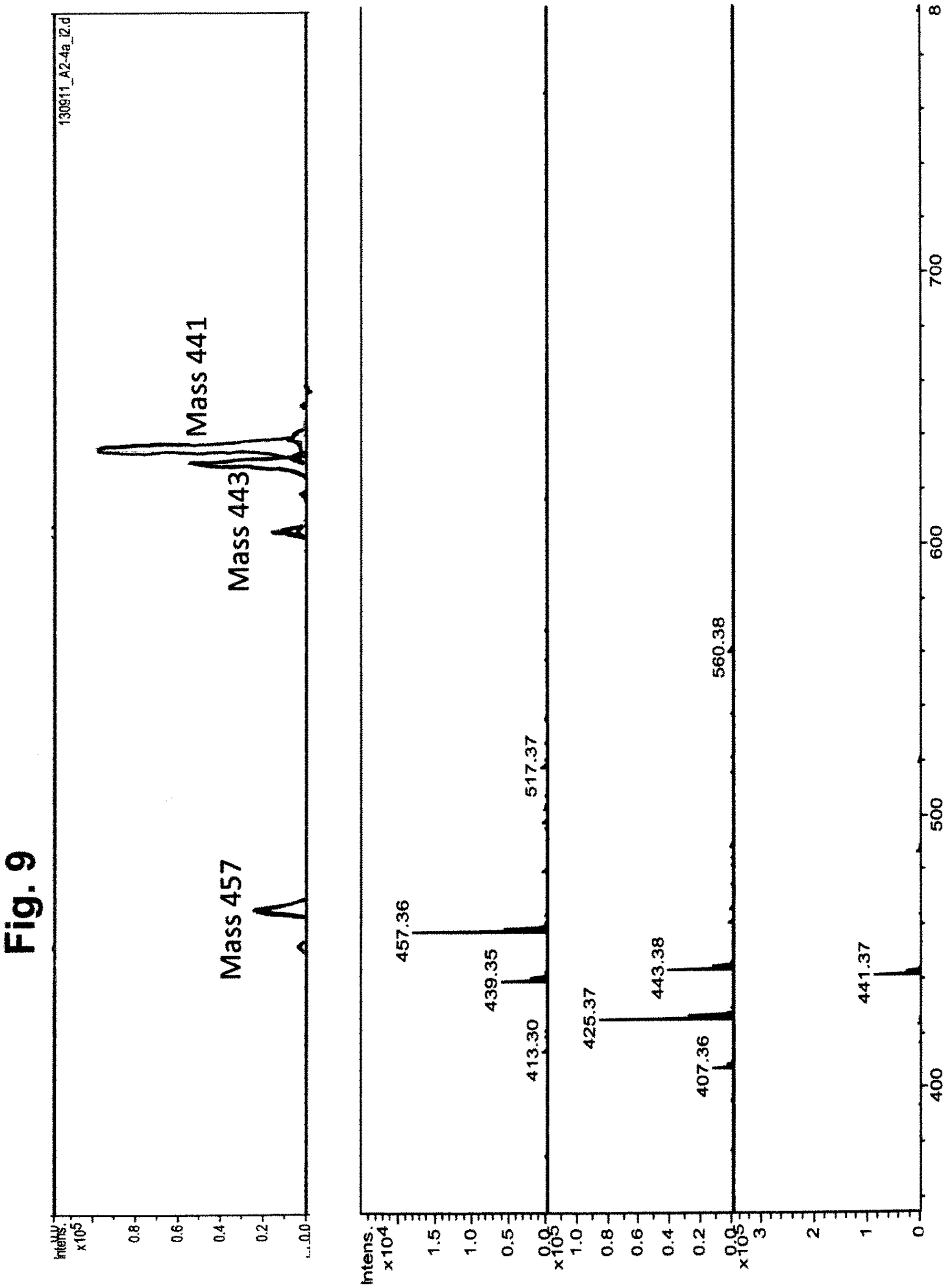
FIG. 9 shows the LC-MS chromatogram with the three peaks made when CYP5491 and CPR4497 are expressed in yeast strain EFSC3498 (upper panel), while the three lower panels show the fragmentation spectrum of these three peaks. The masses of the 3 peaks (443.38, 441.37 and 457.36) correspond in weight to proton adducts of hydroxylated cucurbitadienol, oxo cucurbitadienol and hydroxy plus oxo cucurbitadienol respectively.

When the cucurbitadienol producing yeast strain EFSC3498 (prepared as described in Example 10) is transformed with two plasmids, one expressing the *S. grosvenorii* CYP5491 from a TEF1 promoter, the other expressing the *S. grosvenorii* CPR4497 also from a TEF1 promoter (DNA sequence encoding CPR4497 provided as SEQ ID NO:14) three conspicuous peaks emerge (see FIG. 9 for LC-MS chromatogram peaks). The amino acid sequence of *S. grosvenorii* CYP5491 is provided herein as SEQ ID NO:44 and the DNA sequence encoding *S. grosvenorii* CYP5491 is provided as SEQ ID NO:14. The amino acid sequence of *S. grosvenorii* CPR4497 is provided herein as SEQ ID NO:46 and the DNA sequence encoding *S. grosvenorii* CPR4497 is provided as SEQ ID NO:45. The upper frame in FIG. 9 shows the LC-MS chromatogram with the three peaks made when CYP5491 and CPR4497 are expressed in EFSC3498, while the three lower frames show the fragmentation spectrum of these three peaks. CYP5491 is 99% identical to acc. no. HQ128570 and HQ128571 at both the amino acid and nucleotide sequence level. The masses of the 3 peaks (443.38, 441.37 and 457.36) correspond in weight to proton adducts of hydroxylated cucurbitadienol, oxo cucurbitadienol and hydroxy plus oxo cucurbitadienol respectively. Without being bound by theory it is believed that the hydroxylated cucurbitadienol (protonated mass 443.38) and oxidated cucurbitadienol (protonated mass 441.37) is 11-hydroxy-cucurbitadienol and 11-oxo-cucurbitadienol, respectively. The peak that corresponds to both oxo plus hydroxy cucurbitadienol (protonated mass 457.36) could be 11-oxo-24,25 epoxy cucurbitadienol, formed, either from cyclization of dioxidosqualene by the cucurbitadienol synthase and 11 hydroxylation by CYP5491 (FIG. 10B) or by CYP5491 being multifunctional, making both the 11-oxidation and the 24,25-epoxidation (FIG. 10A).

Figure 11:
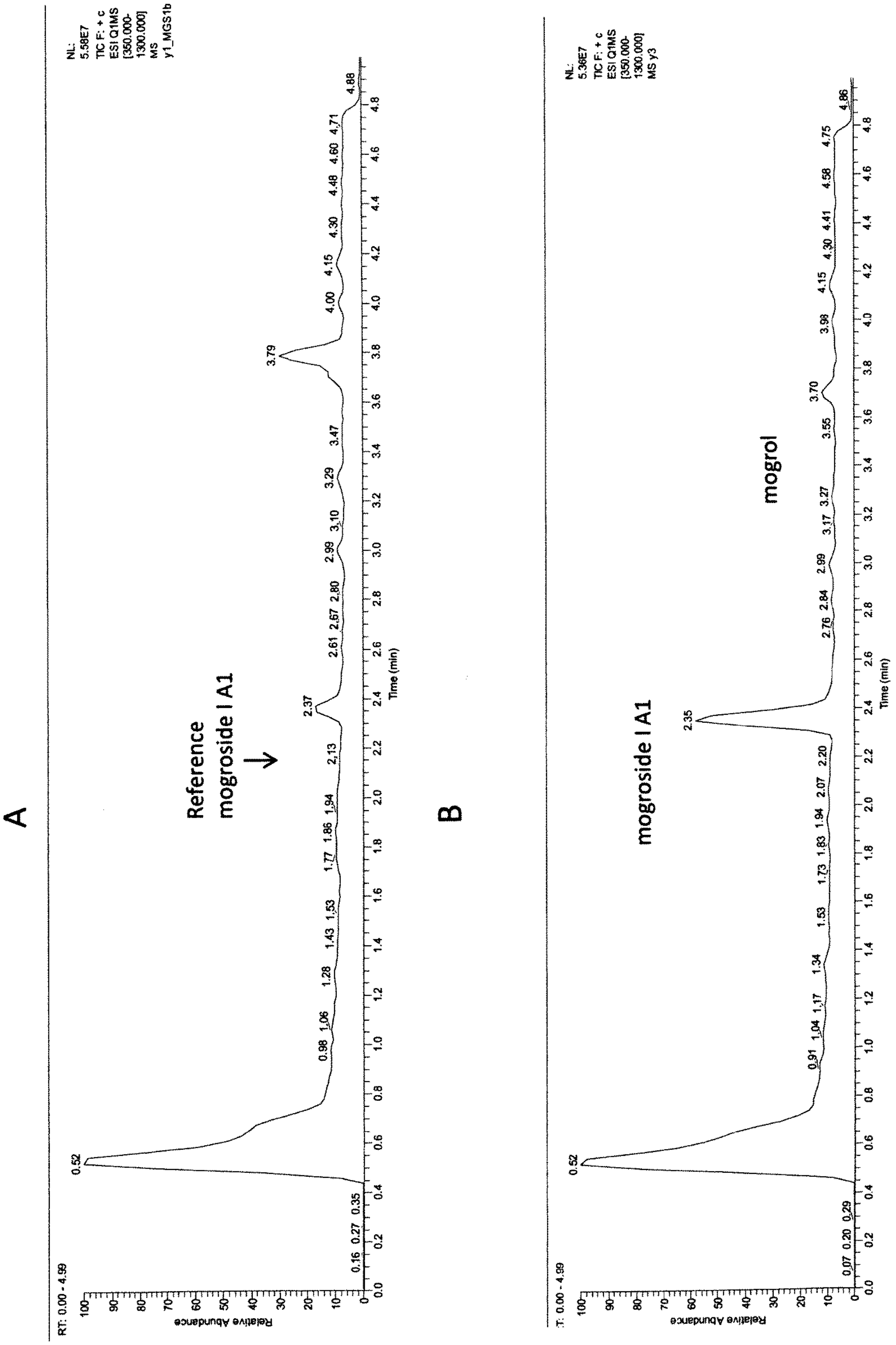

Example 12—Glycosylation of Mogrol in *S. cerevisiae* by Expression of *S. grosvenorii* UGTs UGTs 98, SK98 and 1576 were cloned from *S. grosvenorii* leaf and root cDNA by primers designed from fruit gene contigs assembled from illumina sequencing data. *S. grosvenorii* was purchased from Horizon Herbs, LLC, United States. The DNA sequence and protein sequence of UGT98 are provided herein as SEQ ID NO:51 and 53, respectively, whereas a SEQ ID NO:52 provides a DNA sequence encoding UGT98 codon optimised for expression in *S. cerevisiae*. The DNA sequence and protein sequence of UGTSK98 are provided herein as SEQ ID NO:49 and 50, respectively, The DNA sequence and protein sequence of UGT1576 are provided herein as SEQ ID NO:47 and 48, respectively. Yeast strain EFSC1563 has a deletion of the EXG1 gene and of the EXG2 gene both encoding and exo-1,3-beta-Glucanase. When yeast strain EFSC1563 (EFSC301 exg1 exg2) is transformed with a plasmid expressing UGT1576 driven by a GPD1 promoter and fed mogrol to a concentration in the growth medium of 10-100 uM, a clear formation of mogroside I A1 is detected by LC-MS (FIG. 11B). The produced mogroside I A1 shows the same retention time as the reference mogroside I A1 in the LC-MS analysis. FIG. 11A shows the LC-MS chromatogram of reference mogroside I A1, while 11B shows the peak from a sample of EFSC1563 expressing UGT1576 in a culture fed 50 uM mogrol. These data show that the UGT1576 gene encodes a glycosyltransferase with mogrol 24-OH UDP-glycosyltransferase activity. Samples were made by mixing culture aliquot 1:1 with DMSO followed by boiling (80° C.) for 5 minutes and pelleting by centrifugation. Supernatants were then subjected to ESI LC-MS.

Figure 12:
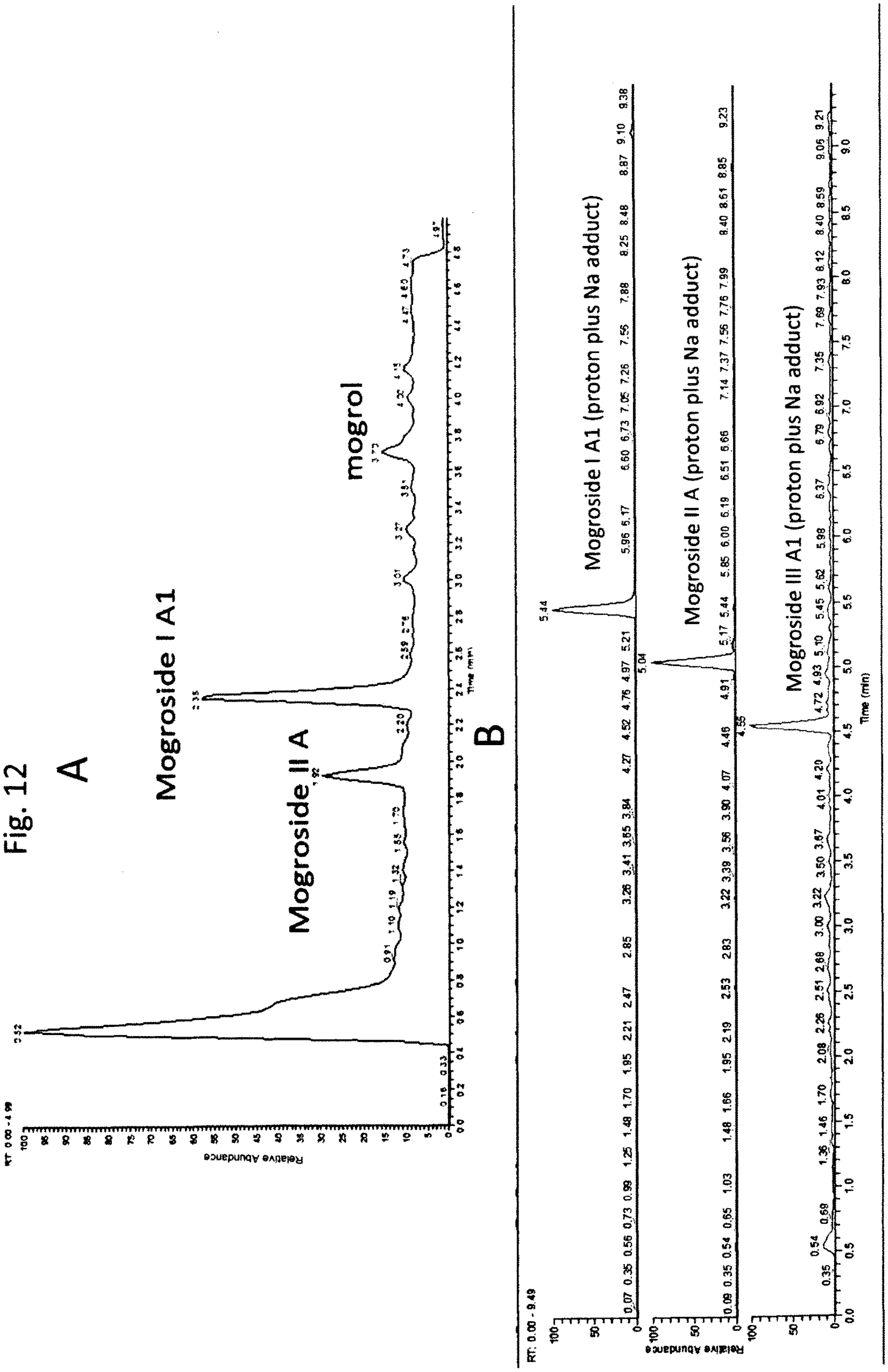
FIG. 12A shows the LC-MS chromatograms of samples from yeast strain EFSC1563 co-expressing UGT SK98 with UGT1576 showing production of di-glycosylated mogrol (mogroside II A).
FIG. 12B shows LC-MS chromatograms of samples from yeast strain EFSC1563 co-expressing UGT98 with UGT1576 showing production of di and triglycosylated mogrol (middle and lower frames).

When UGTs 98 and SK98 cloned into yeast expression plasmids with expression from GPD1 promoters are transformed into EFSC1563 without co-transformation of a UGT1576 expression plasmid, no conversion of fed mogrol is detected. In contrast, co-expression of UGT98 or UGT SK98 with UGT1576 in EFSC1563 fed with mogrol results in further glycosylation of mogroside I A1. UGT SK98 co-expressed with UGT1576 results in production of di-glycosylated mogrol (mogroside II A, FIG. 12A)$_{[LAD1]}$, while co-expression with UGT98 results in di and tri-glycosylated mogrol (middle and lower frames, FIG. 12B$_{[LAD2]}$). The di-glycosylated mogrol that is formed by both UGT98 and UGT SK98 has a different retention time than mogroside II E and mogroside II A1 during LC-MS, making it likely that it is mogroside II A. This means that both UGT98 and UGT SK98 can catalyse a 1,2 glucosylation of the glucose of mogroside I A1. UGT98 appears to be multifunctional, catalysing 1,2 glycosylation of mogroside I A1 resulting in production of mogroside II A, followed by what may be a 1,6 glycosylation of mogroside II A to form mogroside III A1 (FIG. 12B). We believe that UGT98 catalyses 1,6 glycosylation of mogroside II because mogrol itself is not glycosylated by the UGT98. It is therefore likely that the UGT98 is multifunctional, being both a 1,2 and 1,6 UDP-glucose glycosyl transferase of the 24-glucose moiety of mogrosides. UGTs 98 and SK98 belong to the UGT91 family of UDP-glucose glycosyltransferases and members of this family are known to be 1,2 and 1,6 glycosyltransferases.

Figure 13:
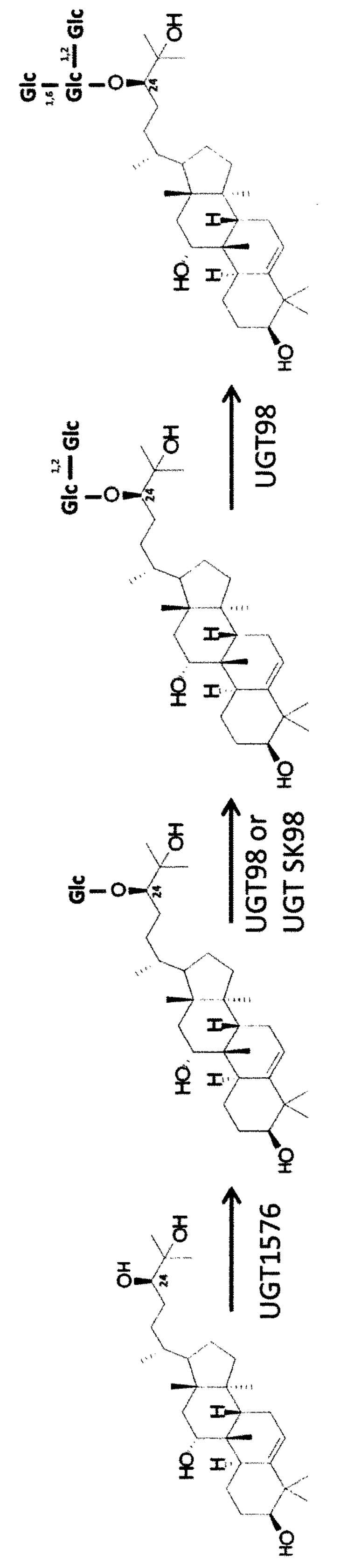
FIG. 13 shows a route from mogrol to Mogroside III A1 proposed by the present invention.

FIG. 13 schematically summarizes the glycosylation reactions from mogrol to mogroside III A1

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A recombinant host cell capable of producing a mogrol precursor, a mogroside precursor, and/or a mogroside compound in a cell culture, the recombinant host cell comprising:

(a) a gene encoding a polypeptide capable of catalyzing conversion of oxido-squalene to produce cucurbitadienol;
wherein the polypeptide comprises a polypeptide having at least 90% sequence identity to the amino acid sequence set forth in SEQ ID NO: 1;

(b) a gene encoding a polypeptide capable of catalyzing conversion of dioxido-squalene to produce 24,25-epoxy cucurbitadienol;
wherein the polypeptide comprises a polypeptide having at least 90% sequence identity to the amino acid sequence set forth in SEQ ID NO: 1;

(c) a gene encoding a polypeptide capable of catalyzing hydroxylation of cucurbitadienol to produce 11-hydroxy-cucurbitadienol;
wherein the polypeptide comprises a polypeptide having at least 90% sequence identity to the amino acid sequence encoded by a nucleotide sequence set forth in any one of SEQ ID NOs: 3-20 or 41;

(d) a gene encoding a polypeptide capable of catalyzing conversion of 11-hydroxy-cucurbitadienol to produce mogrol;
wherein the polypeptide comprises a polypeptide having at least 90% sequence identity to the amino acid sequence encoded by a nucleotide sequence set forth in any one of SEQ ID NOs: 3-20 or 41;

(e) a gene encoding a polypeptide capable of catalyzing epoxidation of 11-hydroxy-cucurbitadienol to produce 11-hydroxy-24,25-epoxy cucurbitadienol;
wherein the polypeptide comprises a polypeptide having at least 90% sequence identity to the amino acid sequence encoded by a nucleotide sequence set forth in any one of SEQ ID NOs: 3-20 or 41;

(f) a gene encoding a polypeptide capable of catalyzing conversion of 11-hydroxy-24,25-epoxy cucurbitadienol to produce mogrol;
wherein the polypeptide comprises a polypeptide having at least 90% sequence identity to the amino acid sequence encoded by a nucleotide sequence set forth in any one of SEQ ID NOs: 3-20 or 41;

(g) a gene encoding a polypeptide capable of catalyzing epoxidation of cucurbitadienol to produce 24,25-epoxy cucurbitadienol;
wherein the polypeptide comprises a polypeptide having at least 90% sequence identity to the amino acid sequence encoded by a nucleotide sequence set forth in any one of SEQ ID NOs: 3-20 or 41;

(h) a gene encoding a polypeptide capable of catalyzing hydroxylation of 24,25-epoxy cucurbitadienol to produce 11-hydroxy-24,25-epoxy cucurbitadienol;
wherein the polypeptide comprises a polypeptide having at least 90% sequence identity to the amino acid sequence encoded by a nucleotide sequence set forth in any one of SEQ ID NOs: 3-20 or 41; and/or (i) a gene encoding a polypeptide capable of catalyzing glycosylation of mogrol and/or glycosylated mogrol to produce a mogroside compound;
wherein the polypeptide comprises a polypeptide having at least 90% sequence identity to the amino acid sequence set forth in any one of SEQ ID NOs: 21-25 and/or a polypeptide having at least 90% sequence identity to the amino acid sequence encoded by the nucleotide sequence set forth in any one of SEQ ID NOs: 26-36;

wherein at least one of the genes is a recombinant gene.

2. The recombinant host cell of claim 1, comprising components (c), (d), and (i).

3. The recombinant host cell of claim 1, comprising components (b), (f), (h), and (i).

4. The recombinant host cell of claim 1, comprising components (f), (h), and (i).

5. The recombinant host cell of claim 1, comprising component (i).

6. The recombinant host cell of claim 1, wherein the recombinant host cell further comprises a heterologous nucleic acid encoding a squalene epoxidase (ERG1) polypeptide (ERG1) polypeptide.

7. The recombinant host cell of claim 1, wherein the recombinant host cell has been modified to have reduced expression of a lanosterol synthase (ERG7) polypeptide (ERG7) polypeptide.

8. The recombinant host cell of claim 1, wherein the recombinant host cell is a microorganism that is a plant cell, a mammalian cell, an insect cell, a fungal cell, an algal cell, or a bacterial cell.

9. The recombinant host cell of claim 8, wherein the bacterial cell is an *Escherichia, Lactobacillus, Lactococcus, Corynebacterium, Acetobacter, Acinetobacter*, or *Pseudomonas* cell.

10. The recombinant host cell of claim 8, wherein the fungal cell is a yeast cell.

11. The recombinant host cell of claim 10, wherein the yeast cell is a *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous*, or *Candida albicans* cell.

12. The recombinant host cell of claim 11, wherein the yeast cell is a *Saccharomycete.*

13. The recombinant host cell of claim 12, wherein the yeast cell is a cell from the *Saccharomyces cerevisiae* species.

14. The recombinant host cell of claim 1, comprising components (a), (c), (d) and (i).

15. The recombinant host cell of claim 1, comprising components (a), (c), (e), (f), and (i).

16. The recombinant host cell of claim 1, comprising components (a), (g), (h), (f), and (i).

17. The recombinant host cell of claim 1, wherein the mogroside compound is glycosylated at its C-24 hydroxyl group;

wherein the glycosylation is effected by the activity of the polypeptide having at least 90% sequence identity to the amino acid sequence set forth in any one of SEQ ID NOs: 21-25 and/or a polypeptide having at least 90% sequence identity to the amino acid sequence encoded by the nucleotide sequence set forth in any one of SEQ ID NOs: 26-36.

18. The recombinant host cell of claim 1, wherein the mogroside compound is glycosylated at its C-3 hydroxyl group;

wherein the glycosylation is effected by the activity of the polypeptide having at least 90% sequence identity to the amino acid sequence set forth in any one of SEQ ID NOs: 21-25.

19. The recombinant host cell of claim 1, wherein the mogroside compound is mogroside I A1, mogroside I E1, mogroside II A, mogroside II E, mogroside III, mogroside III A1, mogroside III A2, mogroside IV, siamenoside, or mogroside V.

20. The recombinant host cell of claim 1, wherein the mogrol precursor is squalene, oxidosqualene, dioxidosqualene, cucurbitadienol, 24,25-epoxy cucurbitadienol, 11-hydroxy-cucurbitadienol, 11-hydroxy-24,25-epoxy cucurbitadienol, or 11-oxo-mogrol.

21. The recombinant host cell of claim 1, wherein the recombinant host cell is a *Yarrowia lipolytica* cell.

22. The recombinant host cell of claim 1, wherein:

(a) the glycosylation is effected by the activity of the polypeptide having at least 90% sequence identity to the amino acid sequence encoded by a nucleotide sequence set forth in any one of SEQ ID NOs: 26-36 or the amino acid sequence set forth in any one of SEQ ID NOs: 21-25 and the mogroside compound is mogroside I A1;

(b) the glycosylation is effected by the activity of the polypeptide having at least 90% sequence identity to the amino acid sequence set forth in any one of SEQ ID NOs: 21-25 and the mogroside compound is mogroside I E1;

(c) the glycosylation is effected by the activity of the polypeptide having at least 90% sequence identity to the amino acid sequence encoded by a nucleotide sequence set forth in any one of SEQ ID NOs: 26-36 or the amino acid sequence set forth in any one of SEQ ID NOs: 21-25 and the mogroside compound is mogroside II E; or (d) the glycosylation is effected by the activity of the polypeptide having at least 90% sequence identity to the amino acid sequence set forth in any one of SEQ ID NOs: 21-25 and the mogroside compound is siamenoside I.

23. The recombinant host of claim 1, wherein the mogroside precursor is mogrol or a glycosylated, a di-glycosylated, or a tri-glycosylated mogrol.

24. The recombinant host cell of claim 1, wherein the mogroside compound is a glycosylated, a di-glycosylated, or a tetra-glycosylated mogroside compound.

25. The recombinant host of claim 24, wherein:

(a) the glycosylated mogroside compound is mogroside I A1 or mogroside I E1;

(b) the di-glycosylated mogroside compound is mogroside II A or mogroside II E; and (c) the tetra-glycosylated mogroside compound is siamenoside I.

26. A method of producing a mogrol precursor, a mogroside precursor, and/or a mogroside compound, comprising culturing the recombinant host cell of claim 1 in a culture medium under conditions in which one or more of the genes are expressed, and wherein the mogrol precursor, mogroside precursor, and/or mogroside compound is produced by the recombinant host cell.

* * * * *

SEQUENCE LISTING

```
<160> NUMBER OF SEQ ID NOS: 41

<210> SEQ ID NO 1
<211> LENGTH: 764
<212> TYPE: PRT
```

-continued

<213> ORGANISM: Cucurbita pepo

<400> SEQUENCE: 1

```
Met Trp Arg Leu Lys Val Gly Ala Glu Ser Val Gly Glu Glu Asp Glu
1               5                   10                  15

Lys Trp Val Lys Ser Val Ser Asn His Leu Gly Arg Gln Val Trp Glu
            20                  25                  30

Phe Cys Ala Asp Ala Ala Ala Asp Thr Pro His Gln Leu Leu Gln Ile
        35                  40                  45

Gln Asn Ala Arg Asn His Phe His His Asn Arg Phe His Arg Lys Gln
    50                  55                  60

Ser Ser Asp Leu Phe Leu Ala Ile Gln Tyr Glu Lys Glu Ile Ala Lys
65                  70                  75                  80

Gly Ala Lys Gly Gly Ala Val Lys Val Lys Glu Gly Glu Glu Val Gly
                85                  90                  95

Lys Glu Ala Val Lys Ser Thr Leu Glu Arg Ala Leu Gly Phe Tyr Ser
            100                 105                 110

Ala Val Gln Thr Arg Asp Gly Asn Trp Ala Ser Asp Leu Gly Gly Pro
        115                 120                 125

Leu Phe Leu Leu Pro Gly Leu Val Ile Ala Leu His Val Thr Gly Val
    130                 135                 140

Leu Asn Ser Val Leu Ser Lys His His Arg Val Glu Met Cys Arg Tyr
145                 150                 155                 160

Leu Tyr Asn His Gln Asn Glu Asp Gly Gly Trp Gly Leu His Ile Glu
                165                 170                 175

Gly Thr Ser Thr Met Phe Gly Ser Ala Leu Asn Tyr Val Ala Leu Arg
            180                 185                 190

Leu Leu Gly Glu Asp Ala Asp Gly Gly Asp Gly Gly Ala Met Thr Lys
        195                 200                 205

Ala Arg Ala Trp Ile Leu Glu Arg Gly Gly Ala Thr Ala Ile Thr Ser
    210                 215                 220

Trp Gly Lys Leu Trp Leu Ser Val Leu Gly Val Tyr Glu Trp Ser Gly
225                 230                 235                 240

Asn Asn Pro Leu Pro Pro Glu Phe Trp Leu Leu Pro Tyr Ser Leu Pro
                245                 250                 255

Phe His Pro Gly Arg Met Trp Cys His Cys Arg Met Val Tyr Leu Pro
            260                 265                 270

Met Ser Tyr Leu Tyr Gly Lys Arg Phe Val Gly Pro Ile Thr Pro Lys
        275                 280                 285

Val Leu Ser Leu Arg Gln Glu Leu Tyr Thr Ile Pro Tyr His Glu Ile
    290                 295                 300

Asp Trp Asn Lys Ser Arg Asn Thr Cys Ala Lys Glu Asp Leu Tyr Tyr
305                 310                 315                 320

Pro His Pro Lys Met Gln Asp Ile Leu Trp Gly Ser Ile Tyr His Val
                325                 330                 335

Tyr Glu Pro Leu Phe Thr Arg Trp Pro Gly Lys Arg Leu Arg Glu Lys
            340                 345                 350

Ala Leu Gln Ala Ala Met Lys His Ile His Tyr Glu Asp Glu Asn Ser
        355                 360                 365

Arg Tyr Ile Cys Leu Gly Pro Val Asn Lys Val Leu Asn Met Leu Cys
    370                 375                 380

Cys Trp Val Glu Asp Pro Tyr Ser Asp Ala Phe Lys Leu His Leu Gln
385                 390                 395                 400
```

-continued

Arg Val His Asp Tyr Leu Trp Val Ala Glu Asp Gly Met Arg Met Gln
405 410 415

Gly Tyr Asn Gly Ser Gln Leu Trp Asp Thr Ala Phe Ser Ile Gln Ala
420 425 430

Ile Val Ala Thr Lys Leu Val Asp Ser Tyr Ala Pro Thr Leu Arg Lys
435 440 445

Ala His Asp Phe Val Lys Asp Ser Gln Ile Gln Glu Asp Cys Pro Gly
450 455 460

Asp Pro Asn Val Trp Phe Arg His Ile His Lys Gly Ala Trp Pro Leu
465 470 475 480

Ser Thr Arg Asp His Gly Trp Leu Ile Ser Asp Cys Thr Ala Glu Gly
485 490 495

Leu Lys Ala Ser Leu Met Leu Ser Lys Leu Pro Ser Thr Met Val Gly
500 505 510

Glu Pro Leu Glu Lys Asn Arg Leu Cys Asp Ala Val Asn Val Leu Leu
515 520 525

Ser Leu Gln Asn Asp Asn Gly Gly Phe Ala Ser Tyr Glu Leu Thr Arg
530 535 540

Ser Tyr Pro Trp Leu Glu Leu Ile Asn Pro Ala Glu Thr Phe Gly Asp
545 550 555 560

Ile Val Ile Asp Tyr Pro Tyr Val Glu Cys Thr Ala Ala Thr Met Glu
565 570 575

Ala Leu Thr Leu Phe Lys Lys Leu His Pro Gly His Arg Thr Lys Glu
580 585 590

Ile Asp Thr Ala Ile Gly Lys Ala Ala Asn Phe Leu Glu Lys Met Gln
595 600 605

Arg Ala Asp Gly Ser Trp Tyr Gly Cys Trp Gly Val Cys Phe Thr Tyr
610 615 620

Ala Gly Trp Phe Gly Ile Lys Gly Leu Val Ala Ala Gly Arg Thr Tyr
625 630 635 640

Asn Ser Cys Leu Ala Ile Arg Lys Ala Cys Glu Phe Leu Leu Ser Lys
645 650 655

Glu Leu Pro Gly Gly Gly Trp Gly Glu Ser Tyr Leu Ser Cys Gln Asn
660 665 670

Lys Val Tyr Thr Asn Leu Glu Gly Asn Lys Pro His Leu Val Asn Thr
675 680 685

Ala Trp Val Leu Met Ala Leu Ile Glu Ala Gly Gln Gly Glu Arg Asp
690 695 700

Pro Ala Pro Leu His Arg Ala Ala Arg Leu Leu Met Asn Ser Gln Leu
705 710 715 720

Glu Asn Gly Asp Phe Val Gln Gln Glu Ile Met Gly Val Phe Asn Lys
725 730 735

Asn Cys Met Ile Thr Tyr Ala Ala Tyr Arg Asn Ile Phe Pro Ile Trp
740 745 750

Ala Leu Gly Glu Tyr Cys His Arg Val Leu Thr Glu
755 760

<210> SEQ ID NO 2
<211> LENGTH: 250
<212> TYPE: PRT
<213> ORGANISM: Siraitia grosvenorii

<400> SEQUENCE: 2

Leu Glu Arg Asn Arg Leu Cys Asp Ala Val Asn Val Leu Leu Ser Leu
1 5 10 15

```
Gln Asn Asp Asn Gly Gly Phe Ala Ser Tyr Glu Leu Thr Arg Ser Tyr
            20                  25                  30

Pro Trp Leu Glu Leu Ile Asn Pro Ala Glu Thr Phe Gly Asp Ile Val
        35                  40                  45

Ile Asp Tyr Pro Tyr Val Glu Cys Thr Ser Ala Thr Met Glu Ala Leu
    50                  55                  60

Thr Leu Phe Lys Lys Leu His Pro Gly His Arg Thr Lys Glu Ile Asp
65                  70                  75                  80

Thr Ala Ile Val Arg Ala Ala Asn Phe Leu Glu Asn Met Gln Arg Thr
                85                  90                  95

Asp Gly Ser Trp Tyr Gly Cys Trp Gly Val Cys Phe Thr Tyr Ala Gly
            100                 105                 110

Trp Phe Gly Ile Lys Gly Leu Val Ala Ala Gly Arg Thr Tyr Asn Asn
        115                 120                 125

Cys Leu Ala Ile Arg Lys Ala Cys Asp Phe Leu Leu Ser Lys Glu Leu
    130                 135                 140

Pro Gly Gly Gly Trp Gly Glu Ser Tyr Leu Ser Cys Gln Asn Lys Val
145                 150                 155                 160

Tyr Thr Asn Leu Glu Gly Asn Arg Pro His Leu Val Asn Thr Ala Trp
                165                 170                 175

Val Leu Met Ala Leu Ile Glu Ala Gly Gln Ala Glu Arg Asp Pro Thr
            180                 185                 190

Pro Leu His Arg Ala Ala Arg Leu Leu Ile Asn Ser Gln Leu Glu Asn
        195                 200                 205

Gly Asp Phe Pro Gln Gln Glu Ile Met Gly Val Phe Asn Lys Asn Cys
    210                 215                 220

Met Ile Thr Tyr Ala Ala Tyr Arg Asn Ile Phe Pro Ile Trp Ala Leu
225                 230                 235                 240

Gly Glu Tyr Cys His Arg Val Leu Thr Glu
                245                 250
```

<210> SEQ ID NO 3
<211> LENGTH: 1572
<212> TYPE: DNA
<213> ORGANISM: Siraitia grosvenorii

<400> SEQUENCE: 3

```
atggaactct tctctaccaa aactgcagcc gagatcatcg ctgttgtctt gtttttctac      60

gctctcatcc ggctattatc tggaagattc agctctcaac agaagagact gccacctgaa     120

gccggtggcg cctggccact gatcggccat ctccatctcc taggtgggtc ggaacctgca     180

cataaaacct tggcgaacat ggcggacgcc tacggaccag tttttacgtt gaaactgggc     240

atgcatacag ctttggttat gagcagttgg gaaatagcga gagagtgctt tactaaaaac     300

gacagaatct ttgcctcccg ccccatagtc actgcctcaa agcttctcac ctataaccat     360

accatgtttg ggttcagcca atatggtcca ttctggcgcc atatgcgcaa aatagccacg     420

cttcaactcc tctcaaacca ccgcctcgag cagctccaac acatcagaat atcggaggtc     480

cagacttcga ttaagaaact gtacgagttg tgggtcaaca gcagaaataa tggaggcgag     540

aaagtgttgg tggagatgaa gacgtggttc ggaggcataa ccttgaacac catattcagg     600

atggtggtcg gaaagcgatt ctcgactgct ttcgaaggca gtggtggcga acggtatcgg     660

aaggcgttga gggattctct tgaatggttt ggggcattcg ttccgtcaga ttcattcccg     720

tttttaagat ggttggattt gggaggatat gagaaggcga tgaagaagac ggcgagtgtg     780
```

ctggacgagg tgcttgataa atggctcaaa gagcatcagc agaggagaaa ctccggtgaa 840
ctggagacgg aggagcacga cttcatgcac gtgatgctgt ctattgttaa ggatgatgaa 900
gaactatccg gctacgatgc cgatacagtc acaaaagcta catgtttgaa tttaatagtt 960
ggtggattcg acactacaca agtaactatg acatgggctc tttctttgct tctcaacaat 1020
gaagaggtat taaaaaaggc ccaacttgaa ctagacgaac aagttggaag agagaggttt 1080
gtggaagagt ccgatgttaa aaatctgtta tatctccagg ccatcgtgaa ggaaactttg 1140
cgtttgtacc cttcagcgcc aatctcgaca tttcatgagg ccatggaaga ttgcactgtt 1200
tctggctacc acatcttttc agggacgcgt ttgatggtga atcttcaaaa gcttcaaaga 1260
gatccacttg catgggagga tccatgtgac tttcgaccgg agagatttct gacaactcat 1320
aaggatttcg atcttagagg acatagtcct caattgatac catttgggag tggtcgaaga 1380
atatgccctg gcatctcgtt tgccattcaa gttttgcatc ttacgcttgc aaatctactt 1440
catgggtttg acattggaag gccatctcat gaaccaatcg atatgcagga gagtaaagga 1500
ctaacgagta ttaaaacaac tccacttgag gttgttttag ctccacgcct tgctgctcaa 1560
gtttatgagt ga 1572

<210> SEQ ID NO 4
<211> LENGTH: 1497
<212> TYPE: DNA
<213> ORGANISM: Siraitia grosvenorii

<400> SEQUENCE: 4
atgccgatcg cagaaggtgc agtctctgat ttgtttggtc gcccactctt ctttgcacta 60
tatgattggt tcttagagca tggatctgtt tataaacttg cctttggacc aaaagccttt 120
gttgttgtat cagatcccat tgtggcaaga tatattcttc gagaaaatgc atttggttat 180
gacaagggag tgcttgctga tattttagaa ccgataatgg gtaaaggact aataccagct 240
gaccttggca cttggaagca gaggagacga gttattgctc caggattcca tgccttgtac 300
ttggaagcta tgaccaaagt atttgccaat tgttcagaac gatcaatatt gaaattggag 360
aagcttctag gagaaggtga actacaggag aataaaacca ttgagttgga tatggaagca 420
gagttttcaa gtttggctct tgatatcatt ggactcggtg ttttcaacta tgattttggt 480
tctgtaacca aagaatctcc ggtgattaag gctgtatatg ggactctttt tgaagcagag 540
catagatcga ctttctatat cccatattgg aaagtacctt tggcaaggtg gatagtccca 600
aggcagcgta aattccatgg tgaccttaag gttattaatg agtgtcttga tggcctaata 660
cgcaacgcaa gagaaacccg agacgaaacg gatgttgaga aattgcagca aagggactac 720
ttaaatctca aggatgccag tcttttgcgt ttcttagttg atatgcgggg agctgatgtt 780
gatgatcgcc agcttaggga cgatctgatg acgatgctta ttgctggcca tgaaacaact 840
gctgctgtgc ttacatgggc tgttttttttg cttgcacaaa atccttcaaa aatgaaaaaa 900
gcgcaagcag agattgattt ggttcttggc atggggaggc caacttttga atcatttaaa 960
gcattgaagt acatcagact tatcgttgca gagactcttc gtttgtttcc tcagcctcca 1020
ttgctgataa gacgagctct caaatcagat atattaccag gaggatacaa tggtgacaaa 1080
actggatatg caattcctgc agggactgac atcttcatct ctgtttacaa tctccacaga 1140
tctccctact tctgggataa tcctcaagaa tttgaaccag agagatttca agtaaagagg 1200
gcaagcgagg gaattgaagg atgggatggt ttcgacccat ctagaagccc tggagctcta 1260
tacccgaatg agattgtagc agacttttcc ttcttaccat ttggtggagg ccctagaaaa 1320
tgtgtgggag atcaatttgc tctaatggag tcaactatag cattggccat gttactgcag 1380
aagtttgatg tggagctaaa aggaagtcca gaatctgtag aactagttac tggagccaca 1440
atacatacca aaagtgggtt gtggtgcaaa ctgagaagaa gatcacaagt aaactga 1497

<210> SEQ ID NO 5
<211> LENGTH: 1563
<212> TYPE: DNA
<213> ORGANISM: Siraitia grosvenorii

<400> SEQUENCE: 5
atggaaatgt cctcaagtgt cgcagccaca atcagtatct ggatggtcgt cgtatgtatc 60
gtaggtgtag gttggagagt cgtaaattgg gtttggttga gaccaaagaa attggaaaag 120
agattgagag aacaaggttt ggccggtaat tcttacagat tgttgttcgg tgacttgaag 180
gaaagagctg caatggaaga acaagcaaat tcaaagccta taaacttctc ccatgacatc 240
ggtccaagag ttttcccttc aatgtacaag accatccaaa actacggtaa aaactcctac 300
atgtggttag gtccataccc tagagtccac atcatggatc cacaacaatt gaagaccgtt 360
tttactttgg tctacgacat tcaaaagcca aatttgaacc ctttgattaa attcttgtta 420
gatggtatcg ttacacatga aggtgaaaag tgggctaagc acagaaagat tattaaccca 480
gcattccatt tggaaaagtt gaaggatatg atacctgctt tctttcactc atgtaatgaa 540
atcgtcaacg aatgggaaag attgatttca aaagaaggtt cctgcgaatt ggatgtaatg 600
ccttatttgc aaaatttggc cgctgacgcc atttcaagaa ccgcttttgg ttcttcatac 660
gaagaaggta aaatgatctt ccaattgttg aaggaattga ctgatttggt tgtcaaggta 720
gcttttggtg tttatattcc aggttggaga ttcttgccta caaagagtaa caacaaaatg 780
aaggaaatta atagaaaaat caagtctttg ttgttgggta tcattaacaa gagacaaaag 840
gcaatggaag aaggtgaagc cggtcaatct gatttgttgg gtatattaat ggaaagtaat 900
tctaacgaaa tccaaggtga aggtaataac aaggaagatg gcatgtctat tgaagacgtc 960
atcgaagagt gtaaggtatt ttatataggt ggtcaagaaa ctacagcaag attattgatc 1020
tggactatga tattgttgtc cagtcataca gaatggcaag aaagagccag aaccgaagtc 1080
ttgaaggtat ttggtaataa gaaaccagat ttcgacggtt tgtcaagatt gaaggtagtt 1140
actatgatct tgaacgaagt tttaagattg tacccacctg cttccatgtt gacaagaatc 1200
atccaaaagg aaacaagagt tggtaaatta accttgccag caggtgttat cttgataatg 1260
cctatcatct tgatacatag agatcacgac ttgtggggtg aagatgctaa cgagtttaaa 1320
ccagaaagat tcagtaaagg tgtttctaag gcagccaaag tccaaccagc ctttttccct 1380
tttggttggg gtcctagaat ttgcatgggt caaaacttcg ctatgatcga agctaagatg 1440
gcattgagtt tgatcttgca aagattttct ttcgaattgt cttcatccta cgttcatgca 1500
ccaactgtcg tcttcactac acaaccacaa cacggtgccc acatcgtttt gagaaagtta 1560
tga 1563

<210> SEQ ID NO 6
<211> LENGTH: 1602
<212> TYPE: DNA
<213> ORGANISM: Siraitia grosvenorii

<400> SEQUENCE: 6
atggaaccac aaccaagtgc ggaattcaac tggaatcaca gcctaagcac cgtcgctatc 60

```
ggtgtcattg ccattatttt cttccgtttt ctcgtcaaaa gagtcaccgg cgccggtgag    120

cgaaagggtc cgaagccgcc aaaagtagcc ggagggtggc ctctaattgg ccacctccct    180

ctcctcggag gacctgaact gccccatgtc aaactgggtg gtttggctga taaatatggt    240

ccaatcttct cgatccggct gggtgtccac tccgccgtcg tgataaacag ttgggaggcg    300

gcgaaacagt tattaaccaa ccatgacgtc gccgtctctt cccgccccca aatgctcggc    360

ggaaaactcc tgggctacaa ctacgccgtg tttggtttcg gaccctacgg ctcttactgg    420

cgcaacatgc gcaagataac cacgcaagag cttctatcca atagcagaat ccagctccta    480

agagacgttc gagcgtcaga agtgaaccaa ggcataaaag agctctacca gcactggaaa    540

gaaagaagag acggtcacga ccaagccttg gtggaactgc agcagtgggt cggggacttg    600

actatgaatc tgattctcgg agtcatcgcc gggaaaaggt tctttggagc tgcagcaacg    660

gtagacgagg aagaggcgcg acggagccat aaagcattga aggagttgtt acattatatg    720

gggctttttc tactgggtga tgctgttcca tatctaggat ggttggacgt cggcggccat    780

gtgaaggcga tgaagaaaac ttcaaaagaa ttggaccgta tgttaacaca gtggttggag    840

gagcacaaga aggaaggacc caagaaagat cataaagact tcatggacgt gatgctttca    900

gttctcaatg aaacatccga tgttctttca gataagaccc atggcttcga tgctgatacc    960

atcatcaaag ctacatgtat gacgatggtt ttaggaggga gtgatacgac ggcggtggtt   1020

gtgatatggg caatctcgct gctgctgaat aatcgccctg cgttgagaaa agtgcaagaa   1080

gaactggaag cccatatcgg ccgagacaga gaactggagg aatcggatct cggtaagcta   1140

gtgtatttgc aggcagtcgt gaaggagaca ttgcggctgt acggagccgg aggccttttc   1200

tttcgtgaaa ccacagagga tgtcaccatc gacggattcc atgtcgagaa agggacatgg   1260

ctgttcgtga acgtggggaa gatccacaga gatgggaagg tgtggccgga gccaacggag   1320

ttcaaaccgg agaggtttct gacgacccac aaagatttg atctgaaggg ccagcggttt   1380

gagctcatcc ctttcggggg aggaagaaga tcgtgccctg gaatgtcttt tgggctccaa   1440

atgctacagc ttattttggg taaactgctt caggcttttg atatatcgac gccgggggac   1500

gccgccgttg atatgaccgg atccattgga ctgacgaaca tgaaagccac tccattggaa   1560

gtgctcatca ccccgcgctt gcctctttcg ctttacgatt ga                     1602
```

<210> SEQ ID NO 7
<211> LENGTH: 1236
<212> TYPE: DNA
<213> ORGANISM: Siraitia grosvenorii

<400> SEQUENCE: 7

```
atggagactc ttcttcttca tcttcaatcg ttatttcatc caatttcctt cactggtttc     60

gttgtcctct ttagcttcct gttcctgctc cagaaatggt tactgacacg tccaaactct    120

tcatcagaag cctcaccccc ttctccacca aagcttccca tcttcggaca ccttctaaac    180

ctgggtctgc atccccacat caccctcgga gcctacgctc gccgctatgg ccctctcttc    240

ctcctccact tcggcagcaa gcccaccatc gtcgtctctt ctgccgaaat cgctcgcgat    300

atcatgaaga cccacgacct cgtcttcgcc aaccgtccta aatcaagcat cagcgaaaag    360

attctttacg gctccaaaga tttagccgca tctccttacg gcgaatactg gaggcagatg    420

aaaagcgttg gcgtgcttca tcttttgagc aacaaaaggg ttcaatcctt tcgctctgtc    480

agagaagaag aagtcgaact gatgatccag aagatccaac agaacccccct atcagttaat    540
```

-continued

```
ttaagcgaaa tattctctgg actgacgaac gacatagttt gcagggtggc tttagggaga    600

aagtatggcg tgggagaaga cggaaagaag ttccggtctc ttctgctgga gtttggggaa    660

gtattgggaa gtttcagtac gagagacttc atcccgtggc tgggttggat tgatcgtatc    720

agtgggctgg acgccaaagc cgagagggta gccaaagagc tcgatgcttt ctttgacaga    780

gtgatcgaag atcacatcca tctaaacaag agagagaata atcccgatga gcagaaggac    840

ttggtggatg tgctgctttg tgtacagaga gaagactcca tcgggtttcc ccttgagatg    900

gatagcataa aagctttaat cttggacatg tttgctgcag gcacagacac gacatacacg    960

gtgttggagt gggcaatgtc ccaactgttg agacacccag aagcgatgaa gaaactgcag   1020

agggaggtca gagaaatagc aggtgagaaa gaacacgtaa gtgaggatga tttagaaaag   1080

atgcattact tgaaggcagt aatcaaagaa acgctgcggc tacacccacc aatcccactc   1140

ctcgtcccca gagaatcaac ccaagacatc aggttgaggg ggtacgatat cagaggcggc   1200

acccgggtta tgatcaatgc atgggccatc ggaaga                             1236
```

<210> SEQ ID NO 8
<211> LENGTH: 1614
<212> TYPE: DNA
<213> ORGANISM: Siraitia grosvenorii

<400> SEQUENCE: 8

```
atgtcgatga gtagtgaaat tgaaagcctc tgggttttcg cgctggcttc taaatgctct     60

gctttaacta aagaaaacat cctctggtct ttactcttct ttttcctaat ctgggtttct    120

gtttccattc tccactgggc ccatccgggc ggcccggctt ggggccgcta ctggtggcgc    180

cgccgccgca gcaattccac cgccgctgct attcccggcc cgagaggcct ccccctcgtc    240

ggcagcatgg gcttgatggc cgacttggcc caccaccgga ttgccgccgt ggctgactcc    300

ttaaacgcca cccgcctcat ggccttttcg ctcggcgaca ctcgcgtgat cgtcacatgc    360

aaccccgacg tcgccaaaga gattctcaac agctccctct tcgccgaccg ccccgttaag    420

gagtccgctt actccttgat gttcaaccgc gccattgggt tcgcccccta tggcctttac    480

tggcggaccc tccgccgcat cgcttcccac cacctcttct gccccaagca aatcaagtcc    540

tcccagtccc agcgccgcca aatcgcttcc caaatggtcg caatgttcgc aaaccgcgat    600

gccacacaga gcctctgcgt tcgcgactct ctcaagcggg cttctctcaa caacatgatg    660

ggctctgttt tcggccgagt ttacgacctc tctgactcgg ctaacaatga cgtccaagaa    720

ctccagagcc tcgtcgacga aggctacgac ttgctgggcc tcctcaactg gtccgaccat    780

ctcccatggc tcgccgactt cgactctcag aaaatccggt tcagatgctc ccgactcgtc    840

cccaaggtga accacttcgt cggccggatc atcgccgaac accgcgccaa atccgacaac    900

caagtcctag atttcgtcga cgttttgctc tctctccaag aagccgacaa actctctgac    960

tccgatatga tcgccgttct ttgggaaatg atttttcgtg ggacggacac ggtggcagtt   1020

ttaatcgagt ggatactggc caggatggta cttcacaacg atatccaaag gaaagttcaa   1080

gaggagctag ataacgtggt tgggagtaca cgcgccgtcg cggaatccga cattccgtcg   1140

ctggtgtatc taacggctgt ggttaaggaa gttctgaggt tacatccgcc gggcccactc   1200

ctgtcgtggg cccgcctagc catcactgat acaatcatcg atgggcatca cgtgccccgg   1260

gggaccaccg ctatggttaa catgtggtcg atagcgcggg acccacaggt ctggtcggac   1320

ccactcgaat ttatgcccca gaggtttgtg tccgaccccg gtgacgtgga gttctcggtc   1380

atgggttcgg atctccggct ggctccgttc gggtcgggca gaaggacctg ccccgggaag   1440
```

```
gccttcgcct ggacaactgt caccttctgg gtggccacgc ttttacacga cttcaaatgg   1500

tcgccgtccg atcaaaacga cgccgtcgac ttgtcggagg tcctcaagct ctcctgcgag   1560

atggccaatc ccctcaccgt taaagtacac ccaaggcgca gtttaagctt ttaa         1614


<210> SEQ ID NO 9
<211> LENGTH: 1506
<212> TYPE: DNA
<213> ORGANISM: Siraitia grosvenorii

<400> SEQUENCE: 9

atggatggtt ttcttccaac agtggcggcg agcgtgcctg tgggagtggg tgcaatattg     60

ttcacggcgt tgtgcgtcgt cgtgggaggg gttttggttt atttctatgg accttactgg    120

ggagtgagaa gggtgcctgg tccaccagct attccactgg tcggacatct tcccttgctg    180

gctaagtacg gcccagacgt ttctctgtc cttgccaccc aatatggccc tatcttcagg    240

ttccatatgg gtaggcagcc attgataatt atagcagacc ctgagctttg taaagaagct    300

ggtattaaga aattcaagga catcccaaat agaagtgtcc cttctccaat atcagcttcc    360

cctcttcatc agaagggtct tttcttcaca agggatgcaa gatggtcgac aatgcggaac    420

acgatattat cggtctatca gtcctcccat ctagcgagac taatacctac tatgcaatca    480

atcattgaaa ctgcaactca aaatctccat tcctctgtcc aggaagacat ccctttctcc    540

aatctctccc tcaaattgac caccgatgtg attggaacag cagccttcgg tgtcaacttt    600

gggctctcta atccacaggc aaccaaaact tgtgctacca acggccaaga caacaaaaat    660

gacgaagttt cagacttcat caatcaacac atctactcca caacgcagct caagatggat    720

ttatcaggtt ccttctcaat catacttgga ctgcttgtcc ctatactcca agaaccattt    780

agacaagtcc taaagagaat accattcacc atggactgga aagtggaccg gacaaatcag    840

aaattaagtg gtcggcttaa tgagattgtg gagaagagaa tgaagtgtaa cgatcaaggt    900

tcaaaagact tcttatcgct cattttgaga gcaagagagt cagagacagt atcaaggaat    960

gtcttcactc cagactacat cagtgcagtt acgtatgaac acctacttgc tgggtcggct   1020

accacggcgt ttacgttgtc ttctattgta tatttagttg ctgggcatcc agaagtcgag   1080

aagaagttgc tagaagagat tgacaacttt ggtccatccg atcagatacc aacagctaat   1140

gatcttcatc agaagtttcc atatcttgat caggtgatta aagaggctat gaggttctac   1200

actgtttccc ctctagtagc cagagaaaca gctaaagatg tggagattgg tggatatctt   1260

cttccaaagg ggacatgggt ttggttagca cttggagttc ttgccaagga tccaaagaac   1320

tttccagaac cagataaatt caaaccagag aggtttgatc caaatgaaga agaggagaaa   1380

caaaggcatc cttatgcttt aatccccttt ggaattggtc ctcgagcatg cattggtaaa   1440

aaattcgccc ttcaggagtt gaagctctcg ttgattcatt tgtacaggaa gtttgtattt   1500

cggcat                                                              1506


<210> SEQ ID NO 10
<211> LENGTH: 1566
<212> TYPE: DNA
<213> ORGANISM: Siraitia grosvenorii

<400> SEQUENCE: 10

atggaaatca ttttatcata tctcaacagc tccatagctg gactcttcct cttgcttctc     60

ttctcgtttt ttgttttgaa aaaggctaga acctgtaaac gcagacagcc tcctgaagca    120
```

-continued

```
gccggcggat ggccgatcat cggccacctg agactgctcg ggggttcgca acttccccat    180

gaaaccttgg gagccatggc cgacaagtat ggaccaatct tcagcatccg agttggtgtc    240

cacccatctc ttgttataag cagttgggaa gtggctaaag agtgctacac caccctcgac    300

tcagttgtct cttctcgtcc caagagtttg ggtggaaagt tgttgggcta caacttcgcc    360

gcttttgggt tcaggcctta tgattccttt taccggagta tccgcaaaac catagcctcc    420

gaggtgctgt cgaaccgccg tctggagttg cagagacaca ttcgagtttc tgaggtgaag    480

agatcggtga aggagcttta caatctgtgg acgcagagag aggaaggctc agaccacata    540

cttattgatg cggatgaatg gattggtaat attaatttga acgtgattct gatgatggtt    600

tgtgggaagc ggtttcttgg cggttctgcc agcgatgaga aggagatgag gcggtgtctc    660

aaagtctcga gagatttctt cgatttgaca gggcagttta cggtgggaga tgccattcct    720

ttcctgcgat ggctggattt gggtggatat gcgaaggcga tgaagaaaac tgcaaaagaa    780

atggactgtc tcgttgagga atggctggaa gaacaccgcc ggaagagaga ctccggcgcc    840

accgacggtg aacgtgactt catggatgtg atgctttcga ttcttgaaga gatggacctt    900

gctggctacg acgctgacac agtcaacaaa gccacatgcc tgagcattat ttctgggga     960

atcgatacta taacgctaac tctgacatgg gcgatctcgt tattgctgaa caatcgagag   1020

gcactgcgaa gggttcaaga ggaggtggac atccatgtcg gaaacaaaag gcttgtggat   1080

gaatcagact tgagcaagct ggtgtatctc caagccgtcg tgaaagagac attaaggttg   1140

tacccagcag ggccgctgtc gggagctcga gagttcagtc gggactgcac ggtcggaggg   1200

tatgacgtgg ccgccggcac acggctcatc acaaaccttt ggaagataca gacggaccct   1260

cgggtgtggc cggagccact tgagttcagg ccggagaggt ttctgagcag ccaccagcag   1320

ttggatgtga agggccagaa ctttgaactg gccccatttg gttgtggaag aagagtgtgc   1380

cctggggcgg ggcttggggt tcagatgacg cagttggtgc tggcgagtct gattcattcg   1440

gtggaacttg gaactcgctc cgatgaagcg gtggacatgg ctgctaagtt tggactcaca   1500

atgtacagag ccacccctct tcaggctctc gtcaagccac gcctccaagc cggtgcttat   1560

tcatga                                                              1566
```

<210> SEQ ID NO 11
<211> LENGTH: 1425
<212> TYPE: DNA
<213> ORGANISM: Siraitia grosvenorii

<400> SEQUENCE: 11

```
atgggtgtat tgtccatttt attattcaga tattccgtca agaagaagcc attaagatgc     60

ggtcacgatc aaagaagtac cacagatagt ccacctggtt caagaggttt gccattgata    120

ggtgaaactt tgcaattcat ggctgctatt aattctttga acggtgtata cgatttcgtt    180

agaataagat gtttgagata cggtagatgc tttaagacaa gaatcttcgg tgaaacccat    240

gtttttgtct caactacaga atccgctaag ttgatcttga aggatggtgg tgaaaaattc    300

accaaaaagt acatcagatc aatcgctgaa ttggttggtg acagaagttt gttatgtgca    360

tctcatttgc aacacaagag attgagaggt ttgttgacta atttgttttc tgccacattc    420

ttggcttctt tcgtaactca attcgatgaa caaatcgttg aagcttttag atcatgggaa    480

tccggtagta ccataatcgt tttgaacgaa gcattgaaga tcacttgtaa ggccatgtgc    540

aaaatggtca tgtccttaga aagagaaaac gaattggaag ctttgcaaaa ggaattgggt    600

catgtttgtg aagctatgtt ggcatttcca tgcagattcc ctggtacaag atttcacaat    660
```

```
ggtttgaagg caagaagaag aatcattaaa gttgtcgaaa tggccattag agaaagaaga    720
agatctgaag ctcctagaga agatttcttg caaagattgt tgacagaaga aaaggaagaa    780
gaagacggtg gtggtgtttt aagtgatgcc gaaattggtg acaacatatt gacaatgatg    840
atcgcaggtc aagataccac tgcctctgct attacctgga tggtcaagtt tttggaagaa    900
aaccaagatg tattgcaaaa cttaagagac gaacaattcg aaatcatggg taaacaagaa    960
ggttgtggtt catgcttctt gacattagaa gatttgggta atatgtccta tggtgcaaaa   1020
gtagttaagg aatcattgag attagcctcc gtcgtaccat ggtttcctag attggtttta   1080
caagattctt tgatccaagg ttacaaaatt aaaaagggtt ggaacgtcaa catagacgta   1140
agatctttac attcagatcc atccttgtat aatgacccaa caaagtttaa ccctagtaga   1200
ttcgatgacg aagctaaacc ttactcattt ttggcattcg gtatgggtgg tagacaatgt   1260
ttgggtatga acatggcaaa ggccatgatg ttggttttct tgcacagatt ggtcacctca   1320
ttcagatgga aggttataga ttccgactct tcaatcgaaa aatgggcttt gttctctaag   1380
ttgaagtcag gttgccctat cgtagttacc cacatcggtt cctaa                   1425
```

<210> SEQ ID NO 12
<211> LENGTH: 1509
<212> TYPE: DNA
<213> ORGANISM: Siraitia grosvenorii

<400> SEQUENCE: 12

```
atggatttct actggatctg tgttcttctg ctttgcttcg catggttttc cattttatcc     60
cttcactcga gaacaaacag cagcggcact tccaaacttc ctcccggacc gaaacccttg    120
ccgatcatcg gaagcctttt ggctctcggc cacgagcccc acaagtcttt ggctaatctc    180
gctaaatctc atggccctct tatgacctta aagctcggcc aaatcaccac cgtcgtagtt    240
tcctccgctg ccatggctaa gcaagttctc caaacgcacg accagtttct gtccagcagg    300
accgttccag acgcaatgac ctctcacaac cacgatgctt tcgcactccc atggattccg    360
gtttcacccc tctggcgaaa ccttcgacga atatgcaaca accagttgtt tgccggcaag    420
attctcgacg ccaacgagaa tctccggcga accaaagtgg ccgagctcgt atccgatatc    480
tcgagaagtg cattgaaagg tgagatggtg gattttggaa acgtggtgtt cgtcacttcg    540
ctcaatctgc tttccaatac gattttctcg gtggatttct tcgacccaaa ttctgaaatt    600
gggaaagagt tcaggcacgc agtacgaggc ctcatggaag aagctgccaa accaaatttg    660
ggggattatt tccctctgct gaagaagata gatcttcaag gaataaagag gagacagacc    720
acttacttcg atcgggtttt taatgttttg gagcacatga tcgaccagcg tcttcagcag    780
cagaagacga cgtctggttc tacctccaac aacaacaacg acttactgca ctaccttctc    840
aacctcagca acgaaaatag cgacatgaaa ttggggaaac ttgagctgaa acacttctta    900
ttggtgctat tcgtcgctgg gactgaaacg agttctgcaa cactgcaatg ggcaatggca    960
gaactactaa gaaacccaga aaagttagca aaagctcaag cggagaccag gcgggtgatt   1020
gggaaaggga acccaattga agaatcagac atttcgaggc tgccttatct gcaagcagtg   1080
gtgaaagaaa ctttcagatt gcacacacca gcgccatttc tactgccgcg caaagcacta   1140
caggacgtgg aaattgcagg tttcacagtc ccaaaggacg ctcaggtact ggtaaattta   1200
tgggctatga gcagagattc aagcatctgg gagaacccag agtggttcga gccagaaagg   1260
tttttggagt cggagctgga cgttagaggg agagattttg agctgatccc gttcggcggt   1320
```

gggcggagga tttgccccgg tctgccgttg gcgatgagaa tgttgcattt gattttgggt 1380
tctctcatcc acttctttga ttggaagctt gaagatgggt gtcggccgga agacgtgaaa 1440
atggacgaaa agcttggcct cactctggag ttggcttttc ccctcacagc cttgcctgtc 1500
cttgtctaa 1509

<210> SEQ ID NO 13
<211> LENGTH: 1734
<212> TYPE: DNA
<213> ORGANISM: Siraitia grosvenorii

<400> SEQUENCE: 13
atgtcctcct gcggtggtcc aactcctttg aatgttatcg gtatcttatt acaatcagaa 60
tcctccagag cctgcaactc agacgaaaac tcaagaattt tgagagattt cgtaacaaga 120
gaagttaacg ctttcttatg gttgtccttg atcactatca cagcagtttt gatcagtaaa 180
gttgtcggtt tgtttagatt gtggtctaag gcaaagcaat tgagaggtcc accttgtcca 240
tcattctacg gtcattctaa gatcatctca agacaaaatt tgactgattt gttatatgac 300
tcccacaaaa agtacggtcc agtagttaaa ttgtggttag gtcctatgca attgttagtc 360
tccgtaaagg aaccaagttt gttgaaggaa atattggtta aagctgagga taagttgcct 420
ttaacaggta gagcctttag attggctttc ggtagatctt cattatttgc atccagtttc 480
gaaaaggttc aaaacagaag acaaagattg gccgaaaagt tgaataagat cgcattccaa 540
agagccaaca tcattccaga aaaggccgta gcttgtttca tgggtagagt tcaagatttg 600
atgatagaag aatctgtcga ctgtaataag gtttctcaac atttggcttt tactttgtta 660
ggttgcacat tgtttggtga cgccttctta ggttggtcta aggctacaat ctatgaagaa 720
ttgttgatga tgatcgctaa ggacgcatcc ttttgggcta gttatagagt taccccaatc 780
tggaagcaag gtttctggag ataccaaaga ttgtgtatga agttgaagtg cttgactcaa 840
gatatcgttc aacaatacag aaagcattac aagttgtttt ctcactcaca aaaccaaaac 900
ttacacaacg aaaccaagtc aactggtgtt gaagtcgctt ttgatattcc accttgtcct 960
gctgcagacg ttagaaattc ttgctttttc tacggtttga acgatcatgt taacccaaac 1020
gaagaacctt gtggtaatat tatgggtgtc atgtttcacg gttgcttgac tacaacctct 1080
ttgatcgcat caatcttgga aagattggcc actaacccag aaatccaaga aaagattaat 1140
tctgaattga acttagttca aaagggtcca gtcaaggatc atagaaagaa tgttgacaac 1200
atgcctttgt tattggcaac aatctatgaa tcagctagat tattgccagc aggtccttta 1260
ttgcaaagat gtcctttgaa gcaagatttg gttttgaaaa caggtatcac cattccagct 1320
ggtaccttgg tcgtagttcc tattaaattg gttcaaatgg atgactcttc atggggttca 1380
gatgccaatg agtttaatcc atacagattc ttgtccatgg cttgtaatgg tattgacatg 1440
atacaaagaa ccccttttagc tggtgaaaac attggtgacc aaggtgaagg ttcatttgtc 1500
ttgaatgacc caattggtaa cgtaggtttc ttaccttttg gtttcggtgc aagagcctgc 1560
gttggtcaaa agtttataat ccaaggtgtc gctactttgt tcgcaagttt gttggcccat 1620
tacgaaatta aattgcaatc cgagagtaag aatgattcta aaccatccag taacacctct 1680
gccagtcaaa tcgtcccaaa ctcaaaaatc gtattcgtaa gaagaaactc ataa 1734

<210> SEQ ID NO 14
<211> LENGTH: 1422
<212> TYPE: DNA
<213> ORGANISM: Siraitia grosvenorii

<400> SEQUENCE: 14
atgtggactg tcgtgctcgg tttggcgacg ctgtttgtcg cctactacat ccattggatt 60
aacaaatgga gagattccaa gttcaacgga gttctgccgc cgggcaccat gggtttgccg 120
ctcatcggag agacgattca actgagtcga cccagtgact ccctcgacgt tcaccctttc 180
atccagaaaa aagttgaaag atacgggccg atcttcaaaa catgtctggc cggaaggccg 240
gtggtggtgt cggcggacgc agagttcaac aactacataa tgctgcagga aggaagagca 300
gtggaaatgt ggtatttgga tacgctctcc aaatttttcg gcctcgacac cgagtggctc 360
aaagctctgg gcctcatcca caagtacatc agaagcatta ctctcaatca cttcggcgcc 420
gaggccctgc gggagagatt tcttcctttt attgaagcat cctccatgga agcccttcac 480
tcctggtcta ctcaacctag cgtcgaagtc aaaaatgcct ccgctctcat ggtttttagg 540
acctcggtga ataagatgtt cggtgaggat gcgaagaagc tatcgggaaa tatccctggg 600
aagttcacga agcttctagg aggatttctc agtttaccac tgaattttcc cggcaccacc 660
taccacaaat gcttgaagga tatgaaggaa atccagaaga agctaagaga ggttgtagac 720
gatagattgg ctaatgtggg ccctgatgtg gaagatttct tggggcaagc ccttaaagat 780
aaggaatcag agaagttcat ttcagaggag ttcatcatcc aactgttgtt ttctatcagt 840
tttgctagct ttgagtccat ctccaccact cttactttga ttctcaagct ccttgatgaa 900
cacccagaag tagtgaaaga gttggaagct gaacacgagg cgattcgaaa agctagagca 960
gatccagatg gaccaattac ttgggaagaa tacaaatcca tgacttttac attacaagtc 1020
atcaatgaaa ccctaaggtt ggggagtgtc acacctgcct tgttgaggaa aacagttaaa 1080
gatcttcaag taaaaggata cataatcccg gaaggatgga caataatgct tgtcaccgct 1140
tcacgtcaca gagacccaaa agtctataag gaccctcata tcttcaatcc atggcgttgg 1200
aaggacttgg actcaattac catccaaaag aacttcatgc cttttggggg aggcttaagg 1260
cattgtgctg gtgctgagta ctctaaagtc tacttgtgca ccttcttgca catcctctgt 1320
accaaatacc gatggaccaa acttggggga ggaaggattg caagagctca tatattgagt 1380
tttgaagatg ggttacatgt gaagttcaca cccaaggaat ga 1422

<210> SEQ ID NO 15
<211> LENGTH: 1374
<212> TYPE: DNA
<213> ORGANISM: Siraitia grosvenorii

<400> SEQUENCE: 15
atgaagatga agatggaatc catgcgcacc tccctggata tctccgacca tgacatactt 60
ccaagggttt atcctcatgt tcacctatgg atcaacaaat atgggaaaaa cttcattcag 120
tggaatggca acgtagctca gttgattgtt tcggatcctg acacgatcaa ggagatactc 180
caaaaccgag aacaagctgt tcccaaaata gatctcagcg gagatgcacg gaggatattc 240
gggaatgggc tttcgacttc tgacggtgaa aaatgggcta aggctcgaag aatcgctgat 300
tacgctttcc acggggatct cctaagaaat atggggccaa ccatggtttc ctgtgctgag 360
gcaatggtgg aaaagtggaa gcatcatcaa ggcaaagagc ttgatttgtt cgaagagttt 420
aaggtgctca cttcagatat cattgcacat acagcctttg gaagcagtta tttggaaggg 480
aaagttattt ttcagactct aagtaagctg agcatgatat tatttaagaa tcagttcaaa 540
cgaaggattc ctgttatcag caagttcttc agatcaaagg atgcgaggga gggagaggag 600

```
ctggaaagaa ggttgaaaaa ttccataatt tcaataatgg aaaagagaga agagaaggtg    660
ataagtggtg aagcagataa ctatggtaat gattttcttg gattactttt gaaggcaaag    720
aatgagcctg accagaggca gaggatttct gttgatgatg tagtggatga atgcaaaaca    780
gtttacttcg ctgggcaaga aactacaagt gttttgcttg cttggaccgc ctttctttta    840
gcaactcatg agcattggca agaagaagca agaaaggaag tgctgaatat gtttggcaac    900
aagaatccaa ctttagaagg catcacaaaa ttaaagatta tgagcatgat catcaaggaa    960
tctctaagat tatatcctcc agccccgccc atgtcaagga aggttaaaaa ggaagtcaga   1020
ttggggaagc tggttctccc ccccaacatt caagtaagca tctcaactat tgcagttcat   1080
catgatactg caatatgggg tgaagatgcc catgtattca aaccagaaag attttctgaa   1140
ggaacagcta aagatatccc atcagctgca tacatcccat ttggctttgg tcctcgaaac   1200
tgcatcggca atatcttggc catcaacgaa actaagattg cactgtcgat gattctacaa   1260
cgattttctt tcaccatctc cccggcctac gtccacgcac ctttccagtt cctcactatc   1320
tgcccccaac acggggttca ggtaaagctt cagtccctat taagtgaaag gtga         1374
```

<210> SEQ ID NO 16
<211> LENGTH: 1590
<212> TYPE: DNA
<213> ORGANISM: Siraitia grosvenorii

<400> SEQUENCE: 16

```
atggaagctg aatttggtgc cggtgctact atggtattat ccgttgtcgc aatcgtcttc     60
tttttcacat ttttacactt gtttgaatct ttctttttga agccagatag attgagatct    120
aagttgagaa agcaaggtat tggtggtcca tctccttcat ttttgttggg taatttgtca    180
gaaattaaat ccatcagagc tttgtcttca caagctaaga acgcagaaga tgcctctgct    240
ggtggtggtg gtggttccgc cagtatagct catggttgga cttcaaattt gtttcctcac    300
ttagaacaat ggagaaacag atatggtcca attttcgtat actccagtgg tacaatccaa    360
atcttgtgta tcacagaaat ggaaaccgtt aaggaaatct ctttgtcaac ctccttgagt    420
ttaggtaaac ctgctcattt gtctaaggat agaggtccat tgttaggttt gggtatctta    480
gcctcttcag gtcctatttg ggttcaccaa agaaagatca tcgctccaca attgtatttg    540
gataaagtaa agggtatgac ctcattgatg gttgaaagtg caaattctat gttaagatcc    600
tgggaaacta aagttgaaaa tcatggtggt caagccgaaa ttaacgtcga tggtgacttg    660
agagcattaa gtgccgatat catttctaag gcttgctttg gttcaaacta ttccgaaggt    720
gaagaaattt tcttgaagtt gagagcattg caagttgtca tgagtaaggg ttctattggt    780
atacctggtt ttagatacat accaactaaa aataacagag aaatgtggaa gttggaaaag    840
gaaatcgaat caatgatctt gaaggttgcc aacgaaagaa cacaacattc cagtcacgaa    900
caagatttgt tgcaaatgat tttggaaggt gcaaagtctt tgggtgaaga caataagagt    960
atgaacatat caagagacaa gtttattgtt gacaattgta agaacatcta tttcgctggt   1020
catgaaacta cagctataac cgcatcttgg tgcttgatgt tgttagctgc acaccctgat   1080
tggcaagcaa gagccagatc tgaagtttta caatgttgcg atgacagacc aatcgatgca   1140
gacacagtca aaaatatgaa gaccttgact atggtaattc aagaaacttt gagattgtac   1200
ccacctgctg tattcgttac aagacaagca ttagaagata tcagattcaa aaacatcaca   1260
ataccaaagg gtatgaactt tcatatacca atccctatgt tgcaacaaga cttccactta   1320
tggggtcctg atgcttgttc atttgaccca caaagattct ccaatggtgt cttaggtgca   1380
```

-continued tgcaaaaacc cacaagccta tatgcctttt ggtgttggtc caagagtctg tgccggtcaa 1440
catttcgcta tgatcgaatt gaaagtcatc gtatcattgg ttttgtccag attcgaattt 1500
tctttgtcac cttcctacaa gcattcacca gccttcagat tagttgtcga accagaaaac 1560
ggtgtcatat tgcatgtcag aaagttgtga 1590

<210> SEQ ID NO 17
<211> LENGTH: 1554
<212> TYPE: DNA
<213> ORGANISM: Siraitia grosvenorii

<400> SEQUENCE: 17
atggaagtgg atatcaatat cttcaccgtc ttttccttcg tattatgcac agtcttcctc 60
ttctttctat ccttcttgat cctcctcctc ctccgaacgc tcgccggaaa atccataacg 120
agctccgagt acacgccagt gtacggcacc gtctacggtc aggctttcta tttcaacaac 180
ctgtacgatc atctaacgga ggtggccaag agacatcgaa ccttccggct gcttgcgccg 240
gcatacagcg agatatacac gaccgatccg agaaacatcg agcatatgtt gaagacgaaa 300
ttcgataagt attcgaaagg aagcaaggat caagaaatcg ttggggatct gtttggagag 360
gggatatttg cagtcgatgg agataagtgg aagcagcaga ggaagctggc tagctatgaa 420
ttctcgacga ggattcttag ggattttagc tgctcggttt tcagacgaag tgctgctaaa 480
cttgttggag ttgtttcgga gttttccagc atgggtcggg tttttgatat ccaggatttg 540
ctaatgcggt gcgctttgga ctccattttc aaagtggggt tcggggttga tttgaattgc 600
ttggaggaat caagcaaaga agggagcgat ttcatgaaag ccttcgatga ttctagcgct 660
cagatttttt ggcgctatat cgatcccttc tggaaattga agagattgct taacatcggt 720
tccgaagctt cgtttaggaa caacataaaa accatagatg cttttgtgca ccagttgatc 780
agagacaaga gaaaattgct tcagcaaccg aatcacaaga atgacaaaga ggacatactt 840
tggaggtttc tgatggaaag tgagaaggat ccaacaagaa tgaatgatca atatctaagg 900
gatatagtcc tcaatttcat gttggctggc aaagattcaa gtggaggaac tctgtcctgg 960
ttcttctaca tgctatgcaa gaaccccttta atacaggaaa aagttgcaga agaagtgagg 1020
caaattgttg cgtttgaagg ggaagaagtt gacatcaatt tgttcataca aaacttaact 1080
gattcagctc ttgacaaaat gcattatctt catgcagcat tgaccgagac tctgaggcta 1140
tatcctgcag tccctttgga tggaaggact gcagaaatag atgacattct tcctgatggc 1200
tataaactaa gaaaagggga tggagtatac tacatggcct attccatggg caggatgtcc 1260
tccctttggg gagaagatgc tgaagatttt aaacccgaaa gatggcttga aagtggaact 1320
tttcaacccg aatcaccttt caaattcatc gcttttcatg cgggtcctcg aatgtgtttg 1380
ggaaaagagt ttgcttatcg acaaatgaag atagtatctg ctgctttgct tcaatttttt 1440
cgattcaaag tagctgatac aacgaggaat gtgacttata ggatcatgct taccettcac 1500 attgatggag gtctccctct tcttgcaatt ccgagaatta gaaaatttac ctaa 1554

<210> SEQ ID NO 18
<211> LENGTH: 1686
<212> TYPE: DNA
<213> ORGANISM: Siraitia grosvenorii

<400> SEQUENCE: 18
ttggatagtg gagttaaaag agtgaaacgg ctagttgaag agaaacggcg agcagaattg 60

```
tctgcccgga ttgcctctgg agaattcaca gtcgaaaaag ctggttttcc atctgtattg    120
aggagtggct tatcaaagat gggtgttccc agtgagattc tggacatatt atttggtttc    180
gttgatgctc aagaagaata tcccaagatt cccgaagcaa aaggatcagt aaatgcaatt    240
cgtagtgagg ccttcttcat acctctctat gagctttatc tcacatatgg tggaatattt    300
aggttgactt ttgggccaaa gtcattcttg atagtttctg atccttccat tgctaaacat    360
atactgaagg ataatccgag gaattattct aagggtatct tagctgaaat tctagagttt    420
gtcatgggga agggacttat accagctgac gagaagatat ggcgtgtacg aaggcgggct    480
atagtcccat ctttgcatct gaagtatgta ggtgctatga ttaatctttt tggagaagct    540
gcagataggc tttgcaagaa gctagatgct gcagcatctg atggggttga tgtggaaatg    600
gagtccctgt tctcccgttt gactttagat atcattggca aggcagtttt taactatgac    660
tttgattcac ttacaaatga cactggcata gttgaggctg tttacactgt gctaagagaa    720
gcagaggatc gcagtgttgc accaattcca gtatgggaaa ttccaatttg gaaggatatt    780
tcaccacggc aaaaaaaggt ctctaaagcc ctcaaattga tcaacgacac cctcgatcaa    840
ctaattgcta tatgcaagag gatggttgat gaggaggagc tgcagtttca tgaggaatac    900
atgaatgagc aagatccaag catccttcat ttccttttgg catcaggaga tgatgtttca    960
agcaagcagc ttcgtgatga cttgatgact atgcttatag ctgggcatga aacatctgct   1020
gcagttttaa catggacctt ttatcttctt tccaaggagc cgaggatcat gtccaagctc   1080
caggaggagg ttgattcagt ccttggggat cggtttccaa ctattgaaga tatgaagaac   1140
ctcaaatatg ccacacgaat aattaacgaa tccttgaggc tttacccaca gccaccagtt   1200
ttaatacgtc gatctcttga caatgatatg ctcgggaagt accccattaa aaagggtgag   1260
gacatattca tttctgtttg gaacttgcat cgcagtccaa aactctggga tgatgcggat   1320
aaatttaatc ctgaaaggtg gcctctggat ggacccaatc caaatgagac aaatcaaaat   1380
ttcagatatt taccttttgg tggcggacca cggaaatgtg tgggagacat gtttgcttcg   1440
tacgagactg ttgtagcact tgcaatgctt gttcggcgat ttgacttcca aatggcactt   1500
ggagcacctc ctgtaaaaat gacaactgga gctacaattc acacaacaga tggattgaaa   1560
atgacagtta cacgaagaat gagacctcca atcataccca cattagagat gcctgcagtg   1620
gtcgttgact cgtctgtcgt ggactcgtcc gtcgccattt tgaaagaaga aacacaaatt   1680
ggttag                                                              1686
```

<210> SEQ ID NO 19
<211> LENGTH: 1299
<212> TYPE: DNA
<213> ORGANISM: Siraitia grosvenorii

<400> SEQUENCE: 19

```
cagttcctct cctggtcctc ccagtttggc aagaggttca tcttctggaa tgggatcgag     60
cccagaatgt gcctcaccga gaccgatttg atcaaagagc ttctctctaa gtacagcgcc    120
gtctccggta agtcatggct tcagcaacag ggctccaagc acttcatcgg ccgcggtctc    180
ttaatggcca acggccaaaa ctggtaccac cagcgtcaca tcgtcgcgcc ggccttcatg    240
ggagacagac tcaagagtta cgccgggtac atggtggaat gcacaaagga gatgcttcag    300
tcaattgaaa acgaggtcaa ctcggggcga tccgagttcg aaatcggtga gtatatgacc    360
agactcaccg ccgatataat atcacgaacc gagttcgaaa gcagctacga aaagggaaag    420
caaattttcc atttgctcac cgttttacag catctctgcg ctcaggcgag ccgccacctc    480
```

```
tgccttcctg gaagccggtt ttttccgagt aaatacaaca gagagataaa ggcattgaag    540
acgaaggtgg aggggttgtt aatggagata atacagagca gaagagactg tgtggaggtg    600
gggaggagca gttcgtatgg aaatgatctg ttgggaatgt tgctgaatga gatgcagaag    660
aagaaagatg ggaatgggtt gagcttgaat ttgcagatta taatggatga atgcaagacc    720
ttcttcttcg ccggccatga aaccactgct cttttgctca cttggactgt aatgttattg    780
gccagcaacc cttcttggca acacaaggtt cgagccgaag ttatggccgt ctgcaatgga    840
ggaactctct ctcttgaaca tctctccaag ctctctctgt tgagtatggt gataaatgaa    900
tcgttgaggc tatacccgcc agcaagtatt cttccaagaa tggcatttga agatataaag    960
ctgggagatc ttgagatccc aaaagggctg tcgatatgga tcccagtgct tgcaattcac   1020
cacagtgaag agctatgggg caaagatgca aatgagttca acccagaaag atttgcaaat   1080
tcaaaagcct tcacttcggg gagattcatt ccctttgctt ctggccctcg caactgcgtt   1140
ggccaatcat ttgctctcat ggaaaccaag atcattttgg ctatgctcat ctccaagttt   1200
tccttcacca tctctgacaa ttatcgccat gcacccgtgg tcgtcctcac tataaaaccc   1260
aaatacggag tccaagtttg cttgaagcct ttcaattaa                          1299
```

<210> SEQ ID NO 20
<211> LENGTH: 1506
<212> TYPE: DNA
<213> ORGANISM: Siraitia grosvenorii

<400> SEQUENCE: 20

```
atggaagaca ccttcctact ctatccttcc ctctctcttc tctttcttct ttttgctttc     60
aagctcatcc gtcgatccgg aggagttcgc aggaacttac cgccgagtcc gccctctctt    120
ccggttatcg gccacctcca tctcttgaaa aagccactcc accggacttt ccagaaactt    180
tccgccaaat atggtcctgt tatgtccctc cgcctcgggt ctcgcctcgc agtcattgta    240
tcgtcgtcgt cggcggtgga cgagtgtttc actaaaaacg acgtcgtgct cgccaaccgt    300
cctcgtttgc taattggcaa acacctcggc tacaactaca ctaccatggt tggggctccc    360
tacggcgacc actggcgtag cctccgccgc atcggtgccc tcgaaatctt ctcttcatct    420
cgcctcaaca aattcgccga catccgaagg gatgaagtag agggattgct tcgcaaactc    480
tcacgcaatt cgctccatca attctcgaaa gtggaagttc aatcggcctt gtcggagctg    540
acgttcaaca tctcgatgag aatggcggca gggaaacggt attacggaga tgacgtgacg    600
gacgaggaag aggcgagaaa gttcagagag ttaattaaac agatagtggc gctgggcgga    660
gtatcaaatc caggggattt cgtcccgatt ctgaattgga ttccgaacgg tttcgagagg    720
aagttgatcg agtgtgggaa gaagacggat gcgttcttgc aggggctgat cgaggaccac    780
cggagaaaga aggaagaggg taggaacacg atgatcgatc acctgctctc tctgcaagaa    840
tcggagcctg ctcactacgg agaccaaata atcaaaggat ttatactggt gttactgacg    900
gcggggaccg atacatcggc cgtgacaatg gagtgggcgc tatctcatct cctgaacaat    960
cctgaagtgc taaagaaggc aagagatgag gtcgacactg aaattggaca agaacgactt   1020
gtcgaagaat cagacgtagt atctaagtta ccctatcttc aagggatcat ctccgagact   1080
ctccggctga atcccgccgc tccgatgttg ttgccccatt acgcctcgga cgactgcacg   1140
atatgtggat acgacgtgcc acgtgacaca atcgtaatgg tcaatgcatg ggccatacat   1200
agggatccaa acgaatggga ggagcccacg tgtttcagac cagaacgata tgaaaagtcg   1260
```

tcgtcggaag cggaggtaca caagtcggtg agtttcgggg tgggaaggcg agcttgtcct 1320
gggtctggca tggcgcagag ggtgatgggc ttgactttgg cggcactggt tcagtgcttc 1380
gagtgggaga gagttggaga agaagaagtg gacatgaacg aaggctcagg tgccacaatg 1440
cccaagatgg tgccattgga ggccatgtgc agagctcgtc ccatcgtcca caaccttctt 1500
tactga 1506

<210> SEQ ID NO 21
<211> LENGTH: 496
<212> TYPE: PRT
<213> ORGANISM: Arabidopsis thaliana

<400> SEQUENCE: 21

Met Ala Thr Glu Lys Thr His Gln Phe His Pro Ser Leu His Phe Val
1 5 10 15

Leu Phe Pro Phe Met Ala Gln Gly His Met Ile Pro Met Ile Asp Ile
20 25 30

Ala Arg Leu Leu Ala Gln Arg Gly Val Thr Ile Thr Ile Val Thr Thr
35 40 45

Pro His Asn Ala Ala Arg Phe Lys Asn Val Leu Asn Arg Ala Ile Glu
50 55 60

Ser Gly Leu Ala Ile Asn Ile Leu His Val Lys Phe Pro Tyr Gln Glu
65 70 75 80

Phe Gly Leu Pro Glu Gly Lys Glu Asn Ile Asp Ser Leu Asp Ser Thr
85 90 95

Glu Leu Met Val Pro Phe Phe Lys Ala Val Asn Leu Leu Glu Asp Pro
100 105 110

Val Met Lys Leu Met Glu Glu Met Lys Pro Arg Pro Ser Cys Leu Ile
115 120 125

Ser Asp Trp Cys Leu Pro Tyr Thr Ser Ile Ile Ala Lys Asn Phe Asn
130 135 140

Ile Pro Lys Ile Val Phe His Gly Met Gly Cys Phe Asn Leu Leu Cys
145 150 155 160

Met His Val Leu Arg Arg Asn Leu Glu Ile Leu Glu Asn Val Lys Ser
165 170 175

Asp Glu Glu Tyr Phe Leu Val Pro Ser Phe Pro Asp Arg Val Glu Phe
180 185 190

Thr Lys Leu Gln Leu Pro Val Lys Ala Asn Ala Ser Gly Asp Trp Lys
195 200 205

Glu Ile Met Asp Glu Met Val Lys Ala Glu Tyr Thr Ser Tyr Gly Val
210 215 220

Ile Val Asn Thr Phe Gln Glu Leu Glu Pro Pro Tyr Val Lys Asp Tyr
225 230 235 240

Lys Glu Ala Met Asp Gly Lys Val Trp Ser Ile Gly Pro Val Ser Leu
245 250 255

Cys Asn Lys Ala Gly Ala Asp Lys Ala Glu Arg Gly Ser Lys Ala Ala
260 265 270

Ile Asp Gln Asp Glu Cys Leu Gln Trp Leu Asp Ser Lys Glu Glu Gly
275 280 285

Ser Val Leu Tyr Val Cys Leu Gly Ser Ile Cys Asn Leu Pro Leu Ser
290 295 300

Gln Leu Lys Glu Leu Gly Leu Gly Leu Glu Glu Ser Arg Arg Ser Phe
305 310 315 320

Ile Trp Val Ile Arg Gly Ser Glu Lys Tyr Lys Glu Leu Phe Glu Trp

-continued

```
                325                 330                 335

Met Leu Glu Ser Gly Phe Glu Glu Arg Ile Lys Glu Arg Gly Leu Leu
            340                 345                 350

Ile Lys Gly Trp Ala Pro Gln Val Leu Ile Leu Ser His Pro Ser Val
        355                 360                 365

Gly Gly Phe Leu Thr His Cys Gly Trp Asn Ser Thr Leu Glu Gly Ile
    370                 375                 380

Thr Ser Gly Ile Pro Leu Ile Thr Trp Pro Leu Phe Gly Asp Gln Phe
385                 390                 395                 400

Cys Asn Gln Lys Leu Val Val Gln Val Leu Lys Ala Gly Val Ser Ala
                405                 410                 415

Gly Val Glu Glu Val Met Lys Trp Gly Glu Glu Asp Lys Ile Gly Val
            420                 425                 430

Leu Val Asp Lys Glu Gly Val Lys Lys Ala Val Glu Glu Leu Met Gly
        435                 440                 445

Asp Ser Asp Asp Ala Lys Glu Arg Arg Arg Arg Val Lys Glu Leu Gly
    450                 455                 460

Glu Leu Ala His Lys Ala Val Glu Lys Gly Gly Ser Ser His Ser Asn
465                 470                 475                 480

Ile Thr Leu Leu Leu Gln Asp Ile Met Gln Leu Ala Gln Phe Lys Asn
                485                 490                 495


<210> SEQ ID NO 22
<211> LENGTH: 495
<212> TYPE: PRT
<213> ORGANISM: Arabidopsis thaliana

<400> SEQUENCE: 22

Met Val Ser Glu Thr Thr Lys Ser Ser Pro Leu His Phe Val Leu Phe
1               5                   10                  15

Pro Phe Met Ala Gln Gly His Met Ile Pro Met Val Asp Ile Ala Arg
            20                  25                  30

Leu Leu Ala Gln Arg Gly Val Ile Ile Thr Ile Val Thr Thr Pro His
        35                  40                  45

Asn Ala Ala Arg Phe Lys Asn Val Leu Asn Arg Ala Ile Glu Ser Gly
    50                  55                  60

Leu Pro Ile Asn Leu Val Gln Val Lys Phe Pro Tyr Leu Glu Ala Gly
65                  70                  75                  80

Leu Gln Glu Gly Gln Glu Asn Ile Asp Ser Leu Asp Thr Met Glu Arg
                85                  90                  95

Met Ile Pro Phe Phe Lys Ala Val Asn Phe Leu Glu Glu Pro Val Gln
            100                 105                 110

Lys Leu Ile Glu Glu Met Asn Pro Arg Pro Ser Cys Leu Ile Ser Asp
        115                 120                 125

Phe Cys Leu Pro Tyr Thr Ser Lys Ile Ala Lys Lys Phe Asn Ile Pro
    130                 135                 140

Lys Ile Leu Phe His Gly Met Gly Cys Phe Cys Leu Leu Cys Met His
145                 150                 155                 160

Val Leu Arg Lys Asn Arg Glu Ile Leu Asp Asn Leu Lys Ser Asp Lys
                165                 170                 175

Glu Leu Phe Thr Val Pro Asp Phe Pro Asp Arg Val Glu Phe Thr Arg
            180                 185                 190

Thr Gln Val Pro Val Glu Thr Tyr Val Pro Ala Gly Asp Trp Lys Asp
        195                 200                 205
```

-continued

```
Ile Phe Asp Gly Met Val Glu Ala Asn Glu Thr Ser Tyr Gly Val Ile
    210                 215                 220

Val Asn Ser Phe Gln Glu Leu Glu Pro Ala Tyr Ala Lys Asp Tyr Lys
225                 230                 235                 240

Glu Val Arg Ser Gly Lys Ala Trp Thr Ile Gly Pro Val Ser Leu Cys
                245                 250                 255

Asn Lys Val Gly Ala Asp Lys Ala Glu Arg Gly Asn Lys Ser Asp Ile
            260                 265                 270

Asp Gln Asp Glu Cys Leu Lys Trp Leu Asp Ser Lys Lys His Gly Ser
        275                 280                 285

Val Leu Tyr Val Cys Leu Gly Ser Ile Cys Asn Leu Pro Leu Ser Gln
    290                 295                 300

Leu Lys Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335

Ser Glu Ser Gly Phe Glu Asp Arg Ile Gln Asp Arg Gly Leu Leu Ile
            340                 345                 350

Lys Gly Trp Ser Pro Gln Met Leu Ile Leu Ser His Pro Ser Val Gly
        355                 360                 365

Gly Phe Leu Thr His Cys Gly Trp Asn Ser Thr Leu Glu Gly Ile Thr
    370                 375                 380

Ala Gly Leu Pro Leu Leu Thr Trp Pro Leu Phe Ala Asp Gln Phe Cys
385                 390                 395                 400

Asn Glu Lys Leu Val Val Glu Val Leu Lys Ala Gly Val Arg Ser Gly
                405                 410                 415

Val Glu Gln Pro Met Lys Trp Gly Glu Glu Lys Ile Gly Val Leu
            420                 425                 430

Val Asp Lys Glu Gly Val Lys Lys Ala Val Glu Glu Leu Met Gly Glu
        435                 440                 445

Ser Asp Asp Ala Lys Glu Arg Arg Arg Arg Ala Lys Glu Leu Gly Asp
    450                 455                 460

Ser Ala His Lys Ala Val Glu Glu Gly Gly Ser Ser His Ser Asn Ile
465                 470                 475                 480

Ser Phe Leu Leu Gln Asp Ile Met Glu Leu Ala Glu Pro Asn Asn
                485                 490                 495
```

<210> SEQ ID NO 23
<211> LENGTH: 495
<212> TYPE: PRT
<213> ORGANISM: Arabidopsis thaliana

<400> SEQUENCE: 23

```
Met Ala Phe Glu Lys Asn Asn Glu Pro Phe Pro Leu His Phe Val Leu
1               5                   10                  15

Phe Pro Phe Met Ala Gln Gly His Met Ile Pro Met Val Asp Ile Ala
            20                  25                  30

Arg Leu Leu Ala Gln Arg Gly Val Leu Ile Thr Ile Val Thr Thr Pro
        35                  40                  45

His Asn Ala Ala Arg Phe Lys Asn Val Leu Asn Arg Ala Ile Glu Ser
    50                  55                  60

Gly Leu Pro Ile Asn Leu Val Gln Val Lys Phe Pro Tyr Gln Glu Ala
65                  70                  75                  80

Gly Leu Gln Glu Gly Gln Glu Asn Met Asp Leu Leu Thr Thr Met Glu
                85                  90                  95
```

```
Gln Ile Thr Ser Phe Phe Lys Ala Val Asn Leu Leu Lys Glu Pro Val
            100                 105                 110

Gln Asn Leu Ile Glu Glu Met Ser Pro Arg Pro Ser Cys Leu Ile Ser
        115                 120                 125

Asp Met Cys Leu Ser Tyr Thr Ser Glu Ile Ala Lys Lys Phe Lys Ile
    130                 135                 140

Pro Lys Ile Leu Phe His Gly Met Gly Cys Phe Cys Leu Leu Cys Val
145                 150                 155                 160

Asn Val Leu Arg Lys Asn Arg Glu Ile Leu Asp Asn Leu Lys Ser Asp
                165                 170                 175

Lys Glu Tyr Phe Ile Val Pro Tyr Phe Pro Asp Arg Val Glu Phe Thr
            180                 185                 190

Arg Pro Gln Val Pro Val Glu Thr Tyr Val Pro Ala Gly Trp Lys Glu
        195                 200                 205

Ile Leu Glu Asp Met Val Glu Ala Asp Lys Thr Ser Tyr Gly Val Ile
    210                 215                 220

Val Asn Ser Phe Gln Glu Leu Glu Pro Ala Tyr Ala Lys Asp Phe Lys
225                 230                 235                 240

Glu Ala Arg Ser Gly Lys Ala Trp Thr Ile Gly Pro Val Ser Leu Cys
                245                 250                 255

Asn Lys Val Gly Val Asp Lys Ala Glu Arg Gly Asn Lys Ser Asp Ile
            260                 265                 270

Asp Gln Asp Glu Cys Leu Glu Trp Leu Asp Ser Lys Glu Pro Gly Ser
        275                 280                 285

Val Leu Tyr Val Cys Leu Gly Ser Ile Cys Asn Leu Pro Leu Ser Gln
    290                 295                 300

Leu Leu Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335

Ser Glu Ser Gly Phe Glu Asp Arg Ile Gln Asp Arg Gly Leu Leu Ile
            340                 345                 350

Lys Gly Trp Ser Pro Gln Met Leu Ile Leu Ser His Pro Ser Val Gly
        355                 360                 365

Gly Phe Leu Thr His Cys Gly Trp Asn Ser Thr Leu Glu Gly Ile Thr
    370                 375                 380

Ala Gly Leu Pro Met Leu Thr Trp Pro Leu Phe Ala Asp Gln Phe Cys
385                 390                 395                 400

Asn Glu Lys Leu Val Val Gln Ile Leu Lys Val Gly Val Ser Ala Glu
                405                 410                 415

Val Lys Glu Val Met Lys Trp Gly Glu Glu Glu Lys Ile Gly Val Leu
            420                 425                 430

Val Asp Lys Glu Gly Val Lys Lys Ala Val Glu Glu Leu Met Gly Glu
        435                 440                 445

Ser Asp Asp Ala Lys Glu Arg Arg Arg Arg Ala Lys Glu Leu Gly Glu
    450                 455                 460

Ser Ala His Lys Ala Val Glu Glu Gly Gly Ser Ser His Ser Asn Ile
465                 470                 475                 480

Thr Phe Leu Leu Gln Asp Ile Met Gln Leu Ala Gln Ser Asn Asn
                485                 490                 495
```

<210> SEQ ID NO 24
<211> LENGTH: 495

<212> TYPE: PRT
<213> ORGANISM: Stevia rebaudiana

<400> SEQUENCE: 24

```
Met Ser Pro Lys Met Val Ala Pro Pro Thr Asn Leu His Phe Val Leu
1               5                   10                  15

Phe Pro Leu Met Ala Gln Gly His Leu Val Pro Met Val Asp Ile Ala
            20                  25                  30

Arg Ile Leu Ala Gln Arg Gly Ala Thr Val Thr Ile Ile Thr Thr Pro
        35                  40                  45

Tyr His Ala Asn Arg Val Arg Pro Val Ile Ser Arg Ala Ile Ala Thr
    50                  55                  60

Asn Leu Lys Ile Gln Leu Leu Glu Leu Gln Leu Arg Ser Thr Glu Ala
65                  70                  75                  80

Gly Leu Pro Glu Gly Cys Glu Ser Phe Asp Gln Leu Pro Ser Phe Glu
                85                  90                  95

Tyr Trp Lys Asn Ile Ser Thr Ala Ile Asp Leu Leu Gln Gln Pro Ala
            100                 105                 110

Glu Asp Leu Leu Arg Glu Leu Ser Pro Pro Pro Asp Cys Ile Ile Ser
        115                 120                 125

Asp Phe Leu Phe Pro Trp Thr Thr Asp Val Ala Arg Arg Leu Asn Ile
    130                 135                 140

Pro Arg Leu Val Phe Asn Gly Pro Gly Cys Phe Tyr Leu Leu Cys Ile
145                 150                 155                 160

His Val Ala Ile Thr Ser Asn Ile Leu Gly Glu Asn Glu Pro Val Ser
                165                 170                 175

Ser Asn Thr Glu Arg Val Val Leu Pro Gly Leu Pro Asp Arg Ile Glu
            180                 185                 190

Val Thr Lys Leu Gln Ile Val Gly Ser Ser Arg Pro Ala Asn Val Asp
        195                 200                 205

Glu Met Gly Ser Trp Leu Arg Ala Val Glu Ala Glu Lys Ala Ser Phe
    210                 215                 220

Gly Ile Val Val Asn Thr Phe Glu Glu Leu Glu Pro Glu Tyr Val Glu
225                 230                 235                 240

Glu Tyr Lys Thr Val Lys Asp Lys Lys Met Trp Cys Ile Gly Pro Val
                245                 250                 255

Ser Leu Cys Asn Lys Thr Gly Pro Asp Leu Ala Glu Arg Gly Asn Lys
            260                 265                 270

Ala Ala Ile Thr Glu His Asn Cys Leu Lys Trp Leu Asp Glu Arg Lys
        275                 280                 285

Leu Gly Ser Val Leu Tyr Val Cys Leu Gly Ser Leu Ala Arg Ile Ser
    290                 295                 300

Ala Ala Gln Ala Ile Glu Leu Gly Leu Gly Leu Glu Ser Ile Asn Arg
305                 310                 315                 320

Pro Phe Ile Trp Cys Val Arg Asn Glu Thr Asp Glu Leu Lys Thr Trp
                325                 330                 335

Phe Leu Asp Gly Phe Glu Glu Arg Val Arg Asp Arg Gly Leu Ile Val
            340                 345                 350

His Gly Trp Ala Pro Gln Val Leu Ile Leu Ser His Pro Thr Ile Gly
        355                 360                 365

Gly Phe Leu Thr His Cys Gly Trp Asn Ser Thr Ile Glu Ser Ile Thr
    370                 375                 380

Ala Gly Val Pro Met Ile Thr Trp Pro Phe Phe Ala Asp Gln Phe Leu
385                 390                 395                 400
```

Asn Glu Ala Phe Ile Val Glu Val Leu Lys Ile Gly Val Arg Ile Gly
405 410 415

Val Glu Arg Ala Cys Leu Phe Gly Glu Glu Asp Lys Val Gly Val Leu
420 425 430

Val Lys Lys Glu Asp Val Lys Lys Ala Val Glu Cys Leu Met Asp Glu
435 440 445

Asp Glu Asp Gly Asp Gln Arg Arg Lys Arg Val Ile Glu Leu Ala Lys
450 455 460

Met Ala Lys Ile Ala Met Ala Glu Gly Gly Ser Ser Tyr Glu Asn Val
465 470 475 480

Ser Ser Leu Ile Arg Asp Val Thr Glu Thr Val Arg Ala Pro His
485 490 495

<210> SEQ ID NO 25
<211> LENGTH: 481
<212> TYPE: PRT
<213> ORGANISM: Stevia rebaudiana

<400> SEQUENCE: 25

Met Asp Ala Met Ala Thr Thr Glu Lys Lys Pro His Val Ile Phe Ile
1 5 10 15

Pro Phe Pro Ala Gln Ser His Ile Lys Ala Met Leu Lys Leu Ala Gln
20 25 30

Leu Leu His His Lys Gly Leu Gln Ile Thr Phe Val Asn Thr Asp Phe
35 40 45

Ile His Asn Gln Phe Leu Glu Ser Ser Gly Pro His Cys Leu Asp Gly
50 55 60

Ala Pro Gly Phe Arg Phe Glu Thr Ile Pro Asp Gly Val Ser His Ser
65 70 75 80

Pro Glu Ala Ser Ile Pro Ile Arg Glu Ser Leu Leu Arg Ser Ile Glu
85 90 95

Thr Asn Phe Leu Asp Arg Phe Ile Asp Leu Val Thr Lys Leu Pro Asp
100 105 110

Pro Pro Thr Cys Ile Ile Ser Asp Gly Phe Leu Ser Val Phe Thr Ile
115 120 125

Asp Ala Ala Lys Lys Leu Gly Ile Pro Val Met Met Tyr Trp Thr Leu
130 135 140

Ala Ala Cys Gly Phe Met Gly Phe Tyr His Ile His Ser Leu Ile Glu
145 150 155 160

Lys Gly Phe Ala Pro Leu Lys Asp Ala Ser Tyr Leu Thr Asn Gly Tyr
165 170 175

Leu Asp Thr Val Ile Asp Trp Val Pro Gly Met Glu Gly Ile Arg Leu
180 185 190

Lys Asp Phe Pro Leu Asp Trp Ser Thr Asp Leu Asn Asp Lys Val Leu
195 200 205

Met Phe Thr Thr Glu Ala Pro Gln Arg Ser His Lys Val Ser His His
210 215 220

Ile Phe His Thr Phe Asp Glu Leu Glu Pro Ser Ile Ile Lys Thr Leu
225 230 235 240

Ser Leu Arg Tyr Asn His Ile Tyr Thr Ile Gly Pro Leu Gln Leu Leu
245 250 255

Leu Asp Gln Ile Pro Glu Glu Lys Lys Gln Thr Gly Ile Thr Ser Leu
260 265 270

His Gly Tyr Ser Leu Val Lys Glu Glu Pro Glu Cys Phe Gln Trp Leu

-continued

```
        275                 280                 285

Gln Ser Lys Glu Pro Asn Ser Val Val Tyr Val Asn Phe Gly Ser Thr
    290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
    370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly Gly His Lys Met Arg Asn Lys Ala Lys
        435                 440                 445

Asp Trp Lys Glu Lys Ala Arg Ile Ala Ile Ala Pro Asn Gly Ser Ser
    450                 455                 460

Ser Leu Asn Ile Asp Lys Met Val Lys Glu Ile Thr Val Leu Ala Arg
465                 470                 475                 480

Asn


<210> SEQ ID NO 26
<211> LENGTH: 1380
<212> TYPE: DNA
<213> ORGANISM: Siraitia grosvenorii

<400> SEQUENCE: 26

atggatgccc agcgaggtca caccaccacc attttgatgc ttccatgggt cggctacggc      60

catctcttgc ctttcctcga gctggccaaa agcctctcca ggaggaaatt attccacatc     120

tacttctgtt caacgtctgt tagcctcgac gccattaaac caaagcttcc tccttctatc     180

tcttctgatg attccatcca acttgtggaa cttcgtctcc cttcttctcc tgagttacct     240

cctcatcttc acacaaccaa cggccttccc tctcacctca tgcccgctct ccaccaagcc     300

ttcgtcatgg ccgcccaaca ctttcaggtc attttacaaa cacttgcccc gcatctcctc     360

atttatgaca ttctccaacc ttgggctcct caagtggctt catccctcaa cattccagcc     420

atcaacttca gtactaccgg agcttcaatg ctttctcgaa cgcttcaccc tactcactac     480

ccaagttcta aattcccaat ctcagagttt gttcttcaca atcactggag agccatgtac     540

accaccgccg atggggctct tacagaagaa ggccacaaaa ttgaagaaac acttgcgaat     600

tgcttgcata cttcttgcgg ggtagttttg gtcaatagtt tcagagagct tgagacgaaa     660

tatatcgatt atctctctgt tctcttgaac aagaaagttg ttccggtcgg tcctttggtt     720

tacgaaccga atcaagaagg ggaagatgaa ggttattcaa gcatcaaaaa ttggcttgac     780

aaaaaggaac cgtcctcaac cgtcttcgtt tcatttggaa ccgaatactt cccgtcaaag     840

gaagaaatgg aagagatagc gtatgggtta gagctgagcg aggttaattt catctgggtc     900

cttagatttc ctcaaggaga cagcaccagc accattgaag acgccttgcc gaaggggttt     960
```

ctggagagag cgggagagag ggcgatggtg gtgaagggtt gggctcctca ggcgaagata 1020
ctgaagcatt ggagcacagg ggggcttgtg agtcactgtg gatggaactc gatgatggag 1080
ggcatgatgt ttggcgtacc cataatagcg gtcccgatgc atctggacca gccctttaac 1140
gccggactct tggaagaagc tggcgtcggc gtggaagcca agcgaggttc ggacggcaaa 1200
attcaaagag aagaagttgc aaagtcgatc aaagaagtgg tgattgagaa aaccagggaa 1260
gacgtgagga agaaagcaag agaaatgggt gagattttga ggagtaaagg agatgagaaa 1320
attgatgagt tggtggctga aatttctctt ttgcgcaaaa aggctccatg ttcaatttaa 1380

<210> SEQ ID NO 27
<211> LENGTH: 1434
<212> TYPE: DNA
<213> ORGANISM: Siraitia grosvenorii

<400> SEQUENCE: 27
atgcttccat ggctggctca cggccatgtc tccccttct tcgagctcgc caagttgctc 60
gccgctagaa acttccacat attcttctgc tccaccgccg taaacctccg ctccgtcgaa 120
ccaaaactct ctcagaagct ctcctcccac gtggagctgg tggagctcaa cctaccgccc 180
tcgccggagc tccctccgca ccgccacacc accgccggcc ttccaccgca cctcatgttc 240
tcgctcaagc gagctttcga catggccgct cccgccttcg ccgccatcct ccgcgacctg 300
aacccggact tgctcatcta cgacttcctg cagccgtggg cggcggcgga ggctctgtcg 360
gcggatattc cggccgtgat gttcaaaagc acgggtgcgc tcatggcggc catggtcgcg 420
tacgagctga cgtttccgaa ctctgatttt ttctcgcttt tccctgagat tcgtctctcc 480
gagtgcgaga ttaaacagct gaagaacttg tttcaatgtt ctgtgaatga tgcgaaagac 540
aagcaaagga ttaagggatg ttatgagaga tcttgcggca tgattttggt gaaatctttc 600
agagaaatcg aaggcaaata tattgatttt ctctctactc tgctgggcaa gaaggttgtt 660
ccagttggtc cacttgttca acaaacagaa gacgacgtcg tatcaggaag ttttgacgaa 720
tggctaaatg gaaaagatag atcgtcttcc atactcgtgt ctttcggaag cgagttctac 780
ctgtccagag aagacatgga agagatcgcg catggcttag agctgagcca ggtgaacttc 840
atatgggtcg tcaggtttcc ggcgggagga gagagaaaca cgacaaaggt ggaagaagaa 900
ctgccaaaag ggtttctaga gagagttaga gagagaggga tggtggtgga gggctgggcg 960
ccgcaggctc agatcttgaa acatccaagc gtcggcggat tcctcagcca ctgcgggtgg 1020
agctccgtcg tggagagcat gaaattcggc gttccgatca tcgccatgcc gatgcacctc 1080
gaccagccgc tgaattcccg gctggtcgag cggctcggcg tcggcgtagt ggtggagaga 1140
gacggccgcc tccggggaga ggtggagaga gttgtcagag aggtggtggt ggagaaaagt 1200
ggagagagag tgaggaagaa ggtggaggag tttgcagaga tcatgaagaa gaaaaaagac 1260
aatgaagaga tggacgtagt cgtggaagag ttggtgacgc tctgcaggaa gaagaagaag 1320
gaggaggatt tacagagtaa ttattggtgc agaaccgcca ttgatgacca ttgttctgaa 1380
gtcgtgaaga ttgaagatgc tgcagcagcc gacgaggagc ctctttgcaa ataa 1434

<210> SEQ ID NO 28
<211> LENGTH: 1383
<212> TYPE: DNA
<213> ORGANISM: Siraitia grosvenorii

<400> SEQUENCE: 28

```
atggctgtca cttacagcct gcacatagca atgtaccctt ggtttgcttt cggccacttg     60
actccatttc tccaagtctc caacaagctt gccaaggaag gccacaaaat ctccttcttc    120
atcccaacga aaacgctaac caaattgcag cctttcaatc tctttccaga tctcattacc    180
tttgtcccca tcactgttcc tcatgttgat ggtctccctc ttggagctga gactactgct    240
gatgtttctc acccttcaca gctcagtctc atcatgactg ctatggattg cacccaaccc    300
gaaatcgagt gtcttcttcg agacataaaa cctgatgcca tcttcttcga tttcgcgcac    360
tgggtgccaa aattggcatg tggattgggc attaagtcga ttgattacag tgtctgttct    420
gcagtatcaa ttggttatgt tttgccccta ttaaggaaag tttgtggaca agatttatta    480
actgaagatg attttatgca gccatctcct ggctacccga gttccaccat caatcttcaa    540
gctcatgagg ctcgatattt tgcatctctg agccgctgga ggtttggcag tgatgtccct    600
ttctttagtc gccatcttac tgcacttaat gaatgcaatg ctttagcatt caggtcatgt    660
agggagattg aagggccttt tatagactat ccagaaagtg aattaaaaaa gcctgtgttg    720
ctttccggag cagtggatct acaaccgcca accacaactg tagaagaaag atgggcaaaa    780
tggctatcag ggttcaacac cgactcggtc gtatattgtg catttggaag tgagtgtacc    840
ttagcaaaag accaattcca agaactgctg ttgggttttg agctttcaaa tatgccattc    900
tttgctgcac ttaaaccacc ttttggtgtt gactcggttg aagcagcctt gcctgaaggt    960
tttgaacaga gagttcaggg aagaggggtg gtctatgggg gatgggtcca acagcagctc   1020
attttggagc acccatcaat tggatgcttt gttacacatt gtggatcagg ctccttatca   1080
gaggcgttag tgaagaagtg tcaattagtg ttgttacctc gtatcggtga ccactttttc   1140
cgagcaagaa tgttgagcaa ttatttgaaa gttggtgtgg aggtagagaa aggagaagga   1200
gatggatctt ttacaaagga aagtgtgtgg aaggcagtga agacagtgat ggatgaagag   1260
aatgaaactg ggaaagagtt cagagcgaac cgtgccaaga taagagagct attgctcgac   1320
gaagatctcg aggagtctta tatcaacaat ttcatccaca gcctgcatac tttgaatgca   1380
tga                                                                 1383
```

<210> SEQ ID NO 29
<211> LENGTH: 174
<212> TYPE: DNA
<213> ORGANISM: Artificial sequence
<220> FEATURE:
<223> OTHER INFORMATION: Partial gene sequence from Siraitia grosvenorii

<400> SEQUENCE: 29

```
atggcggatc ggaaagagag cgttgtgatg ttcccgttca tggggcaggg ccatatcatc     60
ccttttctag ctttggccct ccagattgag cacagaaaca gaaactacgc catatacttg    120
gtaaatactc ctctcaacgt taagaaaatg agatcttctc tccctccaga ttga          174
```

<210> SEQ ID NO 30
<211> LENGTH: 1347
<212> TYPE: DNA
<213> ORGANISM: Siraitia grosvenorii

<400> SEQUENCE: 30

```
atggaagcta agaactgcaa aaaggttctg atgttcccat ggctggcgca tggtcacata     60
tcaccatttg tagagctggc caagaagctc acagacaaca acttcgccgt ttttctatgt    120
tcttcccctg caaatcttca aaacgtcaag ccaaaactcc cccatcacta ctctgattcc    180
attgaactcg tggagctcaa ccttccatcg tcgccggagc ttcccccctca tatgcacacc    240
```

accaatggcc tccctttgca tttagttccc accctcgttg acgccttgga catggccgct 300
ccgcacttct ccgccatttt acaggaactg aatccagatt ttctcatatt cgacatcttc 360
caaccctggg cggctgaaat cgcttcctcc ttcggcgttc ctgctatttt gttgcttatc 420
gttggatctg ctataaccgc tttaggggtt cattttgtcc ggagctccgg tacggaattc 480
ccctttcccg agcttactaa atcattcaag aaggaggacg accgaaaacc tccaggagat 540
tccggcaacg atagaggaaa acggctattc aaatgtctgc tggacctgga acattcttca 600
gagactattt tggtgaacag ttttacagag atagagggca aatatatgga ctatctctcg 660
gtcttactga agaagaagat ccttccgatt ggtcctttgg ttcagaaaat tggctccgat 720
gacgatgaat cgggaatcct ccggtggctt gacaagaaga aaccgaattc aactgtgtac 780
gtttcgttcg ggagtgagta ctatttgagc aaagaagaca tagcagagct tgcgcatggt 840
ctggaaatca gcggcgtcaa tttcatctgg attgttcggt ttccaaaggg agagaaaatc 900
gccattgaag aggcattacc agatgaattt cttgaaagag tcggagagag aggcgtcgtc 960
gttgatggat gggcgccgca gatgaaaata ttagggcatt cgagcgtcgg cgggtttctg 1020
tctcactgcg gatggaactc tgtgctggag agtctggtgc tcggcgtgcc gatcatatcc 1080
ctgccgatac acctcgaaca gccgtggaac gccttggtag cggagcacgt cggcgtttgt 1140
gtgagggcga agagagacga cggaggaaat cttcaaagag agttggtggc ggaggccatt 1200
aaagaagtgg tggttgagga aacaggagcg gaactgagaa gcaaagcaag agtaattagt 1260
gaaatcttga aaaataaaga agctgaaaca atacaagatt tggtggctga gcttcaccgg 1320
ctttctgacg caagaagagc ttgttga 1347

<210> SEQ ID NO 31
<211> LENGTH: 1389
<212> TYPE: DNA
<213> ORGANISM: Siraitia grosvenorii

<400> SEQUENCE: 31
atggaaaaaa atcttcacat agtgatgctt ccatggtcgg cgttcggcca tctcatacca 60
ttttttcacc tctccatagc cttagccaaa gccaaagttt atatctcctt cgtctccact 120
ccaagaaata ttcagagact ycccccaaatc ccgccggact tagcttcttt catagatttg 180
gtggccattc ccttgccgag actcgacgac gatctgttgc tagaatctgc agaggccact 240
tctgatattc cgatcgacaa gattcagtat ttgaagcgag ccgtcgacct cctccgccac 300
cccttcaaga agtttgtcgc cgaacaatcg ccggactggg tcgtcgttga ttttcatgct 360
tattgggccg gcgagatcta ccaggagttt caagttcccg tcgcctactt ctgtattttc 420
tcggccatct gtttgcttta tcttggacct ccagacgtgt attcgaagga tcctcagatc 480
atggcacgaa tatctcccgt taccatgacg gtgccgccgg agtgggtcgg ttttccgtcc 540
gccgtagcct acaacttgca tgaggcgacg gtcatgtact ctgctctcta tgaaacaaat 600
gggtctggaa taagcgactg cgagaggatt cgccggctcg tcctttcctg tcaagccgtg 660
gccattcgaa gctgcgagga gattgaaggc gaatacctta ggttatgtaa gaaactgatt 720
ccaccgcagg ggattgccgt cggcttgctt ccgccggaaa agccaccaaa atcagatcac 780
gagctcatca aatggcttga cgagcaaaag ctccgattcg tcgtgtacgt gacattcggc 840
agcgaatgca acctgacgaa ggaccaagtt cacgagatag cccacgggct ggaactgtcg 900
gagctgccat ttttatgggc actgaggaaa cccagctggg cagctgagga agacgatggg 960
ctgccgtctg ggtttcgtga gagaacgtcc gggagagggg tggtgagcat ggagtgggtg 1020
ccgcagttgg agattctggc gcaccaggcc atcggcgtct ctttagttca cgggggctgg 1080
ggctctatta tcgagtcgct acaagctggg cactgtctgg ttgtgctgcc gtttatcatc 1140
gaccagccgc tgaactcaaa gcttttggtg gagaaaggga tggcgcttga gatcagaagg 1200
aacggttctg atggatggtt tagtagagaa gacatcgccg gaactttgag agaagctatg 1260
cggtcgtctg aggaaggcgg gcagctgagg agccgtgcaa aagaggcggc ggccatcgtt 1320
ggagatgaga agctgcagtg ggaacaatac ttcggcgcgt tcgtacagtt tctgagggac 1380
aagtcttga 1389

<210> SEQ ID NO 32
<211> LENGTH: 1395
<212> TYPE: DNA
<213> ORGANISM: Siraitia grosvenorii

<400> SEQUENCE: 32
atgtccgagg agaaaggcag agggcacagc tcgtcgacgg agagacacac tgctgccgcc 60
atgaacgccg agaaacgaag caccaaaatc ttgatgctcc catggctggc tcacggccac 120
atatctccat acttcgagct cgccaagagg ctcaccaaga aaaactgcca cgtttacttg 180
tgttcttcgc ctgtaaatct ccaaggcatc aagccgaaac tctctgaaaa ttactcttcc 240
tccattgaac ttgtggagct tcatcttcca tctctccccg accttcctcc ccatatgcac 300
acgaccaaag gcatccctct acatctacaa tccaccctca tcaaagcctt cgacatggcc 360
gcccctgatt tttccgacct gttgcagaaa ctcgagccgg atctcgtcat ttccgatctc 420
ttccagccat gggcagttca attagcgtcg tctcggaaca ttcccgtcgt caatttcgtt 480
gtcaccggag tcgctgttct tagtcgtttg gctcacgtgt tttgcaactc cgttaaggaa 540
ttccctttcc cggaactcga tctaaccgac cattggatct ccaagagccg ccgcaaaacg 600
tccgacgaat taggtcgcga gtgcgcgatg cgatttttca actgcatgaa acaatcttca 660
aacatcactc tagccaacac tttccccgag ttcgaagaaa aatacatcga ttatctctct 720
tcctcgttta agaaaaagat tcttccggtt gctcctctag ttcctgaaat cgacgcagac 780
gacgagaaat cggaaattat cgagtggctt gacaagaaga aaccgaaatc gactgtttac 840
gtttcgtttg ggagtgagta ttatctgacg aaagaagaca gggaagagct cgcccatggc 900
ttagaaaaga gcggcgtgaa tttcatctgg gttattaggt ttccaaaggg cgagaagatc 960
accattgaag aggctttacc agaaggattt ctcgagagag taggggacag gggagtgatt 1020
atcgacgggt gggcgccgca gttgaaaata ttgaggcatt caagcgtggg cgggttcgtg 1080
tgccactgcg ggtggaactc tgtggtggag agcgtggtgt ttggggtgcc gatcatagcc 1140
ttgccgatgc agctcgatca gccatggcat gcgaaggtgg cggaggacgg cggcgtctgt 1200
gcggaggcga agagagacgt tgaagggagc gttcagagag aagaggtggc gaaggccatt 1260
aaagaggtgg tgtttgagaa gaagggggggg gttctgagtg gaaaagcaag agagatcagc 1320
gaggccttga gaaagaggga aggggaaatc atagaggaat tggttgctga gtttcaccag 1380
ctctgtgaag cttga 1395

<210> SEQ ID NO 33
<211> LENGTH: 1242
<212> TYPE: DNA
<213> ORGANISM: Artificial sequence
<220> FEATURE:
<223> OTHER INFORMATION: Partial gene sequence from Siraitia grosvenorii

<400> SEQUENCE: 33
ttctgctcca cgcctgtaaa tttggaagcc attaaaccaa agctttccaa aagctactct 60
gattcgatcc aactaatgga ggttcctctc gaatcgacgc cggagcttcc tcctcactat 120
catacagcca aaggccttcc gccgcattta atgcccaaac tcatgaatgc ctttaaaatg 180
gttgctccca atctcgaatc gatcctaaaa accctaaacc cagatctgct catcgtcgac 240
attctccttc catggatgct tccactcgct tcatcgctca aaattccgat ggttttcttc 300
actattttcg gtgccatggc catctccttt atgatttata atcgaaccgt ctcgaacgag 360
cttccatttc cagaatttga acttcacgag tgctggaaat cgaagtgccc ctatttgttc 420
aaggaccaag cggaaagtca atcgttctta gaatacttgg atcaatcttc aggcgtaatt 480
ttgatcaaaa cttccagaga gattgaggct aagtatgtag actttctcac ttcgtcgttt 540
acgaagaagg ttgtgaccac cggtcccctg gttcagcaac cttcttccgg cgaagacgag 600
aagcagtact ccgatatcat cgaatggcta gacaagaagg agccgttatc gacggtgctc 660
gtttcgtttg ggagcgagta ttatctgtca aaggaagaga tggaagaaat cgcctacggg 720
ctggagagcg ccagcgaggt gaatttcatc tggattgtta ggtttccgat gggacaggaa 780
acggaggtcg aggcggcgct gccggagggg ttcatccaga gggcaggaga gagagggaaa 840
gtggtcgagg gctgggctcc gcaggcgaaa atattggcgc atccgagcac cggcggccat 900
gtgagccaca acgggtggag ctcgattgtg gagtgcttga tgtccggtgt accggtgatc 960
ggcgcgccga tgcaacttga cgggccaatc gtcgcaaggc tggtggagga gatcggcgtg 1020
ggtttggaaa tcaagagaga tgaggaaggg agaatcacga ggggcgaagt tgccgatgca 1080
atcaagacgg tggcggtggg caaaaccggg gaagatttta gaaggaaagc aaaaaaaatc 1140
agcagcattt tgaagatgaa agatgaagaa gaggttgaca ctttggcaat ggaattagtg 1200
aggttatgcc aaatgaaaag agggcaggag tctcaggact aa 1242

<210> SEQ ID NO 34
<211> LENGTH: 912
<212> TYPE: DNA
<213> ORGANISM: Artificial sequence
<220> FEATURE:
<223> OTHER INFORMATION: Partial gene sequence from Siraitia grosvenorii

<400> SEQUENCE: 34
tcccggtcaa cggtagagga cttcacggag cttcgagagt ggatgccttc tggatcgaac 60
atggtctacc ggtaccacga gattaaaaaa tccttagatg gagcaaccgg caacgaatcg 120
gggacgtctg attcggtccg attcggaatt gtgattgagg agagtgttgc tgtggctgta 180
agaagctccc ctgaactgga accggaatgg ttcgatttgc tcgcgaagct ttaccagaag 240
ccagttgttc cggtaggatt tctacctcca gtaattgaag atgcggaaga attgagcagc 300
gatatcaagg aatggttaga caaacagagc tcaaactcgg tcctttacgt cgcattcggg 360
accgaggcga ctctgagtca agatgacgtc actgagttag ccatggggct tgagcaatct 420
gggataccat ttttctgggt actgagaacc tcacctcggg acgagtcaga catgttaccg 480
gccgggttca aggagcgagt cgaaggtcga ggaagtgttc acgtgggatg ggtctcgcag 540
gtgaagatac tgagtcacga ctcggttggc ggttgtttga cacactgtgg atggaactcg 600
atcatagagg ggctcggatt cgggcgcgtt atggtattgt ttccagtcgt gaacgaccag 660
ggattgaacg ctagattgtt gggggagaag aagctcggga tagagataga aagggacgag 720

```
cgagatggat cgttcacacg cgactcggtg tcggaatcgg tgaggtcggc aatggcggaa    780

agttcaggcg aggccttgag agtgagggcc agggaaatga aggggttgtt tggaaacgga    840

gatgagaacg agcatcaact gaacaagttt gtacaatttc tcgaggcaaa caggaatagg    900

cagtccgagt aa                                                        912
```

<210> SEQ ID NO 35
<211> LENGTH: 1125
<212> TYPE: DNA
<213> ORGANISM: Artificial sequence
<220> FEATURE:
<223> OTHER INFORMATION: Partial gene sequence from Siraitia grosvenorii

<400> SEQUENCE: 35

```
ctgctgccga ttccgctgcc gaaaccggcc gccgatctct tgccggaagg tgcagaggcg     60

acggtggata ttccgtccga caagattccg tatctgaaat tggccctcga tctcgccgag    120

cagccgtttc ggaagttcgt cgttgatcgt ccgccggatt ggatgatcgt cgattttaat    180

gctacttggg tctgcgatat ttctcgggag cttcaaatcc caatcgtttt ctttcgtgtt    240

ctttcgcctg gatttcttgc tttctttgcg catgttcttg ggagtggtct gccgctgtcg    300

gagatcgaaa gcctgatgac tccgccggtg atcgacgggt cgacggtggc gtaccgccgg    360

catgaagctg ccgttatttg tgctgggttt tttgagaaga acgcttctgg tatgagtgat    420

cgcgatcggg taaccaaaat tctctctgcc agtcaagcaa tcgcagttcg ttcttgctac    480

gaatttgacg ttgagtattt gaaattgtac gagaaatatt gtggaaaaag agtgattcct    540

ctagggtttc tccctccaga aaagccccaa aagtccgagt tcgccgccga ttcgccatgg    600

aaaccgacct tcgagtggct tgacaaacaa aagccccgat cagtggtgtt cgtcggattc    660

ggcagcgaat gcaaactcac gaaagatgat gtttacgaga tagcgcgcgg ggtggagctg    720

tcggagctgc catttttgtg ggctctgaga aaaccgatct gggcggcggc ggacgattcc    780

gacgctctgc ctgccggatt cctcgagcgg acggcggaga gagggattgt gagcatgggg    840

tgggcgccgc agatggagat tttaacgcac ccgtcgattg gcggctctct gtttcacgcc    900

gggtggggat ccgccattga agctctgcaa ttcgggcatt gccttgttct gttgccattc    960

atcgtggatc agccactgaa tgcaaggctt ctggtggaga agggtgttgc agtcgaagtt   1020

ggaagaaagg aagacgggtc ttttagtgga gaagacatag ctaaagctct gagagaagct   1080

atggtttcag aagaaggtga gcagatgagg aggcaagcga gaaag                   1125
```

<210> SEQ ID NO 36
<211> LENGTH: 486
<212> TYPE: DNA
<213> ORGANISM: Artificial sequence
<220> FEATURE:
<223> OTHER INFORMATION: Partial gene sequence from Siraitia grosvenorii

<400> SEQUENCE: 36

```
atggaaaacg acggcgtttt gcacgtggtg gtattcccat ggctagcctt gggtcatctc     60

attcctttcg ctcgactcgc cacctgctta gcccacaagg gtctcagggt ttcgttcgta    120

tcaaccacaa ggaacctgag cagaattccc aaaatacccc cacatctctc ctcctccgtc    180

aacctcgtcg gctttcctct gccccacgtc gacggccttc cggacgccgc cgaggcttcc    240

tccgacgtgc cttacaacaa gcaacagtta ctgaagaagg ccttcgactc tctggaatca    300

ccgctcgccg atttgcttcg tgatttgaat cccgattgga ttatctacga ttacgcctct    360

cattggcttc cgcagctcgc ggcggagctc cgtatctcgt ctgttttctt cagcctcttc    420
```

-continued

```
accgcggcgt ttcttgcttt tcttggccca ccgtcggcgt tgtccggcga cggcagttcc    480

cggtga                                                               486
```

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41
<211> LENGTH: 1461
<212> TYPE: DNA
<213> ORGANISM: Siraitia grosvenorii

<400> SEQUENCE: 41

```
gtggggccgt cgtctgttga agctcctcag cggacgattt cgaagcctga acagagggag     60

ctaccgttga ggaagattcc cggggactat gggccgccgt tgttgggtcc gattaaggac    120

cgacaagact atttttacaa tcaggggagg gaggagttcc tgagatcacg catgaacagg    180

tacgaatcaa ctgtgtacag aactaatatg ccaccaggtc cctttatctc ctccgattct    240

cgtgtcatcg ttttactcga cggcaagagc ttccctgtac tcttcgacgt ttctaaagtt    300

ctgaaacaag acgtcttcac cggaacttat atgcccttaa cggagctcac tggcggctac    360

cgagttcttt cttatctcga cccctccgag cccgatcacg agaagcttaa acagttcctc    420

ttctacctcc tcaagtaccg tcgcgacaag attctgccgg agtttcactc taccttttcg    480

gagctgtttg agactctgga gaaggaggtg gctgccgccg gtagagcaga ttataatgat    540

cccggtgaac aggcggcgtt taacttcttg gctcggtctc tgttcggcgc caacccgccc    600

gacaccaaac tgggaaacga cgctccgagt ttaatatcca aatgggtgct gttccagctg    660

ggtccggttc tcactcttgg tcttcccaag cctgtcgagg agcttctcct gcgaaccgtc    720

cggctgccac cggcgcttgt gaaatcggat taccagcggc tgtacgattt cttttacgag    780

gcgtcggagg ctgtgtttgc ggaggcggat agattgggca ttgcgagaga ggaagcgtgt    840

cacaacttgg tcttcgccac gtgcttcaat tccttcggag ggatgaagat cctcttcccc    900

aatatgataa aatggatcgg acgtgccgga gtgaatctcc atacggagct cgcacgggag    960

ataagatccg ccgtcaaagc ccacggcggc aagatcacga tggcggctat ggaacagatg   1020

ccgctgatga agtccgtagt gtacgaaacg ctcagaatcg aacccccggt tcctgcgcaa   1080

tacgggcgag cgaaggagga cctggtgatc gagagccacg acgccgcttt cgagatcaaa   1140
```

-continued

```
gaaggggaaa tgttgtgtgg gtaccagcca ttcgccacta gagatccgaa aatattcgag   1200

agatccgaag aattcgtacc ggatcggttc accggcgacg gcgaggagtt gctgaagcac   1260

gtgctctggt caaacggacc ggagactcaa tccccaaccg ttaaagacaa gcagtgcgct   1320

ggcaaagact tcatagtctt cgtctcccgc ctcctcgtcg tcgaactctt cctccgatac   1380

gactccttcg acattgaagt cgcagcttcg ccgttgggcg ccgccgtcac cataacttcc   1440

ctgaagaagg caagctttta a                                             1461
```